United States Patent
Guo et al.

(10) Patent No.: US 8,722,709 B2
(45) Date of Patent: May 13, 2014

(54) MINERALOCORTICOID RECEPTOR ANTAGONISTS

(75) Inventors: Xin Guo, Danbury, CT (US); Stephen J. Boyer, Bethany, CT (US); Di Wu, Danbury, CT (US); Frank Wu, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 60 days.

(21) Appl. No.: 13/290,392

(22) Filed: Nov. 7, 2011

(65) Prior Publication Data

US 2012/0289551 A1     Nov. 15, 2012

Related U.S. Application Data

(60) Provisional application No. 61/412,244, filed on Nov. 10, 2010.

(51) Int. Cl.
*A61K 31/4439* (2006.01)
*C07D 401/04* (2006.01)

(52) U.S. Cl.
USPC ............. 514/341; 546/275.4; 546/276.1

(58) Field of Classification Search
CPC .................. C07D 401/04; A61K 31/4439
USPC .................. 546/275.4, 276.1; 514/341
See application file for complete search history.

(56) References Cited

U.S. PATENT DOCUMENTS 8,492,409 B2 *   7/2013   Li et al. ................ 514/340

FOREIGN PATENT DOCUMENTS

| WO | 2005066161 A1 | 7/2005 |
| WO | 2006014877 A2 | 2/2006 |
| WO | 2010116282 A1 | 10/2010 |

OTHER PUBLICATIONS

International Search Report, Form PCT/ISA/210, and Written Opinion, Form PCT/ISA/237, for corresponding PCT/US2011/059526; date of mailing: Jan. 25, 2012.

* cited by examiner

*Primary Examiner* — Patricia L Morris
(74) *Attorney, Agent, or Firm* — Michael P. Morris; Alan R. Stempel

(57) ABSTRACT

Mineralocorticoid receptor antagonists, of which the following is exemplary.

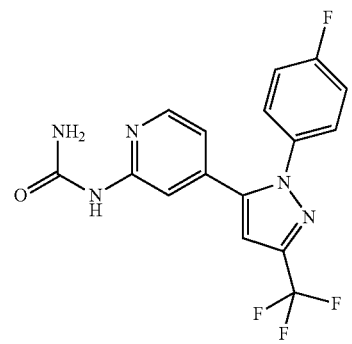

6 Claims, No Drawings

MINERALOCORTICOID RECEPTOR ANTAGONISTS

BACKGROUND OF THE INVENTION

1. Technical Field

The present invention relates to novel urea pyridine compounds which are mineralocorticoid receptor antagonists (also known as aldosterone receptor antagonists), methods for the production of such compounds, the use of such compounds in the treatment of various diseases and pharmaceutical compositions comprising such compounds.

2. Background Information

The mineralocorticoid receptor (often referred to by the abbreviations MR, MLR and MCR) is a nuclear receptor. It is often called the aldosterone receptor because, as explained more fully below, a key activating ligand for this receptor is aldosterone.

Nuclear receptors are a class of proteins found within the interior of cells. They have the ability to directly bind to DNA and regulate the expression of adjacent genes. The regulation of gene expression by a nuclear receptor occurs when a ligand is present and binds to the nuclear receptor. Ligand binding results in a conformational change in the receptor which activates the receptor and brings about regulation of gene expression.

The mineralocorticoid receptor is expressed in many tissues, such as the kidney, colon, heart, central nervous system (hippocampus), brown adipose tissue and sweat glands. In epithelial tissues, its activation leads to the expression of proteins regulating ionic and water transports (mainly the epithelial sodium channel or ENaC, Na+/K+ pump, serum and glucocorticoid induced kinase or SGK1) resulting in the reabsoprtion of sodium, and as a consequence an increase in extracellular volume, increase in blood pressure, and an excretion of potassium to maintain a normal salt concentration in the body.

The receptor is activated by binding to ligands known as mineralocorticoids. These include aldosterone and deoxycorticosterone as well as glucocorticoids, like cortisol and corticosterone. The mineralocorticoid receptor also responds to some progestins.

Increased levels of the mineralocorticoid, aldosterone, are present in primary and secondary hyperaldosteronism. In primary aldosteronism, the adrenal glands produce an excess of aldosterone, causing loss of potassium and retention of sodium. The excess sodium in turn causes water retention, increasing blood volume and blood pressure. Secondary aldosteronism is increased adrenal production of aldosterone in response to nonpituitary, extra-adrenal stimuli. Secondary aldosteronism is caused by reduced renal blood flow, which stimulates the renin-angiotensin mechanism leading to hypersecretion of aldosterone. Causes of reduced renal blood flow include obstructive renal artery disease (eg, atheroma, stenosis), renal vasoconstriction (as occurs in accelerated hypertension), and edematous disorders (eg, heart failure, cirrhosis with ascites and nephrotic syndrome).

The mineralocorticoid receptor antagonists, also known as aldosterone antagonists, are a known class of drugs which antagonize the action of aldosterone at mineralocorticoid receptors. Antagonism of these receptors inhibits sodium resorption in the collecting duct of the nephron in the kidneys. This inhibits sodium/potassium exchange, reducing urinary potassium excretion and weakly increasing water excretion. This diuretic activity reduces edema and blood pressure. As a consequence, this group of drugs is often used for the treatment of primary hyperaldosteronism and edematous conditions including congestive heart failure, cirrhosis of the liver accompanied by edema and/or ascites, the nephrotic syndrome, essential hypertension and hypokalemia. In addition, mineralocorticoid receptor antagonist has anti-inflammatory and anti-fibrotic effects which are independent of blood pressure lowering effects. Treatment of mineralocorticoid receptor antagonist has shown beneficial effects in Chronic Kidney Disease (Cortinovis et. al., Ther Adv Cardiovasc Dis 2009; 3:133-43), End Stage Renal Disease (Taheri S et. al., Saudi J Kidney Dis Transspl 2009; 79: 863-9), arthritis (Syngle A et. al, Scand J Rheumatol, 2009; 38:15-22), atherosclerosis (Takai S et. al, Hypertension, 2005; 46:1135-39), and stroke (Osmond J M et. al., Clin Sci, 2008; 114: 37-47).

Members of the class of mineralocorticoid receptor or aldosterone antagonists which are currently marketed for clinical use include spironolactone and eplerenone. Spironolactone is actually a prodrug which produces canrenone as an active first metabolite. The latter is not marketed for clinical use.

A number of marketed dihydropyridine calcium channel blockers have also been noted to have mineralocorticoid receptor antagonist activity. (Dietz et al., Hypertension, 2008; 51:742-748)

BRIEF SUMMARY OF THE INVENTION

The present invention provides novel compounds as antagonists of the mineralocorticoid (aldosterone) receptor and methods for making these compounds. The invention also provides pharmaceutical compositions comprising these compounds. The invention further provides a method for the treatment of primary hyperaldosteronism and edematous conditions including congestive heart failure, cirrhosis of the liver accompanied by edema and/or ascites, the nephrotic syndrome, essential hypertension and hypokalemia through administration of such compounds.

TERMS AND DEFINITIONS USED

By the term "alkyl" or "alkyl group" is meant a monovalent, noncyclic, saturated hydrocarbon radical with the general formula $C_nH_{2n+1}$. An alkyl group can be straight- or branch-chained. Thus, "$C_{1-6}$-alkyl" means straight chained or branched alkyl groups with 1, 2, 3, 4, 5 or 6 carbon atoms. Examples include: methyl, ethyl, n-propyl, iso-propyl, n-butyl, iso-butyl, tert.butyl, n-penty and n-hexyl. The following abbreviations may also optionally be used for the above-mentioned groups: Me, Et, n-Pr, i-Pr, n-Bu, i-Bu, t-Bu, etc. etc. Unless stated otherwise, the definition propyl includes all the possible isomeric forms of the group. Thus, for example, propyl includes n-propyl and iso-propyl. Likewise, unless stated otherwise, butyl includes, n-butyl, iso-butyl and tert.butyl.

By the term "cycloalkyl" or "cycloalkyl group" is meant a monovalent, monocyclic, saturated hydrocarbon radical with the general formula $C_nH_{2n-1}$ where n=number of carbon atoms. Thus, "$C_{3-7}$-cylcoalkyl" means a cycloakly group with 3, 4, 5, 6 or 7 carbon atoms, which and the term would encompass cyclopropane, cyclobutane, cyclopentane, cyclohexane and cycloheptane.

By the term "halogen" is meant a fluorine, chlorine, bromine or iodine atom, with fluorine, chlorine and bromine being preferred.

DETAILED DESCRIPTION OF THE INVENTION

In a generic aspect, the present invention provides novel compounds of the formula I

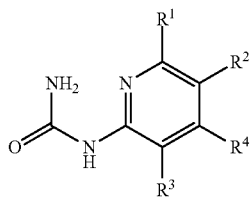
(I)

wherein:

R¹, R² and R³ are each, independently, H, halogen, —CN, —OH, C$_{1-6}$-alkyl (which is optionally substituted with up to 4 halogen atoms), C$_{3-7}$-cycloalkyl, C$_{1-6}$-alkenyl, C$_{1-6}$-alkynyl, C$_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$ or —NR$^a$SO$_2$R$^b$;

R⁴ is a group of the formula

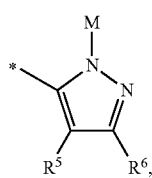
(II)

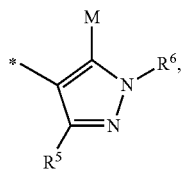
(III)

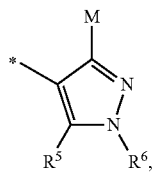
(IV)

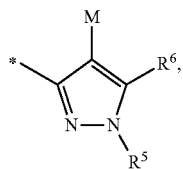
(V)

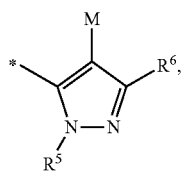
(VI)

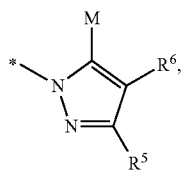
(VII)

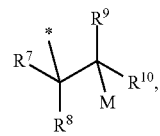
(VIII)

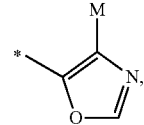
(IX)

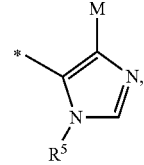
(X)

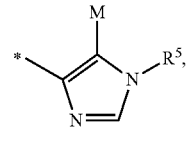
(XI)

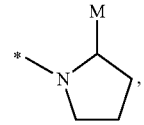
(XII)

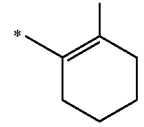
(XIII)

or

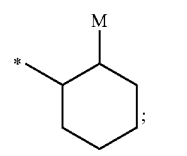
(XIV)

R⁵, R⁶, R⁷, R⁸, R⁹ and R¹⁰ are each, independently, (a) H,
(b) halogen,
(c) —CN,
(d) —OH,
(e) C$_{1-6}$-alkyl which is optionally substituted with up to 4 groups which are each, independently, —OR$^a$, —OC(O)R$^a$, —CN, halogen, —NO$_2$, —CO$_2$R$^a$, —C(O)NR$^a$R$^b$, —NR$^a$C(O)R$^b$, —NR$^a$R$^b$, —SO$_2$R$^a$, —SO$_2$OR$^a$, —OSO$_2$R$^a$, —SO$_2$NR$^a$R$^b$, —NR$^a$SO$_2$R$^b$, C$_{3-7}$-cycloalkyl, an optionally substituted 5 to 6-membered aromatic ring or heteroaromatic ring (wherein the heteroatoms are O, S or N) or a saturated or partially saturated 5 to 7-membered carbocyclic ring in which up to 3 ring constituting carbons are optionally replaced with O, S, NR$^a$, SO, SO$_2$ or C(O),
(f) C$_{3-7}$-cycloalkyl which is optionally substituted with up to 4 groups which are each, independently, —OR$^a$, —OC(O)R$^a$, —CN, halogen, —NO$_2$, —CO$_2$R$^a$, —C(O)NR$^a$R$^b$, —NR$^a$C(O)R$^b$, —NR$^a$R$^b$, —SO$_2$R$^a$, —SO$_2$OR$^a$, —OSO$_2$R$^a$, —SO$_2$NR$^a$R$^b$, —NR$^a$SO$_2$R$^b$, $C_{1-6}$-alkyl or an optionally substituted 5 to 6-membered aromatic ring or heteroaromatic ring (wherein the heteroatoms are O, S or N),
(g) $C_{1-6}$-alkenyl,
(h) $C_{1-6}$-alkynyl,
(i) $C_{1-6}$-alkoxy,
(j) —$NO_2$,
(k) —$CO_2R^a$,
(l) —$C(O)NR^aR^b$,
(m) —$NR^aC(O)R^b$,
(n) —$NR^aR^b$,
(o) —$SO_2R^a$,
(p) —$SO_2NR^aR^b$,
(q) —$NR^aSO_2R^b$,
(r) optionally substituted aryl,
(s) an optionally substituted 5 to 6-membered heteroaromatic ring, or
(t) an optionally substituted, saturated or partially saturated, 5 to 7 membered carbocyclic ring in which up to 3 ring constituting carbons are optionally replaced with O, S, $NR^a$, SO, $SO_2$ or C(O); or $R^7$ and $R^8$ (together with the carbon atom between them) and $R^9$ and $R^{10}$, (together with the carbon atom between them) each optionally form a saturated or partially saturated, 3 to 7 membered carbocyclic ring in which up to 3 ring constituting carbons are optionally replaced with O, S, $NR^a$, SO, $SO_2$ or C(O);

M is
(a) $C_{1-6}$-alkyl, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —$NO_2$, —$CO_2R^a$, —$C(O)NR^aR^b$, —$NR^aC(O)R^b$, —$NR^aR^b$, —$SO_2R^a$, —$SO_2NR^aR^b$, —$NR^aSO_2R^b$ and an optionally substituted aryl;
(b) $C_{3-7}$-cycloalkyl, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —$NO_2$, —$CO_2R^a$, —$C(O)NR^aR^b$, —$NR^aC(O)R^b$, —$NR^aR^b$, —$SO_2R^a$, —$SO_2NR^aR^b$, —$NR^aSO_2R^b$ and an optionally substituted aryl;
(c) a 6 to 10-membered monocyclic or fused bicyclic aromatic ring, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —$NO_2$, —$CO_2R^a$, —$C(O)NR^aR^b$, —$NR^aC(O)R^b$, —$NR^aR^b$, —$SO_2R^a$, —$SO_2NR^aR^b$, —$NR^aSO_2R^b$ and an optionally substituted aryl or
(d) a 5 to 10-membered monocyclic or fused bicyclic aromatic heterocyclic ring, in which up to 4 hetero atoms are O, S or N, which heterocyclic ring is optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —$NO_2$, —$CO_2R^a$, —$C(O)NR^aR^b$, —$NR^aC(O)R^b$, —$NR^aR^b$, —$SO_2R^a$, —$SO_2NR^aR^b$, —$NR^aSO_2R^b$ and an optionally substituted aryl.

Ra and Rb are, independently, H or $C_{1-6}$-alkyl which is optionally mono- or di-substituted with —OH, —COOH, $C_{1-6}$-alkoxy, amino or mono- or di-$C_{1-6}$-alkyl amino.

In a first subgeneric aspect, the invention provides compounds of the formula I wherein:

$R^1$, $R^2$ and $R^3$ are each, independently, H, halogen, —CN, $C_{1-6}$-alkyl (which is optionally substituted with up to 4 halogen atoms), $C_{3-7}$-cycloalkyl and $C_{1-6}$-alkoxy;

$R^4$ is a group of the formula

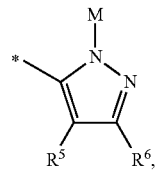

(II)

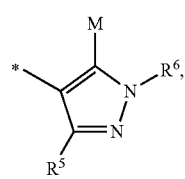

(III)

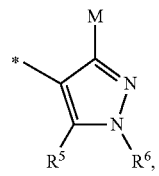

(IV)

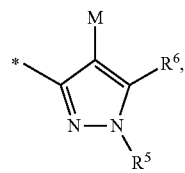

(V)

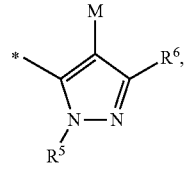

(VI)

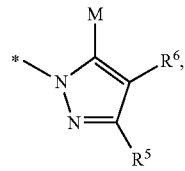

(VII)

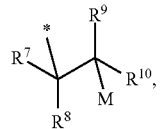

(VIII)

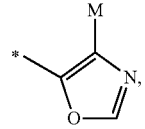

(IX)

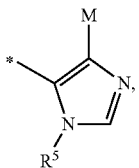 (X)

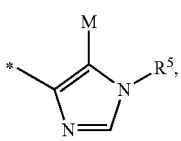 (XI)

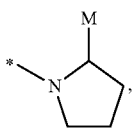 (XII)

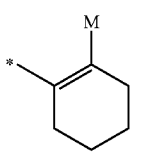 (XIII) or

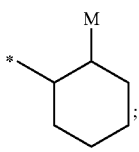 (XIV);

$R^5$, $R^6$, $R^7$, $R^8$, $R^9$ and $R^{10}$ are each, independently,
(a) H,
(b) halogen,
(c) —CN,
(d) —OH,
(e) $C_{1-6}$-alkyl which is optionally substituted with up to 4 groups which are each, independently, —OR$^a$, —OC(O)R$^a$, —CN, halogen, —CO$_2$R$^a$, —C(O)NR$^a$R$^b$, —NR$^a$C(O)R$^b$, NR$^a$R$^b$, —SO$_2$R$^a$, —SO$_2$NR$^a$R$^b$, —NR$^a$SO$_2$R$^b$, $C_{3-7}$-cycloalkyl, a phenyl (which is optionally substituted with up to 2 groups selected from $C_{1-3}$-alkyl, —OR$^a$, —CN or halogen), a 5 to 6 membered heteroaromatic ring (wherein the heteroatoms are O, S or N and the ring is optionally substituted with up to 2 groups selected from $C_{1-3}$-alkyl, —OR$^a$, —CN or halogen) or a saturated or partially saturated 5 to 7-membered carbocyclic ring in which up to 3 ring constituting carbons are optionally replaced with O, S, NR$^a$, SO, SO$_2$ or C(O),
(f) $C_{3-7}$-cycloalkyl which is optionally substituted with up to 4 groups which are each, independently, —OR$^a$, —OC(O)R$^a$, —CN, halogen, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$, $C_{1-6}$-alkyl, a phenyl (which is optionally substituted with up to 2 groups selected from $C_{1-3}$-alkyl, —OR$^a$, —CN or halogen), a 5 to 6 membered heteroaromatic ring (wherein the heteroatoms are O, S or N and the ring is optionally substituted with up to 2 groups selected from $C_{1-3}$-alkyl, —OR$^a$, —CN or halogen),
(g) $C_{1-6}$-alkoxy,
(h) a phenyl which is optionally substituted with up to 2 groups selected from $C_{1-3}$-alkyl, —OR$^a$, —CN or halogen, or
(i) a 5 to 6 membered heteroaromatic ring wherein the heteroatoms are O, S or N and the ring is optionally substituted with up to 2 groups selected from $C_{1-3}$-alkyl, —OR$^a$, —CN or halogen; or $R^7$ and $R^8$ (together with the carbon atom between them) and $R^9$ and $R^{10}$, (together with the carbon atom between them) each optionally form a saturated or partially saturated, 3 to 7 membered carbocyclic ring in which up to 3 ring constituting carbons are optionally replaced with O, S, NR$^a$, SO, SO$_2$ or C(O);

M is
(a) $C_{1-6}$-alkyl, optionally substituted with one or more moieties independently selected from the group consisting of halogen, —CN, —OH, —OC(O)R$^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$ and phenyl (which is optionally substituted with up to 3 groups selected from halogen, —CN, —OH, —OC(O)R$^a$, $C_{1-3}$-alkyl, $C_{1-3}$-alkoxy, —CO$_2$R$^a$, —C(O)NR$^a$R$^b$, NR$^a$C(O)R$^b$, —NR$^a$R$^b$, —SO$_2$R$^a$, —SO$_2$NR$^a$R$^b$ and —NR$^a$SO$_2$R$^b$);
(b) $C_{3-7}$-cycloalkyl, optionally substituted with one or more moieties independently selected from the group consisting of halogen, —CN, —OH, —OC(O)R$^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$ and —NR$^a$SO$_2$R$^b$;
(c) a 6 to 10-membered monocyclic or fused bicyclic aromatic ring, optionally substituted with one or more moieties independently selected from the group consisting of halogen, —CN, —OH, —OC(O)R$^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$ and —NR$^a$SO$_2$R$^b$ or
(d) a 5 to 10-membered monocyclic or fused bicyclic aromatic heterocyclic ring, in which up to 4 hetero atoms are O, S or N, which heterocyclic ring is optionally substituted with one or more moieties independently selected from the group consisting of halogen, —CN, —OH, —OC(O)R$^a$, $C_{1-6}$-alkyl (which is optionally substituted with up to 4 halogen atoms), $C_{3-6}$-cycloalkyl, $C_{1-6}$-alkenyl, $C_{1-6}$-alkynyl, $C_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$ and —NR$^a$SO$_2$R$^b$.

Ra and Rb are, independently, H or $C_{1-6}$-alkyl which is optionally mono- or di-substituted with —OH, —COOH, $C_{1-6}$-alkoxy, amino or mono- or di-$C_{1-6}$-alkyl amino.

In a second subgeneric aspect, the invention provides compounds of the formula I wherein:
$R^1$, $R^2$ and $R^3$ are each, independently, H, halogen, —CN or $C_{1-6}$-alkyl (which is optionally substituted with up to 4 halogen atoms);

$R^4$ is a group of the formula

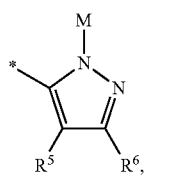
(II)

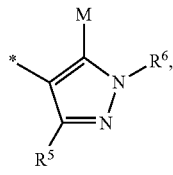
(III)

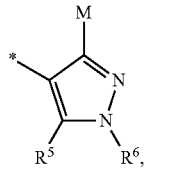
(IV)

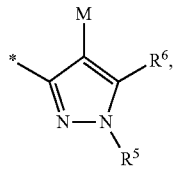
(V)

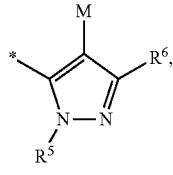
(VI)

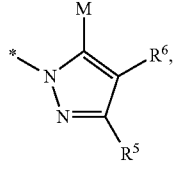
(VII)

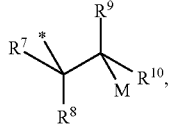
(VIII)

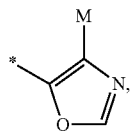
(IX)

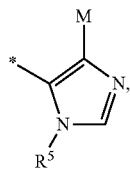
(X)

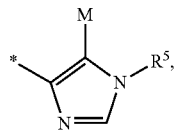
(XI)

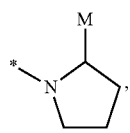
(XII)

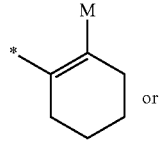
or
(XIII)

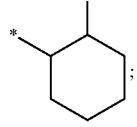
;
(XIV)

$R^5$, $R^6$, $R^7$, $R^8$, $R^9$ and $R^{10}$ are each, independently,
(a) H,
(b) —OH,
(c) halogen, or
(d) $C_{1-6}$-alkyl which is optionally substituted with up to 4 groups which are each, independently, —CN, —OR$^a$, —OC(O)R$^a$ or halogen; or $R^7$, $R^8$, $R^9$ and $R^{10}$ each are each, independently,
(a) $C_{3-7}$-cycloalkyl which is optionally substituted with up to 4 groups which are each, independently, —CN, —OR$^a$, —OC(O)R$^a$ or halogen;
(b) phenyl which is optionally substituted with up to 2 groups which are $C_{1-3}$-alkyl, —OR$^a$, —CN or halogen;

M is
(a) $C_{1-6}$-alkyl, optionally substituted with one or more moieties independently selected from the group consisting of halogen, —CN, —OH, —OC(O)R$^a$, $C_{1-6}$-alkyl (which is optionally substituted with up to 4 halogen atoms), $C_{3-6}$-cycloalkyl, $C_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$ and phenyl (which is optionally substituted with up to 3 groups selected from halogen, —CN, —OH, —OC(O)R$^a$, $C_{1-3}$-alkyl, $C_{1-3}$-alkoxy, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$ and —NR$^a$SO$_2$R$^b$);
(b) $C_{3-7}$-cycloalkyl, optionally substituted with one or more moieties independently selected from the group consisting of halogen, —CN, —OH, —OC(O)R$^a$, $C_{1-6}$-alkyl (which is optionally substituted with up to 4 halogen atoms), $C_{3-6}$-cycloalkyl, $C_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$ and —NR$^a$SO$_2$R$^b$;
(c) a phenyl, optionally substituted with one or more moieties independently selected the group consisting of halogen, —CN, —OH, —OC(O)R$^a$, $C_{1-6}$-alkyl (which is optionally substituted with up to 4 halogen atoms), $C_{3-6}$-cycloalkyl, $C_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, and —NR$^a$SO$_2$R$^b$ or (d) a 5 to 6-membered heteroaromatic ring, in which the hetero atoms are O, S or N, which heterocyclic ring is optionally substituted with one or more moieties independently selected from the group consisting of halogen, —CN, —OH, —OC(O)R$^a$, C$_{1-6}$-alkyl (which is optionally substituted with up to 4 halogen atoms), C$_{3-6}$-cycloalkyl, C$_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$.

Ra and Rb are, independently, H or C$_{1-6}$-alkyl which is optionally mono- or di-substituted with —OH, —COOH, C$_{1-6}$-alkoxy, amino or mono- or di-C$_{1-6}$-alkyl amino.

The invention further embraces salts, especially pharmaceutically acceptable salts, of compounds of formula I.

It will be appreciated that a compound of the formula I will have at least one chiral center. The invention includes all possible enantiomers and diastereoisomers of any particular compound of the formula I or any mixture of stereoisomers thereof, including but not limited to the racemate.

It will be further appreciated that some compounds of the formula I may exhibit tautomerism. The invention embraces not only the tautomeric form expressly described but also other tautomeric forms which are implicit.

Of particular note are the compounds of the invention listed below in Table 1.

TABLE 1

| Compound | Structure | Name |
|---|---|---|
| 1 | 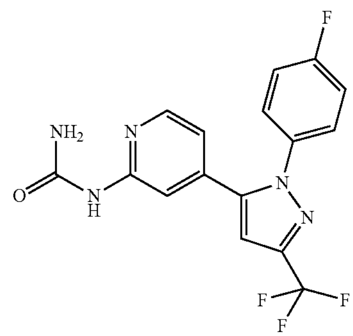 [SMILES: NC(=O)Nc1cc(-c2cc(C(F)(F)F)nn2-c2ccc(F)cc2)ccn1] | {4-[2-(4-Fluoro-phenyl)-5-trifluoromethyl-2H-pyrazol-3-yl]-pyridin-2-yl}-urea |
| 2 | 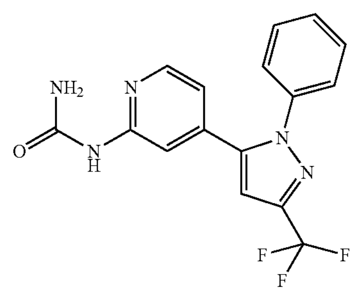 [SMILES: NC(=O)Nc1cc(-c2cc(C(F)(F)F)nn2-c2ccccc2)ccn1] | [4-(2-Phenyl-5-trifluoromethyl-2H-pyrazol-3-yl)-pyridin-2-yl]-urea |
| 3 | 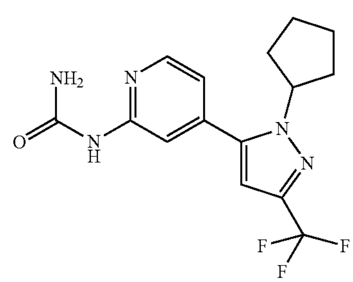 [SMILES: NC(=O)Nc1cc(-c2cc(C(F)(F)F)nn2C2CCCC2)ccn1] | [4-(2-Cyclopentyl-5-trifluoromethyl-2H-pyrazol-3-yl)-pyridin-2-yl]-urea |
| 4 | 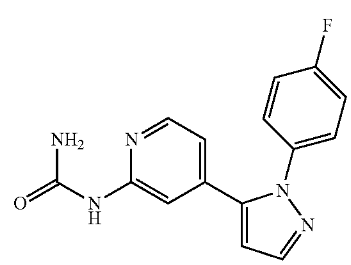 [SMILES: NC(=O)Nc1cc(-c2ccnn2-c2ccc(F)cc2)ccn1] | {4-[2-(4-Fluoro-phenyl)-2H-pyrazol-3-yl]-pyridin-2-yl}-urea |

TABLE 1-continued

| Compound | Structure | Name |
| --- | --- | --- |
| 5 | 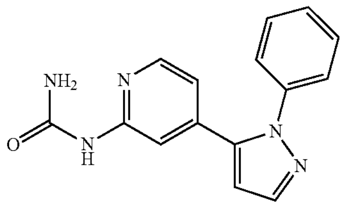 [SMILES: NC(=O)Nc1cc(-c2ccnn2-c2ccccc2)ccn1] | [4-(2-Phenyl-2H-pyrazol-3-yl)-pyridin-2-yl]-urea |
| 6 | 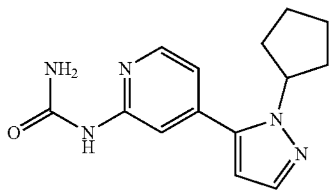 [SMILES: NC(=O)Nc1cc(-c2ccnn2C2CCCC2)ccn1] | [4-(2-Cyclopentyl-2H-pyrazol-3-yl)-pyridin-2-yl]-urea |
| 7 | 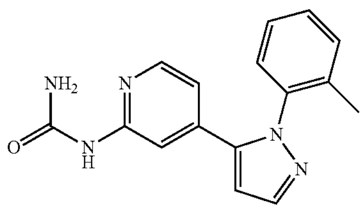 [SMILES: Cc1ccccc1-n1nccc1-c1ccnc(NC(N)=O)c1] | [4-(2-o-Tolyl-2H-pyrazol-3-yl)-pyridin-2-yl]-urea |
| 8 | 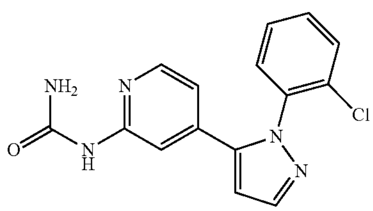 [SMILES: NC(=O)Nc1cc(-c2ccnn2-c2ccccc2Cl)ccn1] | {4-[2-(2-Chloro-phenyl)-2H-pyrazol-3-yl]-pyridin-2-yl}-urea |
| 9 | 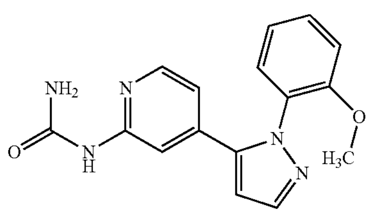 [SMILES: COc1ccccc1-n1nccc1-c1ccnc(NC(N)=O)c1] | {4-[2-(2-Methoxy-phenyl)-2H-pyrazol-3-yl]-pyridin-2-yl}-urea |
| 10 | 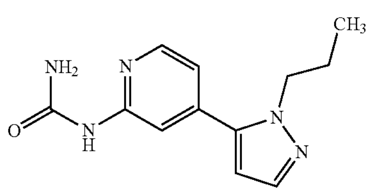 [SMILES: CCCn1nccc1-c1ccnc(NC(N)=O)c1] | [4-(2-Propyl-2H-pyrazol-3-yl)-pyridin-2-yl]-urea |
| 11 | 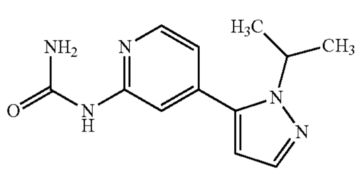 [SMILES: CC(C)n1nccc1-c1ccnc(NC(N)=O)c1] | [4-(2-Isopropyl-2H-pyrazol-3-yl)-pyridin-2-yl]-urea |

TABLE 1-continued

| Compound | Structure | Name |
|---|---|---|
| 12 | 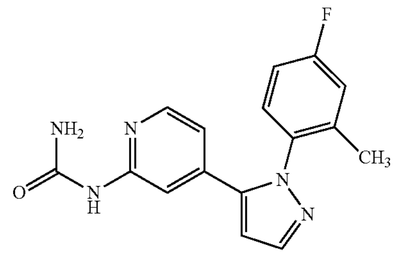 [SMILES: Cc1cc(F)ccc1-n1nccc1-c1ccnc(NC(N)=O)c1] | {4-[2-(4-Fluoro-2-methyl-phenyl)-2H-pyrazol-3-yl]-pyridin-2-yl}-urea |
| 13 | 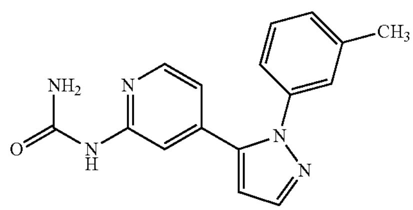 [SMILES: Cc1cccc(-n2nccc2-c2ccnc(NC(N)=O)c2)c1] | [4-(2-m-Tolyl-2H-pyrazol-3-yl)-pyridin-2-yl]-urea |
| 14 | 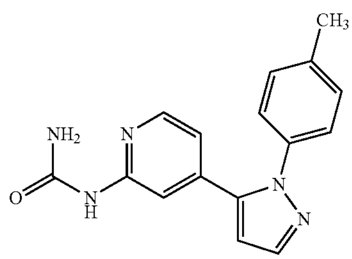 [SMILES: Cc1ccc(-n2nccc2-c2ccnc(NC(N)=O)c2)cc1] | [4-(2-p-Tolyl-2H-pyrazol-3-yl)-pyridin-2-yl]-urea |
| 15 | 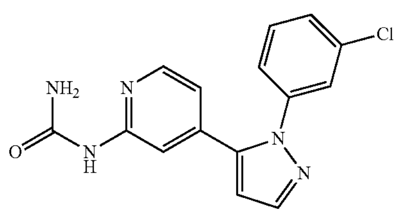 [SMILES: NC(=O)Nc1cc(-c2ccnn2-c2cccc(Cl)c2)ccn1] | {4-[2-(3-Chloro-phenyl)-2H-pyrazol-3-yl]-pyridin-2-yl}-urea |
| 16 | 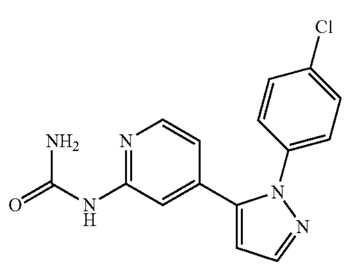 [SMILES: NC(=O)Nc1cc(-c2ccnn2-c2ccc(Cl)cc2)ccn1] | {4-[2-(4-Chloro-phenyl)-2H-pyrazol-3-yl]-pyridin-2-yl}-urea |
| 17 | 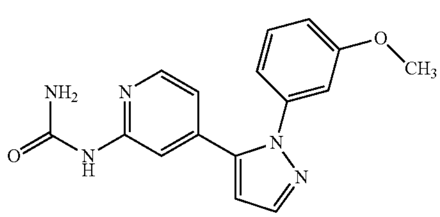 [SMILES: COc1cccc(-n2nccc2-c2ccnc(NC(N)=O)c2)c1] | {4-[2-(3-Methoxy-phenyl)-2H-pyrazol-3-yl]-pyridin-2-yl}-urea |

TABLE 1-continued

| Compound | Structure | Name |
|---|---|---|
| 18 | 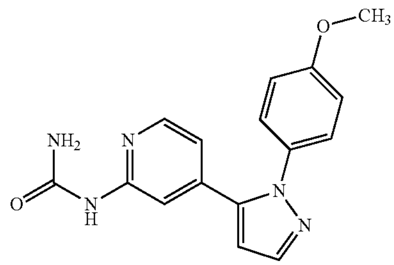 [SMILES: COc1ccc(-n2nccc2-c2ccnc(NC(N)=O)c2)cc1] | {4-[2-(4-Methoxy-phenyl)-2H-pyrazol-3-yl]-pyridin-2-yl}-urea |
| 19 | 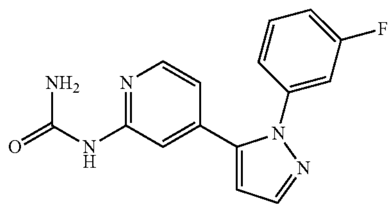 [SMILES: NC(=O)Nc1cc(-c2ccnn2-c2cccc(F)c2)ccn1] | {4-[2-(3-Fluoro-phenyl)-2H-pyrazol-3-yl]-pyridin-2-yl}-urea |
| 20 | 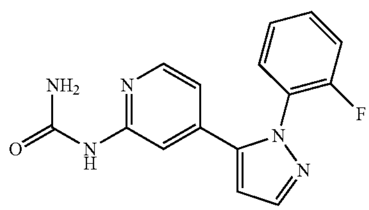 [SMILES: NC(=O)Nc1cc(-c2ccnn2-c2ccccc2F)ccn1] | {4-[2-(2-Fluoro-phenyl)-2H-pyrazol-3-yl]-pyridin-2-yl}-urea |
| 21 | 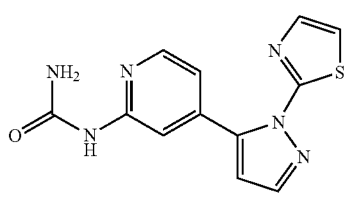 [SMILES: NC(=O)Nc1cc(-c2ccnn2-c2nccs2)ccn1] | [4-(2-Thiazol-2-yl-2H-pyrazol-3-yl)-pyridin-2-yl]-urea |
| 22 | 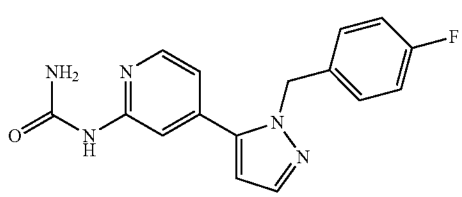 [SMILES: NC(=O)Nc1cc(-c2ccnn2Cc2ccc(F)cc2)ccn1] | {4-[2-(4-Fluoro-benzyl)-2H-pyrazol-3-yl]-pyridin-2-yl}-urea |
| 23 | 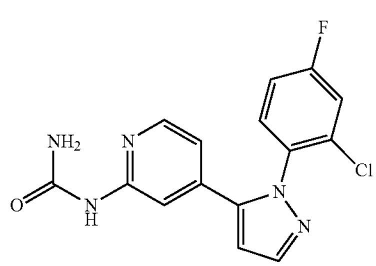 [SMILES: NC(=O)Nc1cc(-c2ccnn2-c2ccc(F)cc2Cl)ccn1] | {4-[2-(2-Chloro-4-fluoro-phenyl)-2H-pyrazol-3-yl]-pyridin-2-yl}-urea |
| 24 | 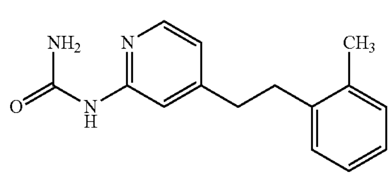 [SMILES: Cc1ccccc1CCc1ccnc(NC(N)=O)c1] | [4-(2-o-Tolyl-ethyl)-pyridin-2-yl]-urea |

TABLE 1-continued

| Compound | Structure | Name |
|---|---|---|
| 25 | 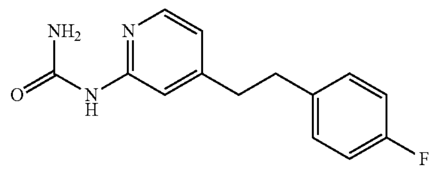 [SMILES: NC(=O)Nc1cc(CCc2ccc(F)cc2)ccn1] | {4-[2-(4-Fluoro-phenyl)-ethyl]-pyridin-2-yl}-urea |
| 26 | 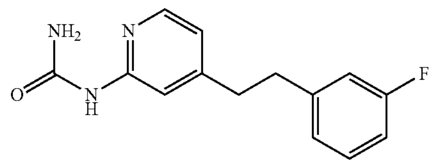 [SMILES: NC(=O)Nc1cc(CCc2cccc(F)c2)ccn1] | {4-[2-(3-Fluoro-phenyl)-ethyl]-pyridin-2-yl}-urea |
| 27 | 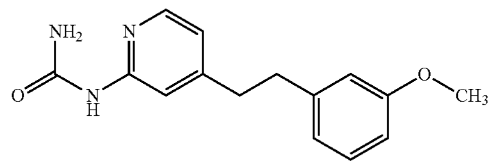 [SMILES: COc1cccc(CCc2ccnc(NC(N)=O)c2)c1] | {4-[2-(3-Methoxy-phenyl)-ethyl]-pyridin-2-yl}-urea |
| 28 | 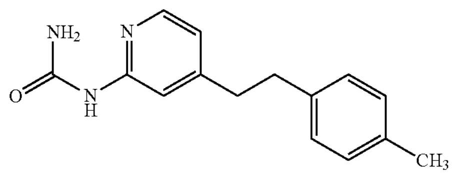 [SMILES: Cc1ccc(CCc2ccnc(NC(N)=O)c2)cc1] | [4-(2-p-Tolyl-ethyl)-pyridin-2-yl]-urea |
| 29 | 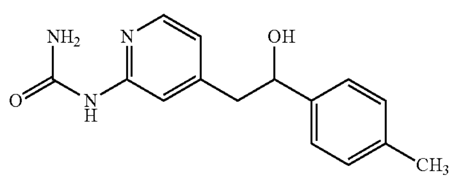 [SMILES: Cc1ccc(C(O)Cc2ccnc(NC(N)=O)c2)cc1] | [4-(2-Hydroxy-2-p-tolyl-ethyl)-pyridin-2-yl]-urea |
| 30 | 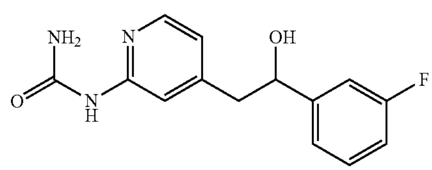 [SMILES: NC(=O)Nc1cc(CC(O)c2cccc(F)c2)ccn1] | {4-[2-(3-Fluoro-phenyl)-2-hydroxy-ethyl]-pyridin-2-yl}-urea |
| 31 | 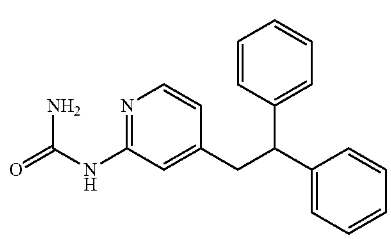 [SMILES: NC(=O)Nc1cc(CC(c2ccccc2)c2ccccc2)ccn1] | [4-(2,2-Diphenyl-ethyl)-pyridin-2-yl]-urea |
| 32 | 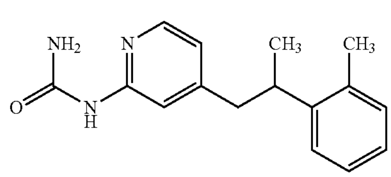 [SMILES: Cc1ccccc1C(C)Cc1ccnc(NC(N)=O)c1] | [4-(2-o-Tolyl-propyl)-pyridin-2-yl]-urea |

TABLE 1-continued

| Compound | Structure | Name |
|---|---|---|
| 33 | 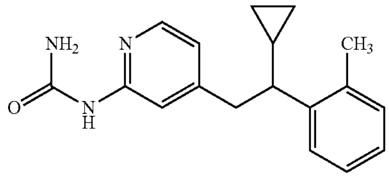 [SMILES: Cc1ccccc1C(Cc1ccnc(NC(N)=O)c1)C1CC1] | [4-(2-Cyclopropyl-2-o-tolyl-ethyl)-pyridin-2-yl]-urea |
| 34 | 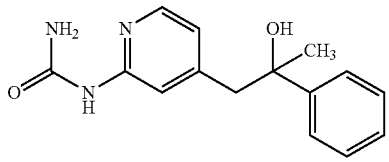 [SMILES: CC(O)(Cc1ccnc(NC(N)=O)c1)c1ccccc1] | [4-(2-Hydroxy-2-phenyl-propyl)-pyridin-2-yl]-urea |
| 35 | 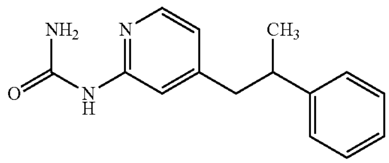 [SMILES: CC(Cc1ccnc(NC(N)=O)c1)c1ccccc1] | [4-(2-Phenyl-propyl)-pyridin-2-yl]-urea |
| 36 | 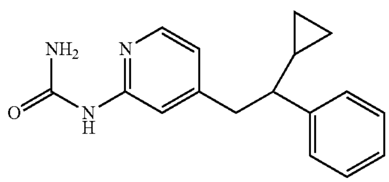 [SMILES: NC(=O)Nc1cc(CC(c2ccccc2)C2CC2)ccn1] | [4-(2-Cyclopropyl-2-phenyl-ethyl)-pyridin-2-yl]-urea |
| 37 | 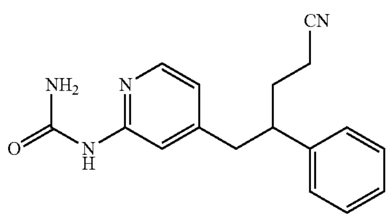 [SMILES: N#CCCC(Cc1ccnc(NC(N)=O)c1)c1ccccc1] | [4-(4-Cyano-2-phenyl-butyl)-pyridin-2-yl]-urea |
| 38 | 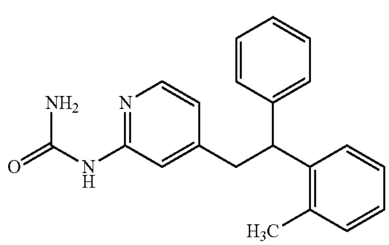 [SMILES: Cc1ccccc1C(Cc1ccnc(NC(N)=O)c1)c1ccccc1] | [4-(2-Phenyl-2-o-tolyl-ethyl)-pyridin-2-yl]-urea |
| 39 | 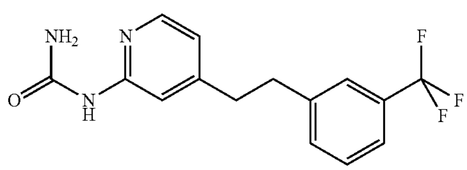 [SMILES: NC(=O)Nc1cc(CCc2cccc(C(F)(F)F)c2)ccn1] | {4-[2-(3-Trifluoromethyl-phenyl)-ethyl]-pyridin-2-yl}-urea |
| 40 | 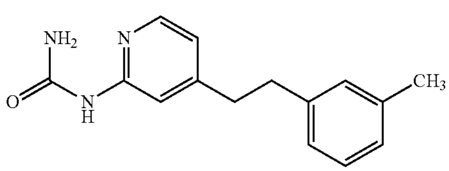 [SMILES: Cc1cccc(CCc2ccnc(NC(N)=O)c2)c1] | [4-(2-m-Tolyl-ethyl)-pyridin-2-yl]-urea |

TABLE 1-continued

| Compound | Structure | Name |
|---|---|---|
| 41 | 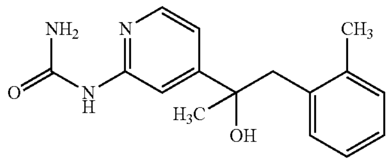 [SMILES: Cc1ccccc1CC(C)(O)c1ccnc(NC(N)=O)c1] | [4-(1-Hydroxy-1-methyl-2-o-tolyl-ethyl)-pyridin-2-yl]-urea |
| 42 | 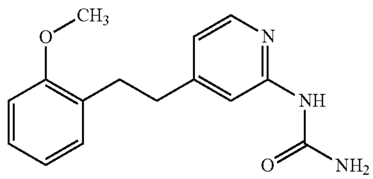 [SMILES: COc1ccccc1CCc1ccnc(NC(N)=O)c1] | {4-[2-(2-Methoxy-phenyl)-ethyl]-pyridin-2-yl}-urea |
| 43 | 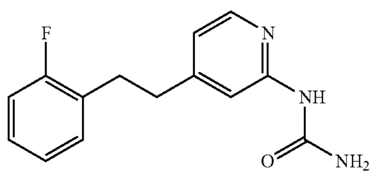 [SMILES: NC(=O)Nc1cc(CCc2ccccc2F)ccn1] | {4-[2-(2-Fluoro-phenyl)-ethyl]-pyridin-2-yl}-urea |
| 44 | 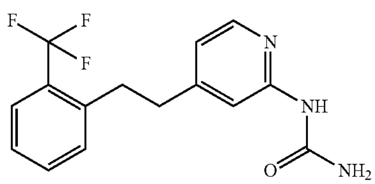 [SMILES: NC(=O)Nc1cc(CCc2ccccc2C(F)(F)F)ccn1] | {4-[2-(2-Trifluoromethyl-phenyl)-ethyl]-pyridin-2-yl}-urea |
| 45 | 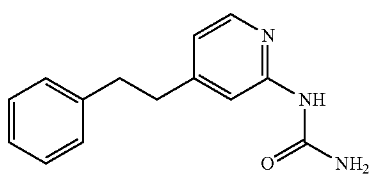 [SMILES: NC(=O)Nc1cc(CCc2ccccc2)ccn1] | (4-Phenethyl-pyridin-2-yl)-urea |
| 46 | 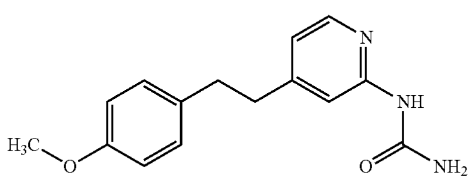 [SMILES: COc1ccc(CCc2ccnc(NC(N)=O)c2)cc1] | {4-[2-(4-Methoxy-phenyl)-ethyl]-pyridin-2-yl}-urea |
| 47 | 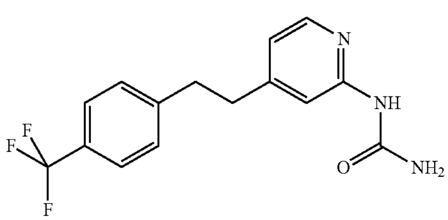 [SMILES: NC(=O)Nc1cc(CCc2ccc(C(F)(F)F)cc2)ccn1] | {4-[2-(4-Trifluoromethyl-phenyl)-ethyl]-pyridin-2-yl}-urea |
| 48 | 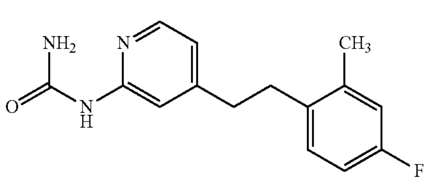 [SMILES: Cc1cc(F)ccc1CCc1ccnc(NC(N)=O)c1] | {4-[2-(4-Fluoro-2-methyl-phenyl)-ethyl]-pyridin-2-yl}-urea |

TABLE 1-continued

| Compound | Structure | Name |
|---|---|---|
| 49 | 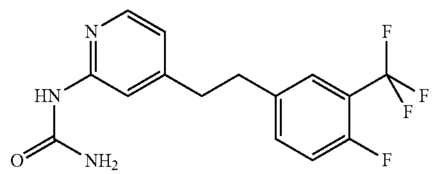 [SMILES: NC(=O)Nc1cc(CCc2ccc(F)c(C(F)(F)F)c2)ccn1] | {4-[2-(4-Fluoro-3-trifluoromethyl-phenyl)-ethyl]-pyridin-2-yl}-urea |
| 50 | 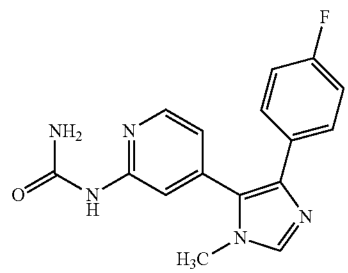 [SMILES: Cn1cnc(-c2ccc(F)cc2)c1-c1ccnc(NC(N)=O)c1] | {4-[5-(4-Fluoro-phenyl)-3-methyl-3H-imidazol-4-yl]-pyridin-2-yl}-urea |
| 51 | 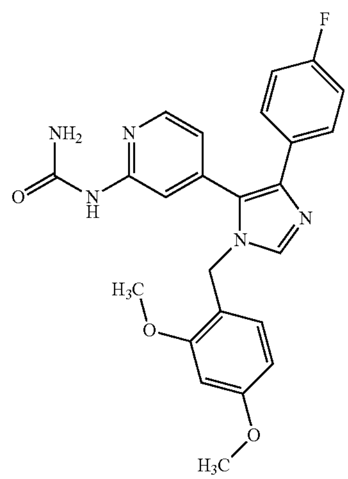 [SMILES: COc1ccc(Cn2cnc(-c3ccc(F)cc3)c2-c2ccnc(NC(N)=O)c2)c(OC)c1] | {4-[3-(2,4-Dimethoxy-benzyl)-5-(4-fluoro-phenyl)-3H-imidazol-4-yl]-pyridin-2-yl}-urea |
| 52 | 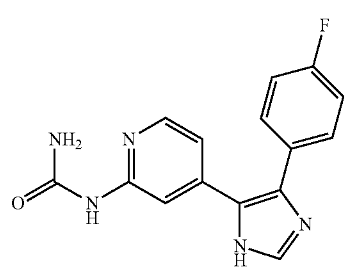 [SMILES: NC(=O)Nc1cc(-c2[nH]cnc2-c2ccc(F)cc2)ccn1] | {4-[5-(4-Fluoro-phenyl)-3H-imidazol-4-yl]-pyridin-2-yl}-urea |
| 53 | 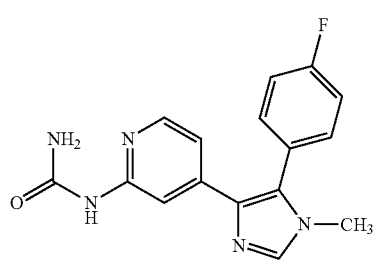 [SMILES: Cn1cnc(-c2ccnc(NC(N)=O)c2)c1-c1ccc(F)cc1] | {4-[5-(4-Fluoro-phenyl)-1-methyl-1H-imidazol-4-yl]-pyridin-2-yl}-urea |

TABLE 1-continued

| Compound | Structure | Name |
|---|---|---|
| 54 | 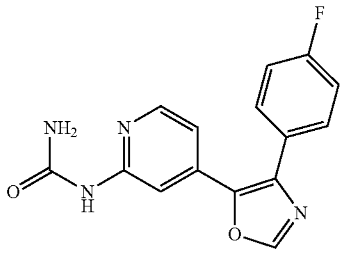 [SMILES: NC(=O)Nc1cc(-c2ocnc2-c2ccc(F)cc2)ccn1] | {4-[4-(4-Fluoro-phenyl)-oxazol-5-yl]-pyridin-2-yl}-urea |
| 55 | 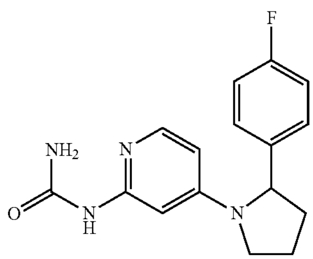 [SMILES: NC(=O)Nc1cc(N2CCCC2c2ccc(F)cc2)ccn1] | {4-[2-(4-Fluoro-phenyl)-pyrrolidin-1-yl]-pyridin-2-yl}-urea |
| 56 | 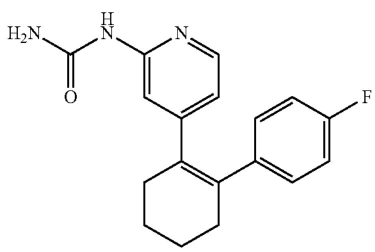 [SMILES: NC(=O)Nc1cc(C2=C(c3ccc(F)cc3)CCCC2)ccn1] | {4-[2-(4-Fluoro-phenyl)-cyclohex-1-enyl]-pyridin-2-yl}-urea |
| 57 | 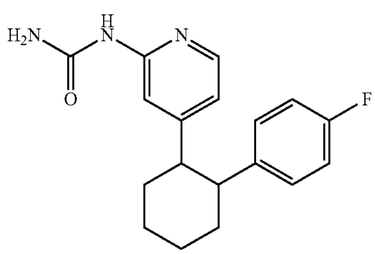 [SMILES: NC(=O)Nc1cc(C2CCCCC2c2ccc(F)cc2)ccn1] | {4-[2-(4-Fluoro-phenyl)-cyclohexyl]-pyridin-2-yl}-urea |

The compounds of formula I may be made using the general synthetic methods described below, which also constitute part of the invention.

General Synthetic Methods

In the general synthetic schemes described below, $R^1$, $R^2$, $R^3$, $R^4$, $R^5$, $R^6$, $R^7$, $R^8$, $R^9$, $R^{10}$ and M have the meanings given above, in the absence of a statement to the contrary; X is independently selected from Cl, Br and I.

Starting materials and intermediates used in the methods below are either commercially available or easily prepared from commercially available materials by those skilled in the art.

Compounds of formula (I), wherein $R^4$ is a group of formula (II), can be synthesized using the methods illustrated by Schemes 1 and 2.

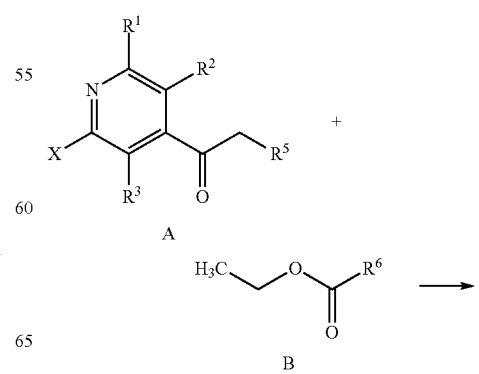

Scheme 1

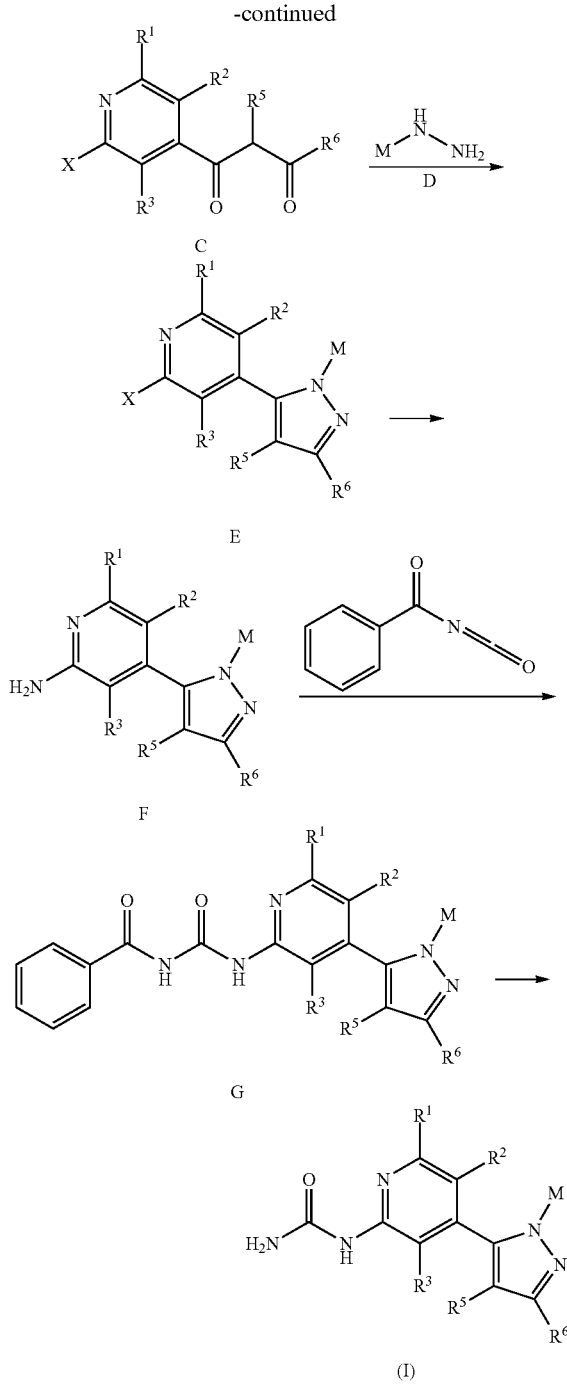

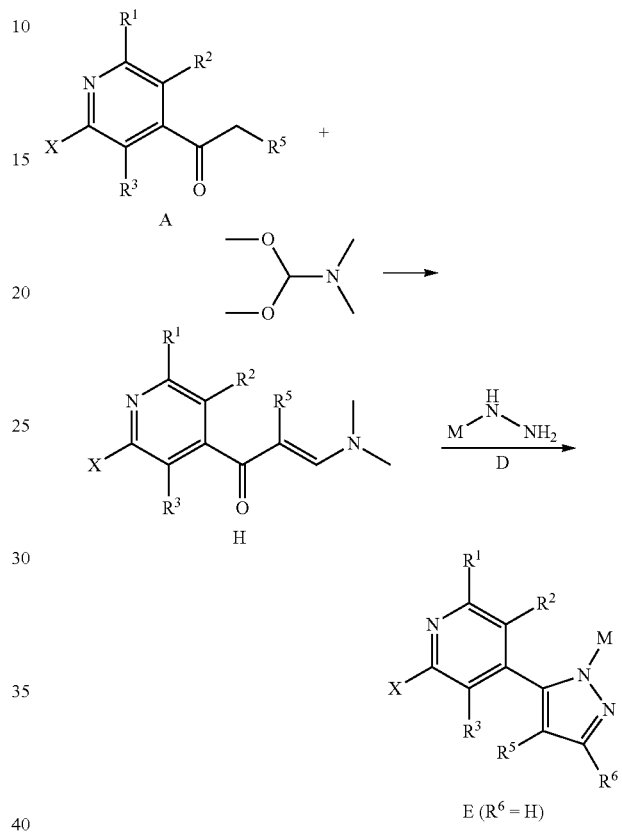

Method 1:

As illustrated in scheme 1, reaction of a ketone of formula A with an ester of formula B, in a suitable solvent, in the presence of a suitable base, provides a condensed product of formula C. Reaction of the di-ketone of formula C with a hydrazine of formula D, in a suitable solvent, at a suitable temperature, provides the pyrazole compound of formula E. Reaction of the pyrazole compound of formula E with a suitable amino group (—NH$_2$) surrogates, for examples ammonium hydroxide or lithium hexamethyldisilazide, in a suitable solvent, with or without a suitable catalyst, provides the amino pyridine compound of formula F. Reaction of amino pyridine of formula F with benzoyl isocyanate, in a suitable solvent, at a suitable temperature, provides the compound of formula G. Final deprotection of the compound of formula G using potassium carbonate, in a suitable solvent, at a suitable temperature, affords the compound of the invention.

Method 2:

Compounds of formula (I), wherein R$^4$ is a group of formula (II) and R$^6$ is H, may also be synthesized by the method outlined in Scheme 2.

As shown in scheme 2, reaction of a ketone of formula A with n,n-dimethylformamide dimethyl acetal, in a suitable solvent, at a suitable temperature, provides the compound of formula H. Reaction of the compound H with a hydrazine of formula D, in a suitable solvent, at a suitable temperature, affords the pyrazole compound of formula E. The pyrazole of formula E may be converted to the compound of the invention by the sequence shown in scheme 1.

Compounds of formula (I), wherein R$^4$ is a group of formula (III) or formula (IV), can be synthesized using the methods described in Scheme 3 and 4.

Scheme 3

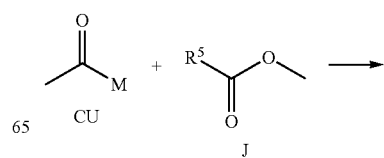

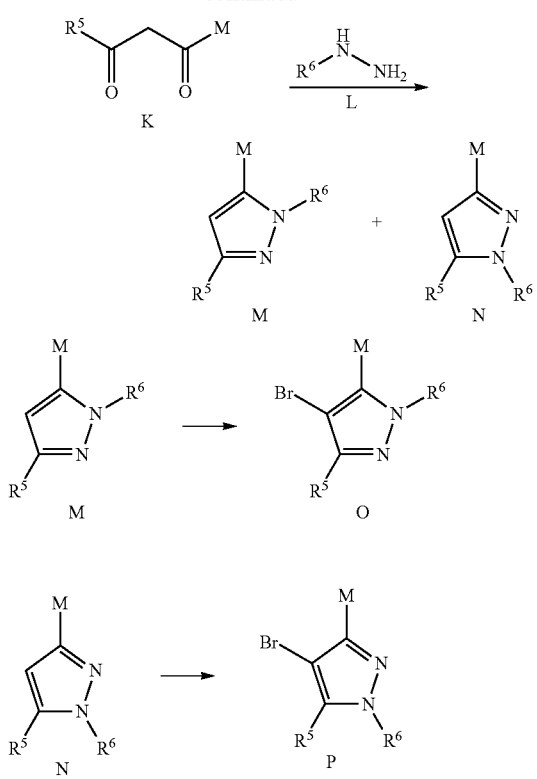

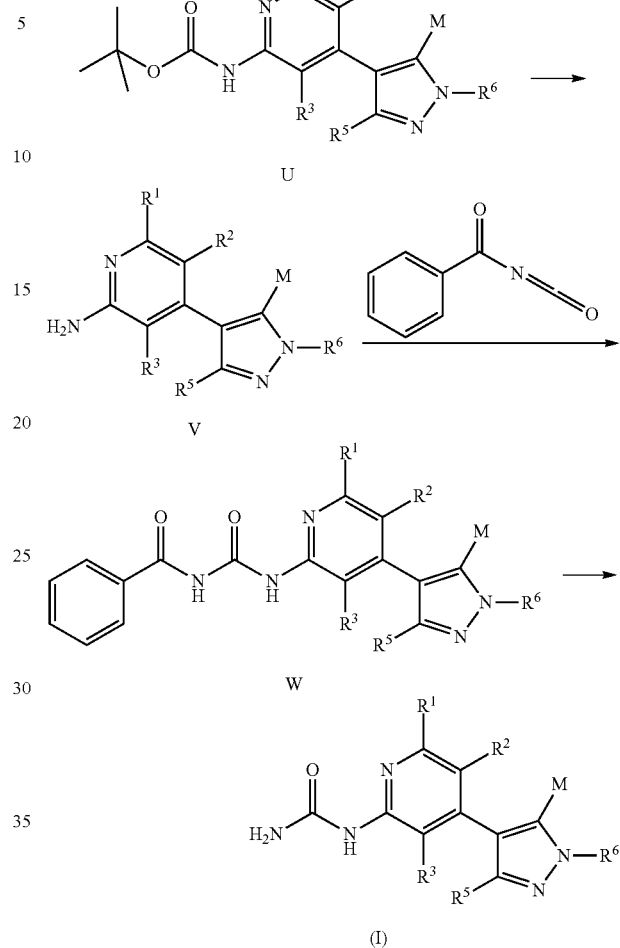

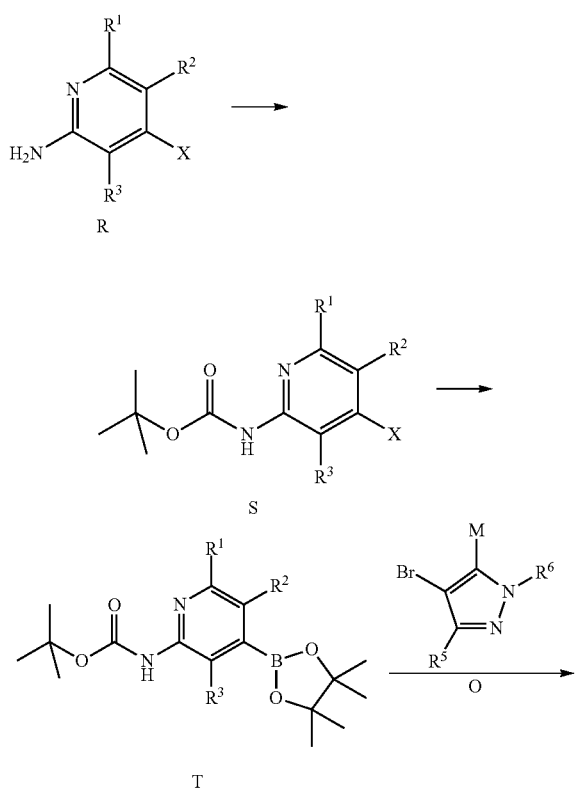

As illustrated in Scheme 3, reaction of a ketone of formula CU with an ester of formula J, in a suitable solvent, in the presence of a suitable base, provides the condensed product of formula K. Reaction of the di-ketone of formula K with a hydrazine of formula L, in a suitable solvent, at a suitable temperature, provides the pyrazole compound of formula M and N which are separated from each other. Standard bromnation of the pyrazole compound of formula M and N with a brominating agent, for example N-bromosuccinimide, in a suitable solvent, provides the compounds of formula O and P.

As illustrated in Scheme 4, standard protection of the amino group with the tert-butoxycarbonyl group provides compound of formula S. Reaction of the compound of formula S with pinacol diborane in a suitable solvent, at a suitable temperature, in the presence of a suitable catalyst, provides the compound of formula T. Standard Suzuki coupling reaction between compound T and compound O, in a suitable solvent, in the presence of a suitable catalyst, provides the compound of formula U. Standard removal of the tert-butoxycarbonyl protecting group, in a suitable solvent, with a suitable acid affords amino pyridine compound of formula V. Reaction of the amino pyridine of formula V with benzoyl isocyanate, in a suitable solvent, at a suitable temperature, provides the compound of formula W. Final deprotection of the compound of formula W using potassium carbonate, in a suitable solvent, at a suitable temperature, affords the compound of the invention.

The pyrazole regio isomer of formula P may be converted to the compound of the invention by the sequence shown in scheme 4.

Compounds of formula (I), wherein $R^4$ is a group of formula (V) or formula (VI), can be synthesized using the methods described in Scheme 5.

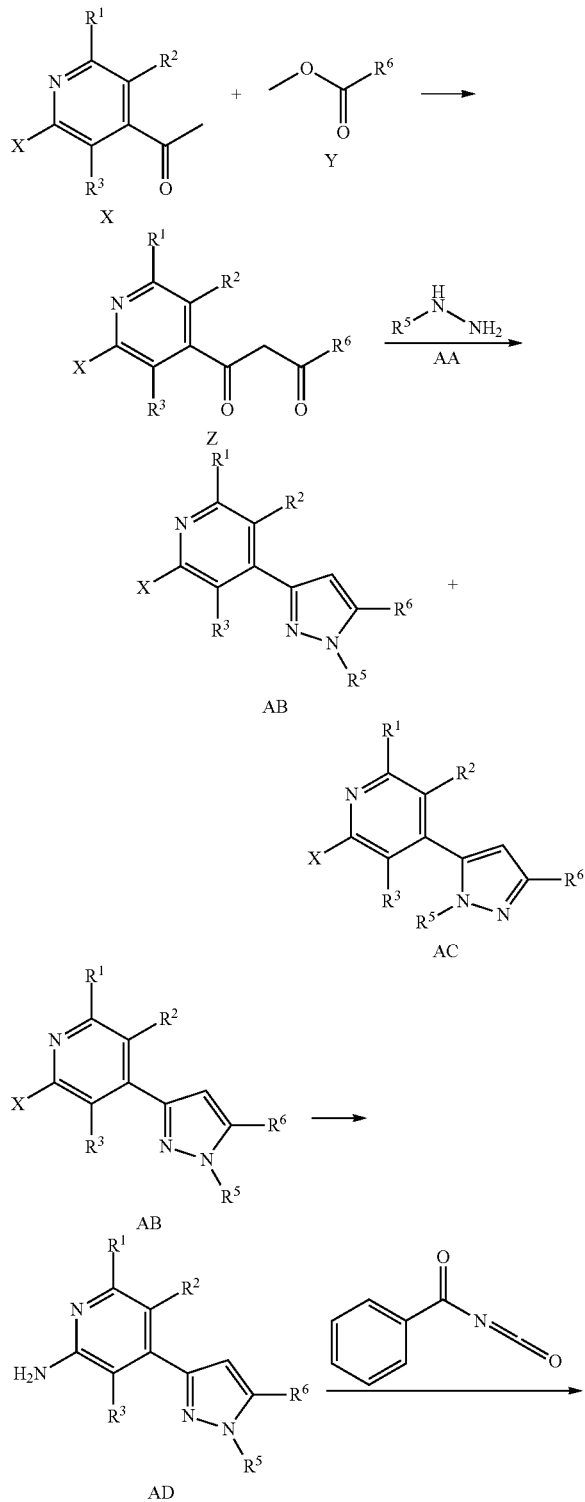

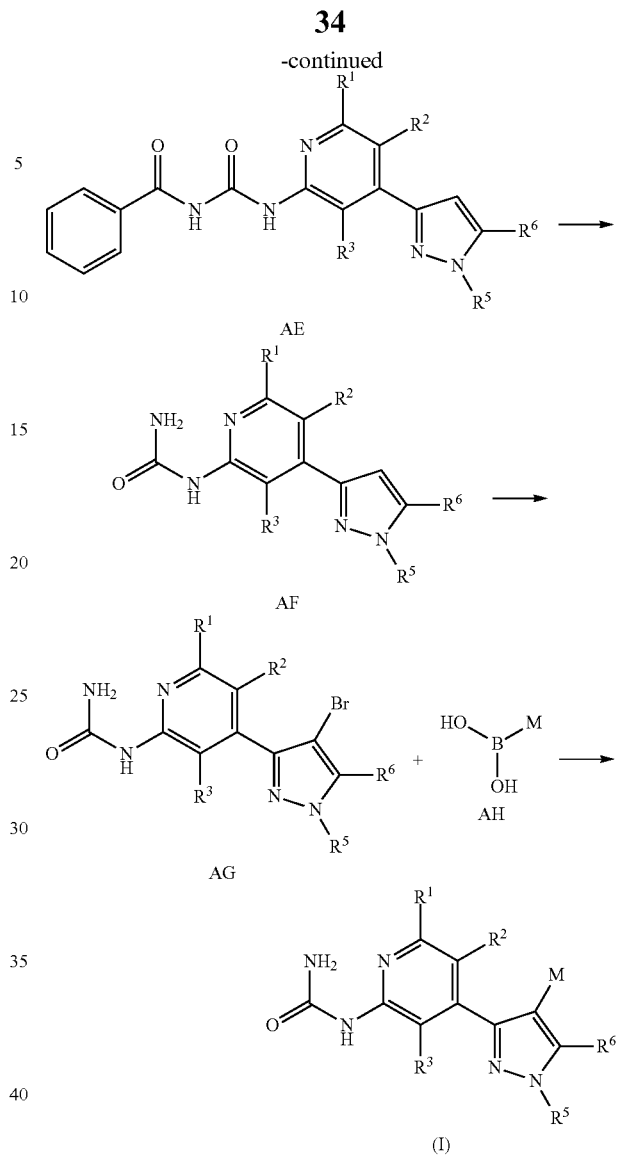

As illustrated in Scheme 5, reaction of a ketone of formula X with an ester of formula Y, in a suitable solvent, in the presence of a suitable base, provides the condensed product of formula Z. Reaction of the di-ketone of formula Z with a hydrazine of formula AA, in a suitable solvent, at a suitable temperature, provides the pyrazole compound of formula AB and AC which are separated from each other. Reaction of the pyridine compound of formula AB with a suitable amino group (—$NH_2$) surrogates, for examples ammonium hydroxide or lithium hexamethyldisilazide, in a suitable solvent with or without a suitable catalyst provides the amino pyridine compound of formula AD. Reaction of the amino pyridine of formula AD with benzoyl isocyanate, in a suitable solvent, at a suitable temperature, provides the compound of formula AE. Deprotection of the compound of formula AE using potassium carbonate, in a suitable solvent, at a suitable temperature, affords the compound of formula AF. Standard bromination of the pyrazole compound of formula AF using a brominating agent, for example N-bromosuccinimide, in a suitable solvent, provides the compounds of formula AG. Coupling reaction between the compound of formula AG and the compound of formula AH or its equivalent boronic ester, in a suitable solvent, at a suitable temperature, in the presence of a suitable catalyst, affords the compound of the invention.

The pyrazole regio isomer of formula AC may be converted to the compound of the invention by the same sequence which converts the compound of formula AB to the compound of the invention as shown in Scheme 5.

Compounds of formula (I), wherein $R^4$ is a group of formula (VII), can be synthesized using the methods described in Scheme 6.

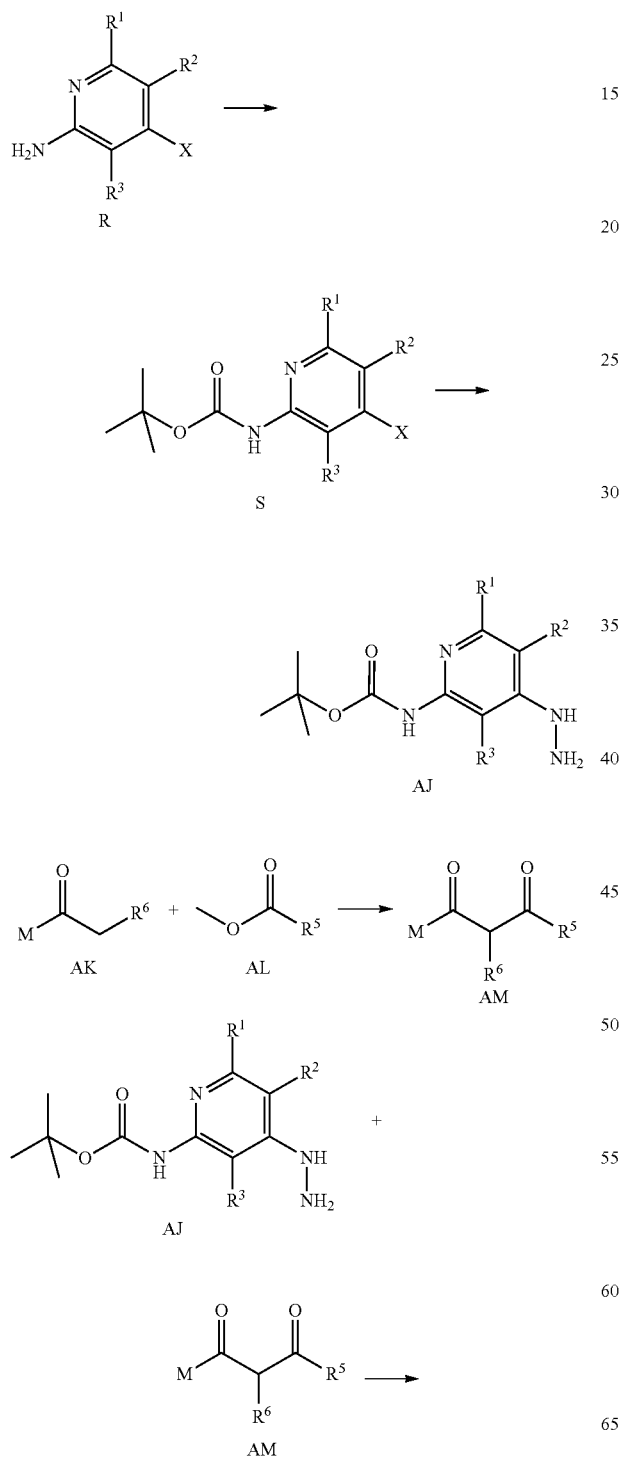

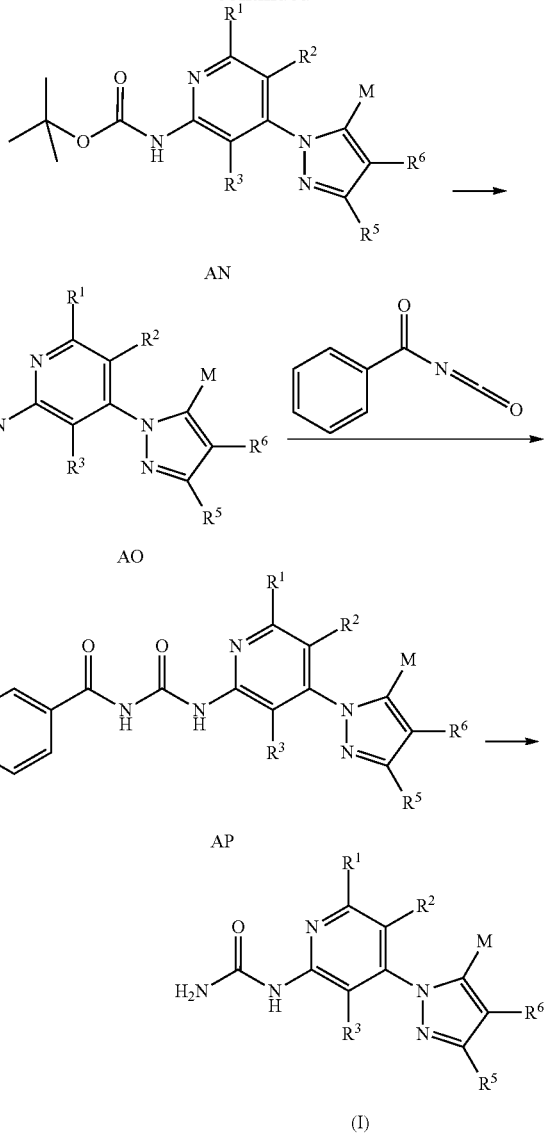

As illustrated in Scheme 6, standard protection of an amino pyridine compound of formula R with the tert-butoxycarbonyl group provides the compound of formula S. Reaction of the pyridine compound of formula S with hydrazine, in a suitable solvent, at a suitable temperature, provides the pyridine hydrazine compound of formula AJ. Reaction of a ketone of formula AK with an ester of formula AL, in a suitable solvent, in the presence of a suitable base, provides the condensed product of formula AM. Cyclization reaction between the compound of formula AJ and the compound of formula AM, in a suitable solvent, at a suitable temperature, provides the pyrazole compound of formula AN. Standard removal of the tert-butoxycarbonyl protecting group, in a suitable solvent, with a suitable acid affords the amino pyridine compound of formula AO. Reaction of the amino pyridine of formula AO with benzoyl isocyanate, in a suitable solvent, at a suitable temperature, provides the compound of formula AP. Deprotection of the compound of formula AP using potassium carbonate, in a suitable solvent, at a suitable temperature, affords the compound of the invention.

Compounds of formula (I), wherein $R^4$ is a group of formula (VIII), can be synthesized using the methods described in Scheme 7 to Scheme 10.

Scheme 7

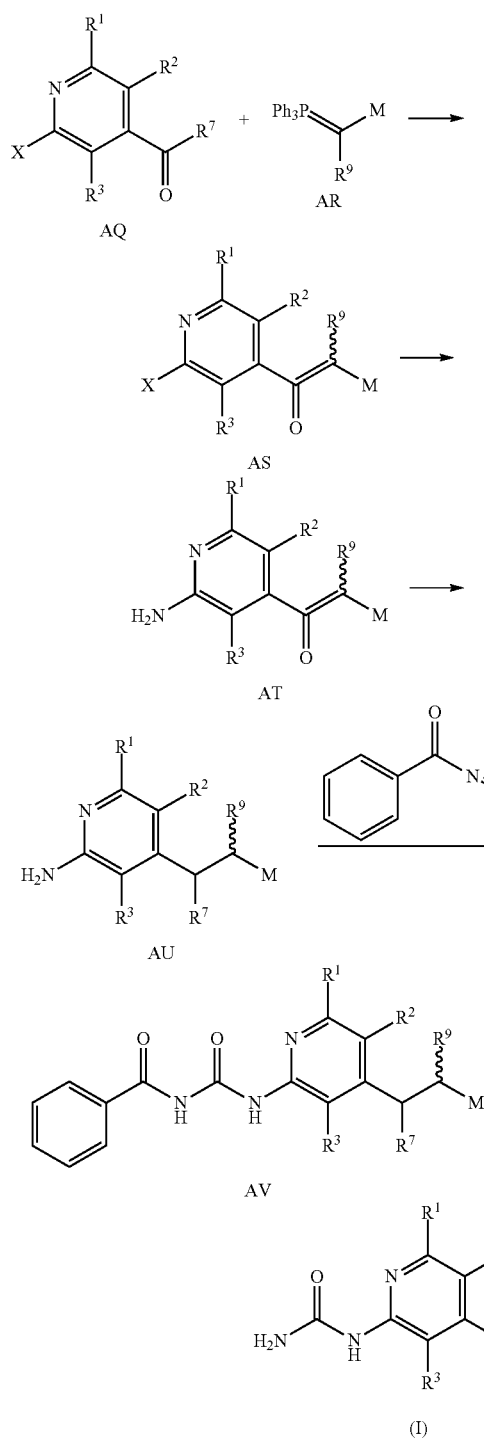

carbon, affords amino pyridine AU. Reaction of amino pyridine AU with benzoyl isocyanate, in a suitable solvent, at a suitable temperature, provides the compound of formula AV. Final deprotection of the compound of formula AV using potassium carbonate, in a suitable solvent, at a suitable temperature, affords the compound of formula (I), wherein both $R^8$ and $R^{10}$ are H.

Scheme 8A

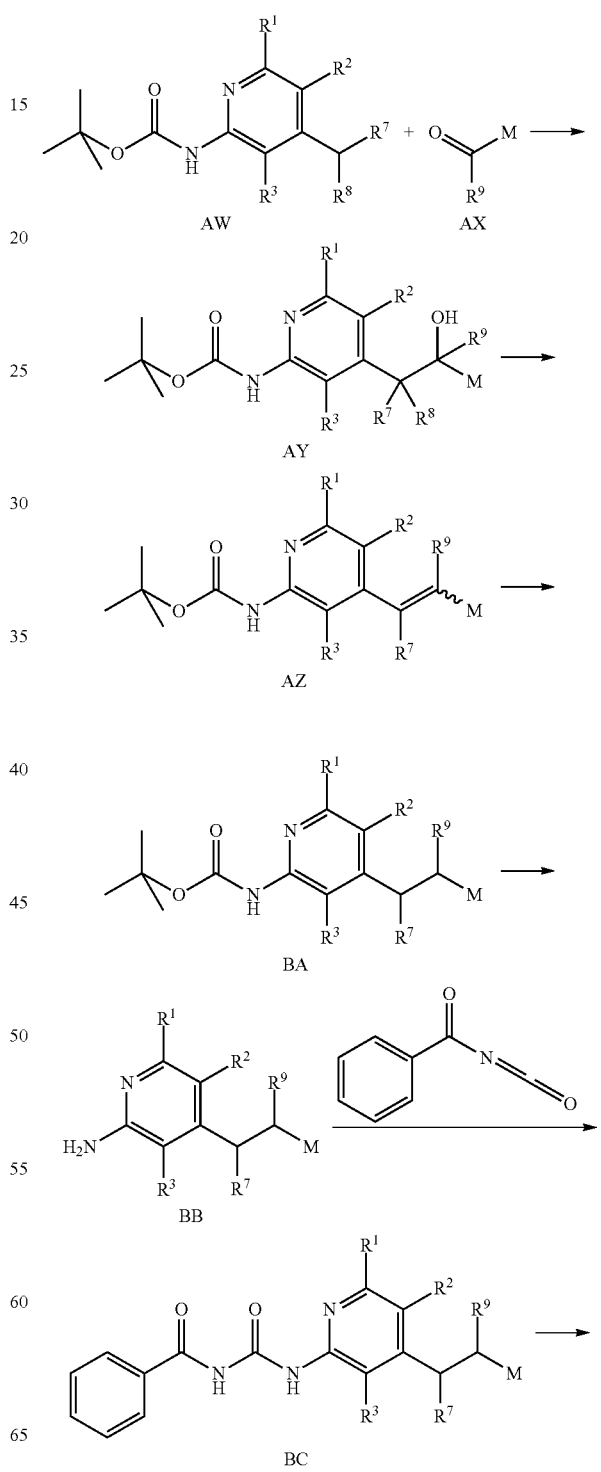

As illustrated in Scheme 7, Wittig olefination between keto AQ and ylide AR, in a suitable solvent, at a suitable temperature, provides compound AS. Reaction of the halide AS with a suitable amino group (—NH$_2$) surrogates, for examples ammonium hydroxide or lithium hexamethyldisilazide, in a suitable solvent, at a suitable temperature, with or without a suitable catalyst, provides the compound of formula AT. Hydrogenation of olefin AT using hydrogen gas, in a suitable solvent, with a suitable catalyst such as 10% Pd on activated

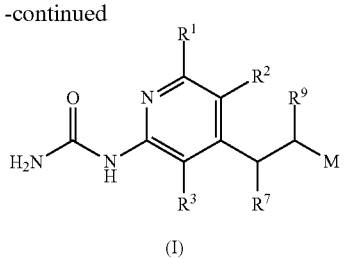

at a suitable temperature, affords the compound of formula (I), wherein both $R^8$ and $R^{10}$ are H.

As illustrated in Scheme 8B, removal of the BOC group of alcohol AY using proper acid such as trifluoroacetic acid, in a suitable solvent, at a suitable temperature, affords amino pyridine BD. Reaction of amino pyridine BD with benzoyl isocyanate, in a suitable solvent, at a suitable temperature, provides the compound of formula BE. Final deprotection of the compound of formula BE using potassium carbonate, in a suitable solvent, at a suitable temperature, affords the compound of formula (I), wherein $R^{10}$ is a —OH group.

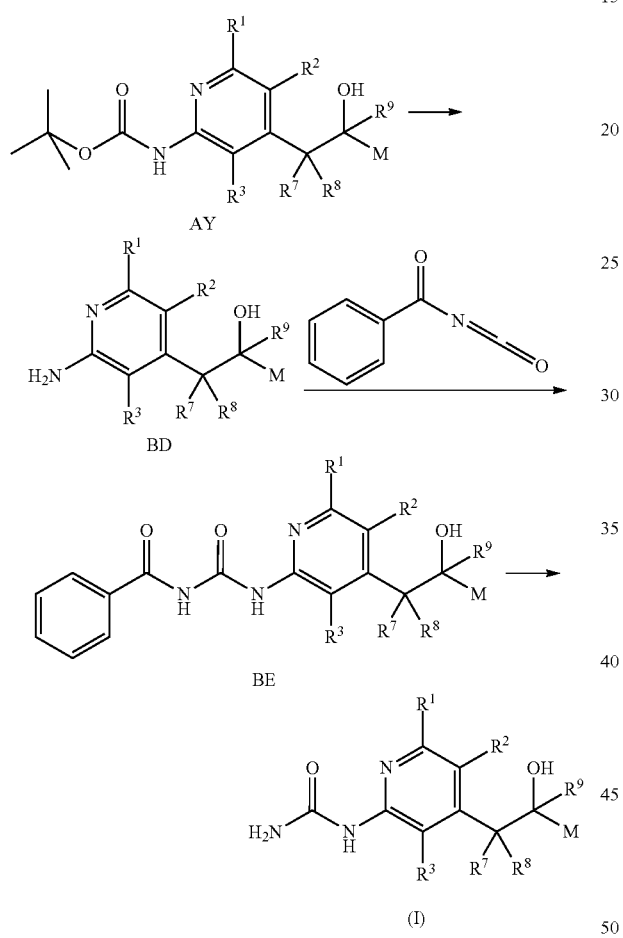

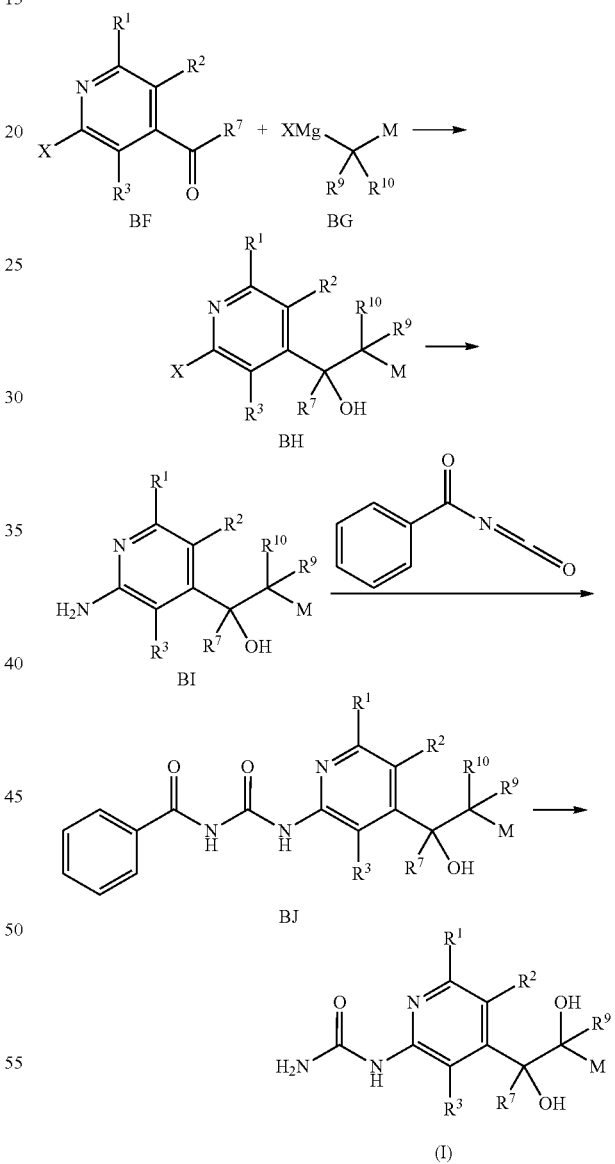

As illustrated in Scheme 8A, the anion which is generated by treating compound AW with suitable base such as n-BuLi, in a suitable solvent, at a suitable temperature, reacts with keto AX to give alcohol AY. Dehydration of compound AY using suitable dehydrating reagents such as $SOCl_2$ in pyridine or trifluoroacetic acid provides olefin AZ. Hydrogenation of olefin AZ using hydrogen gas, in a suitable solvent, with a suitable catalyst such as 10% Pd on activated carbon, affords compound BA. Removal of the BOC group of intermediate BA using proper acid such as trifluoroacetic acid, in a suitable solvent, at a suitable temperature, affords amino pyridine BB. Reaction of amino pyridine BB with benzoyl isocyanate, in a suitable solvent, at a suitable temperature, provides the compound of formula BC. Final deprotection of the compound of formula BC using potassium carbonate, in a suitable solvent, As illustrated in Scheme 9, keto BF reacts with Grignard reagent BG, in a suitable solvent, at a suitable temperature, to give alcohol BH. Reaction of compound BH with a suitable amino group (—$NH_2$) surrogates, for examples ammonium hydroxide or lithium hexamethyldisilazide, in a suitable solvent, at a suitable temperature, with or without a suitable catalyst, provides the compound of formula BI. Reaction of amino pyridine BI with benzoyl isocyanate, in a suitable solvent, at a suitable temperature, provides the compound of formula BJ. Final deprotection of the compound of formula BJ using potassium carbonate, in a suitable solvent, at a suitable temperature, affords the compound of formula (I), wherein $R^8$ is a —OH group.

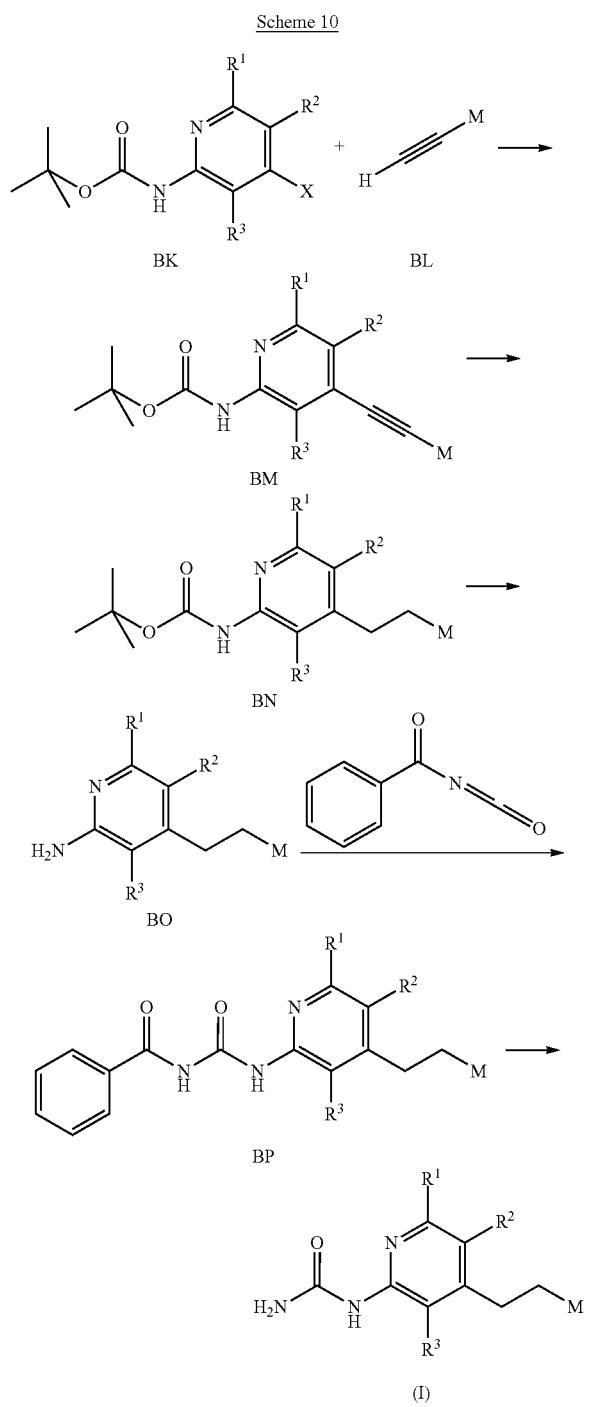

As illustrated in Scheme 10, Sonogashira coupling between halide BK and alkyne BL using suitable catalysts such as $Pd(PPh_3)_2Cl_2$ and CuI, in a suitable solvent, at a suitable temperature, provides compound BM. Hydrogenation of alkyne BM using hydrogen gas, in a suitable solvent, with a suitable catalyst such as 10% Pd on activated carbon, affords intermediate BN. Removal of the BOC group of intermediate BN using proper acid such as trifluoroacetic acid, in a suitable solvent, at a suitable temperature, affords amino pyridine BO. Reaction of compound BO with benzoyl isocyanate, in a suitable solvent, at a suitable temperature, provides the compound of formula BP. Final deprotection of the compound of formula BP using potassium carbonate, in a suitable solvent, at a suitable temperature, affords the compound of formula (I), wherein $R^7$, $R^8$ $R^9$ and $R^{10}$ are H.

Compounds of formula (I), wherein $R^4$ is a group of formula (IX), can be synthesized using the method described in Scheme 11.

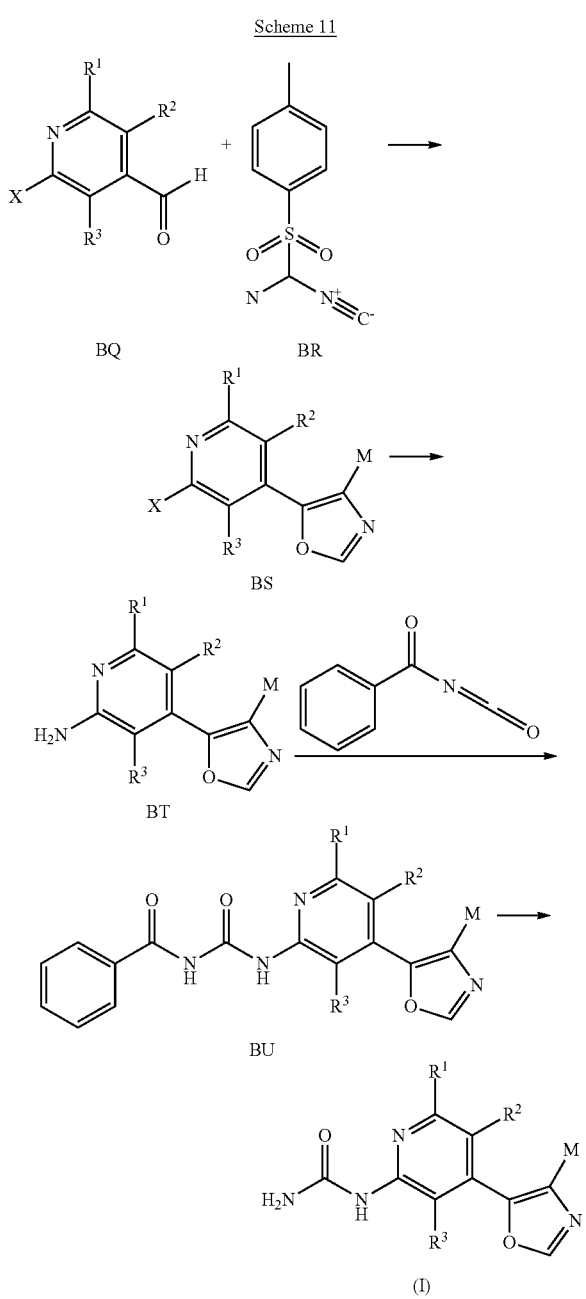

As illustrated in Scheme 11, cyclization between aldehyde BQ and tosylmethyl isocyanide BR in the presence of a suitable base such as aqueous ammonium hydroxide, in a suitable solvent, at a suitable temperature, provides compound BS. Reaction of compound BS with a suitable amino group (—NH$_2$) surrogates, for examples ammonium hydroxide or lithium hexamethyldisilazide, in a suitable solvent, at a suitable temperature, with or without a suitable catalyst, provides the amino pyridine BT. Reaction of compound BT with benzoyl isocyanate, in a suitable solvent, at a suitable temperature, provides the compound of formula BU. Final deprotection of the compound of formula BU using potassium carbonate, in a suitable solvent, at a suitable temperature, affords the compound of formula (I).

Compounds of formula (I), wherein R$^4$ is a group of formula (X), can be synthesized using the method described in Scheme 12.

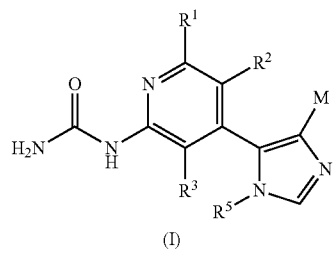

As illustrated in Scheme 12, cyclozation between aldehyde BQ, amine BV and tosylmethyl isocyanide BR in the presence of a suitable base such as piperazine, in a suitable solvent, at a suitable temperature, provides compound BW. Reaction of compound BW with a suitable amino group (—NH$_2$) surrogates, for examples ammonium hydroxide or lithium hexamethyldisilazide, in a suitable solvent, at a suitable temperature, with or without a suitable catalyst, provides the amino pyridine BX. Reaction of compound BX with benzoyl isocyanate, in a suitable solvent, at a suitable temperature, provides the compound of formula BY. Final deprotection of the compound of formula BY using potassium carbonate, in a suitable solvent, at a suitable temperature, affords the compound of formula (I).

Compounds of formula (I), wherein R$^4$ is a group of formula (XI), can be synthesized using the method described in the Scheme 13.

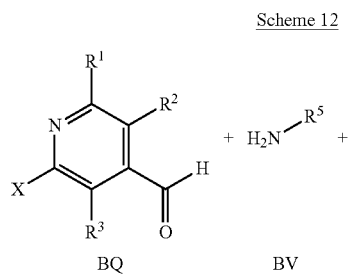

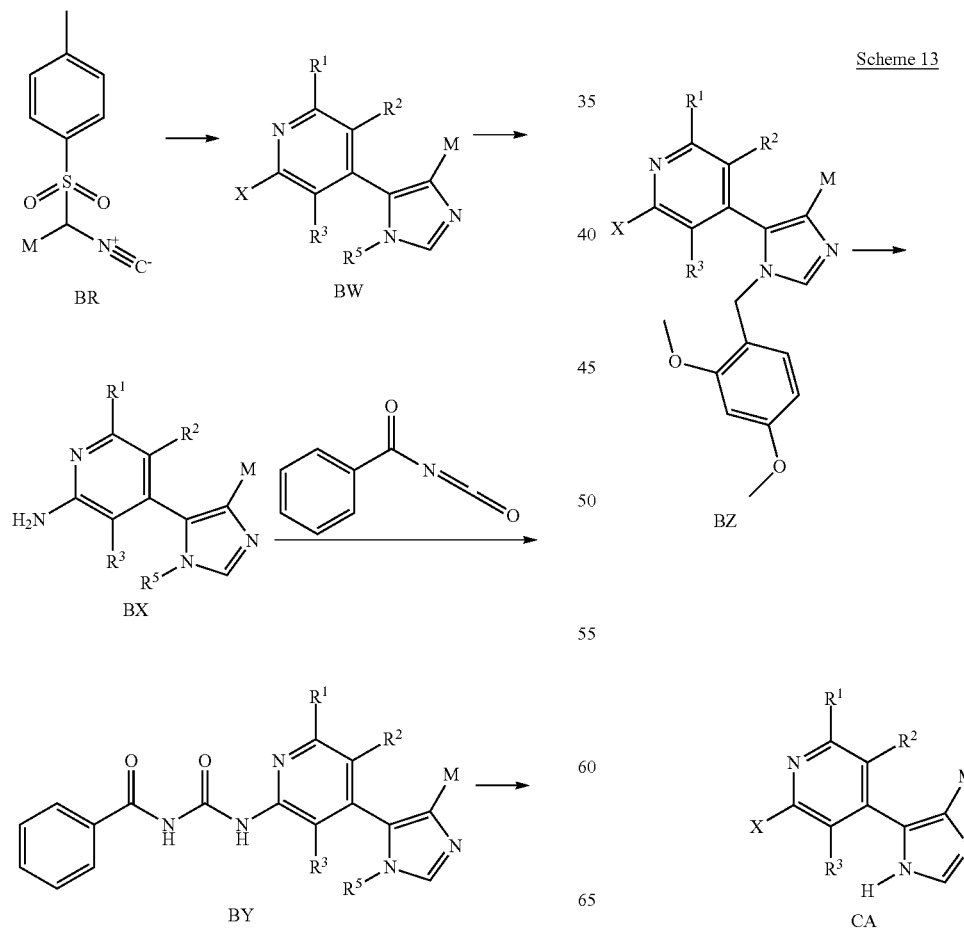

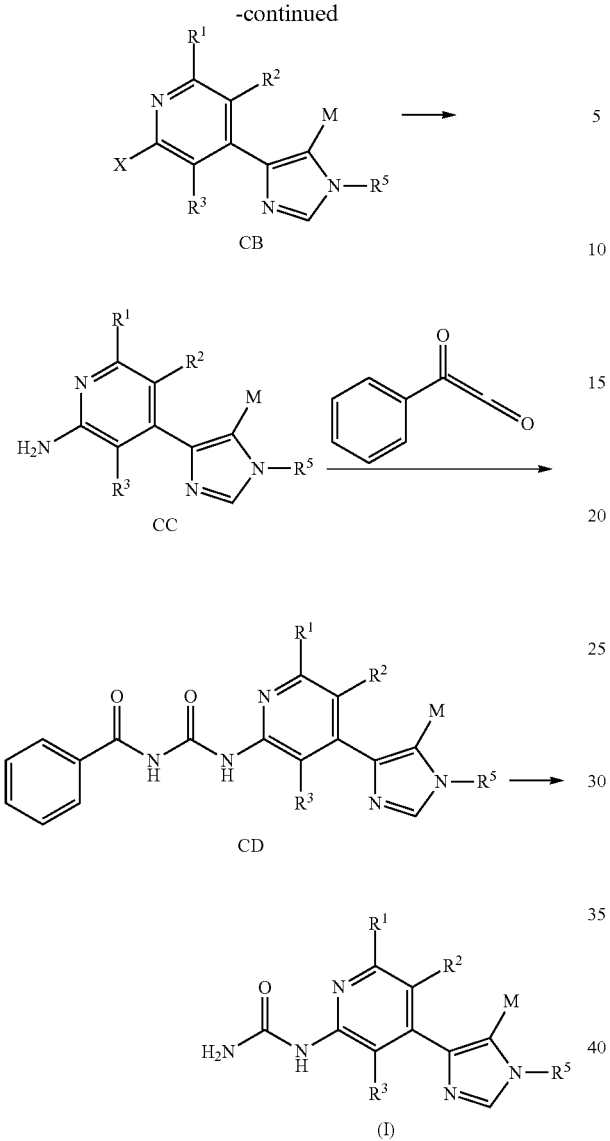

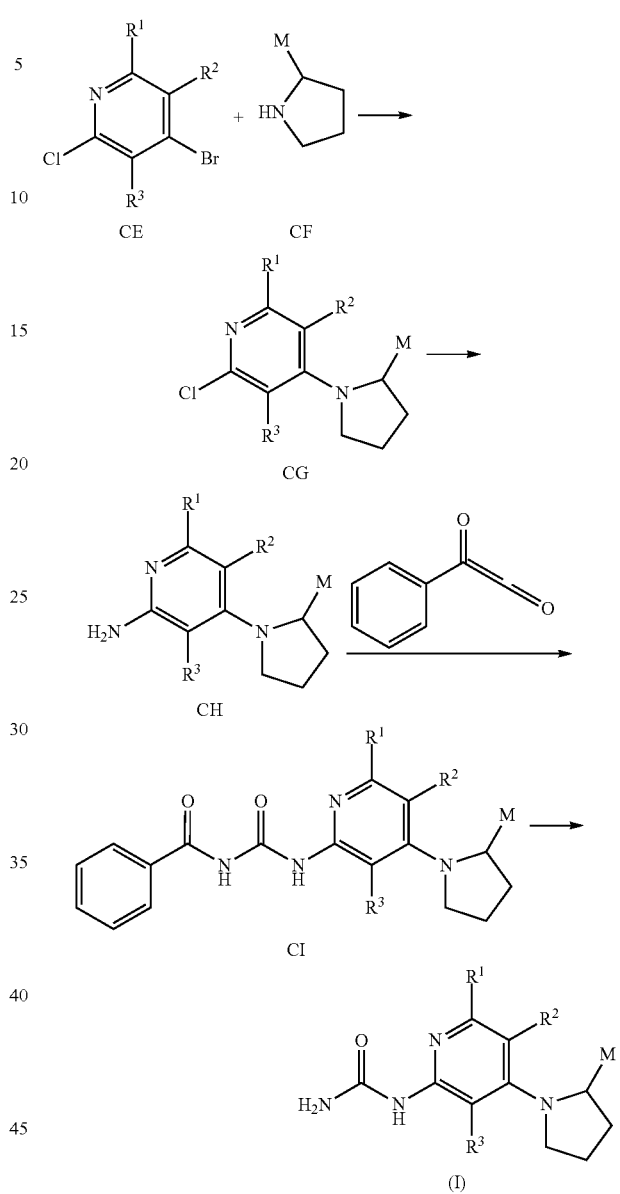

Scheme 14

As illustrated in Scheme 13, deprotection of compound BZ, which is prepared using the method described in Scheme 12, by using a suitable acid such as trifluoroacetic acid, in a suitable solvent, at a suitable temperature, affords imidazole CA. Nuclephilic replacement between the imidazole CA and an electrophilic $R^5$ such as the methyl iodide in the presence of a base such as sodium hydride, in a suitable solvent, at a suitable temperature, provides compound CB. Reaction of compound CB with a suitable amino group (—$NH_2$) surrogates, for examples ammonium hydroxide or lithium hexamethyldisilazide, in a suitable solvent, at a suitable temperature, with or without a suitable catalyst, provides the amino pyridine CC. Reaction of compound CC with benzoyl isocyanate, in a suitable solvent, at a suitable temperature, provides the compound of formula CD. Final deprotection of the compound of formula CD using potassium carbonate, in a suitable solvent, at a suitable temperature, affords the compound of formula (I).

Compounds of formula (I), wherein $R^4$ is a group of formula (XII), can be synthesized using the method described in Scheme 14.

As illustrated in Scheme 14, Nuclephilic replacement between di-halide CE and pyrrolidine CF in the presence of a suitable such as triethylamine, in a suitable solvent, at a suitable temperature, affords compound CG. Reaction of compound CG with a suitable amino group (—$NH_2$) surrogates, for examples ammonium hydroxide or lithium hexamethyldisilazide, in a suitable solvent, at a suitable temperature, with or without a suitable catalyst, provides the amino pyridine CH. Reaction of compound CH with benzoyl isocyanate, in a suitable solvent, at a suitable temperature, provides the compound of formula CI. Final deprotection of the compound of formula CI using potassium carbonate, in a suitable solvent, at a suitable temperature, affords the compound of formula (I).

Compounds of formula (I), wherein $R^4$ is a group of formula (XIII), can be synthesized using the method described in Scheme 15.

Scheme 15

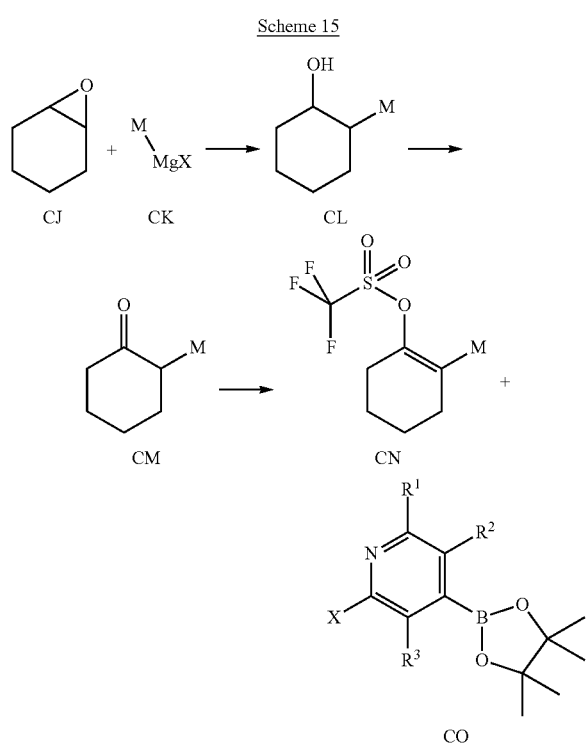

As illustrated in Scheme 15, Nuclephilic opening of epoxide CJ using Grignard CK, in a suitable solvent, at a suitable temperature, affords alcohol CL. Oxidation of CL using a suitable oxidizing condition such as Swern oxidation, in a suitable solvent, at a suitable temperature, provides keto CM. Reaction of CM with a base such as sodium hydride and a triflating agent such as 1,1,1-trifluoro-N-phenyl-N-(trifluoromethylsulfonyl)methanesulfonamide, in a suitable solvent, at a suitable temperature, affords triflate CN. Suzuki coupling reaction between triflate CN and boronic ester CO in the presence of a suitable catalyst such as $Pd(PPh_3)_2Cl_2$, in a suitable solvent, at a suitable temperature, provides the compound of formula CP. Reaction of compound CP with a suitable amino group ($-NH_2$) surrogates, for examples ammonium hydroxide or lithium hexamethyldisilazide, in a suitable solvent, at a suitable temperature, with or without a suitable catalyst, provides the amino pyridine CQ. Reaction of compound CQ with benzoyl isocyanate, in a suitable solvent, at a suitable temperature, provides the compound of formula CR. Final deprotection of the compound of formula CR using potassium carbonate, in a suitable solvent, at a suitable temperature, affords the compound of formula (I).

Compounds of formula (I), wherein $R^4$ is a group of formula (XIV), can be synthesized using the method described in Scheme 16.

Scheme 16

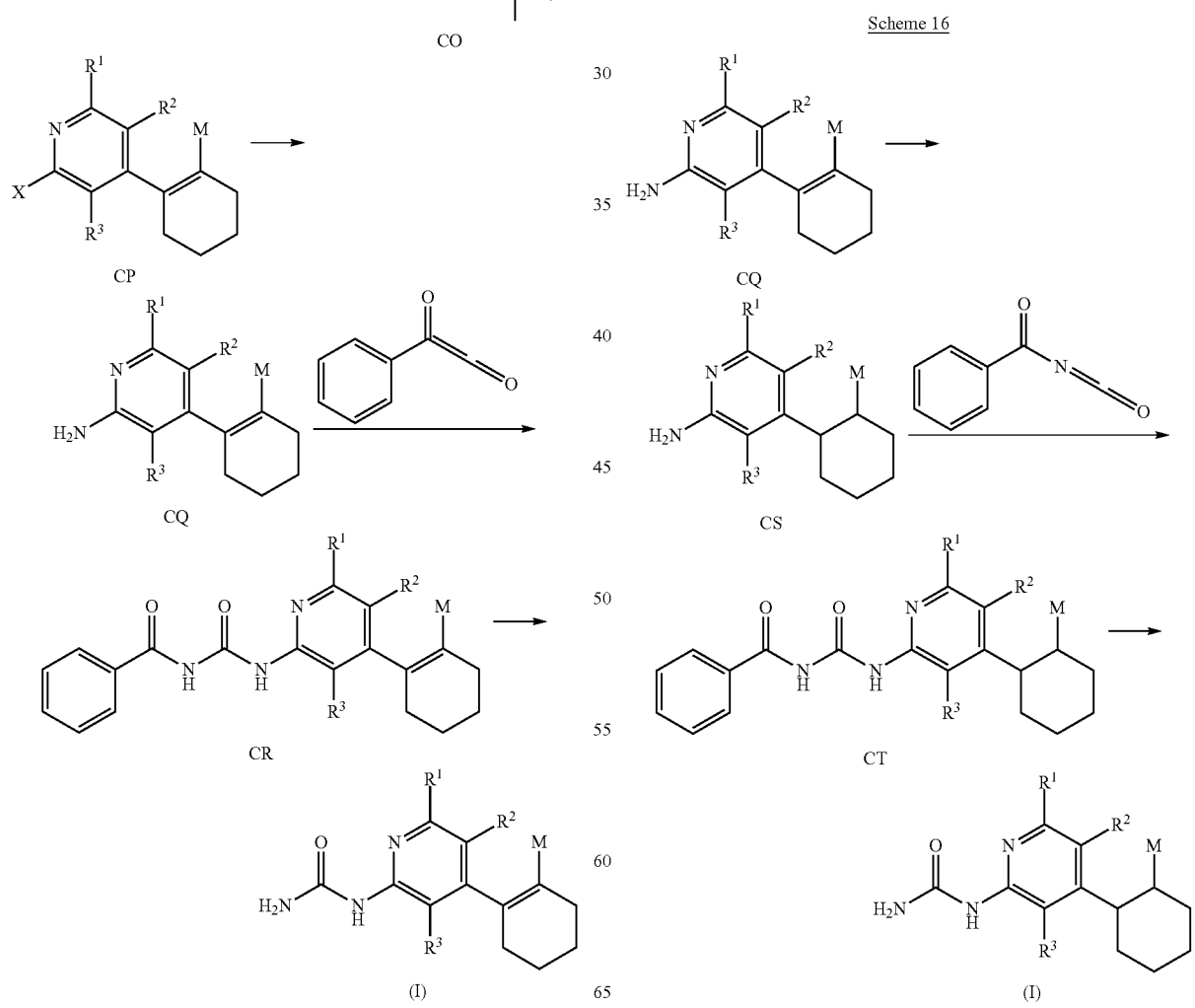

As illustrated in Scheme 16, hydrogenation of the compound of formula CQ, which is prepared using the method described in Scheme 15, in a suitable solvent, at a suitable temperature, under a suitable pressure of hydrogen gas, and in the presence of a suitable catalyst such as 10% Pd on activated carbon, affords amino pyridine CS. Reaction of compound CS with benzoyl isocyanate, in a suitable solvent, at a suitable temperature, provides the compound of formula CT. Final deprotection of the compound of formula CT using potassium carbonate, in a suitable solvent, at a suitable temperature, affords the compound of formula (I).

SPECIFIC SYNTHETIC EXAMPLES

The manner in which the compounds of the invention can be made will be further understood by way of the following Examples. In these Examples, the ES MS retention times reported were measured using the methods set forth in the following Table 2.

TABLE 2

| Method | Time (min) | 95% Water (0.05% HCO$_2$H) + 5% CH$_3$CN (0.05% HCO$_2$H) | CH$_3$CN (0.05% HCO$_2$H) | Flow (mL/min) | Column |
|---|---|---|---|---|---|
| A | 0 | 90 | 10 | 0.8 | Waters BEH |
|  | 1.19 | 0 | 100 | 0.8 | 2.1 × 50 mm C18 |
|  | 1.70 | 0 | 100 | 0.8 | 1.7 μm column |

| Method | Time (min) | Water (0.1% HCO$_2$H) | CH$_3$CN (0.1% HCO$_2$H) | Flow (mL/min) | Column |
|---|---|---|---|---|---|
| B | 0 | 95 | 5 | 2.5 | Agilent Zorbax |
|  | 1.7 | 5 | 95 | 2.5 | C18 SB 3.5 μm |
|  | 2 | 5 | 95 | 2.5 | 4.6 × 30 mm |
|  | 2.1 | 95 | 5 | 2.5 | cartridge |
|  | 2.3 | 95 | 5 | 2.5 |  |

Example 1

Synthesis of {4-[2-(4-fluoro-phenyl)-5-trifluoromethyl-2H-pyrazol-3-yl]-pyridin-2-yl}-urea

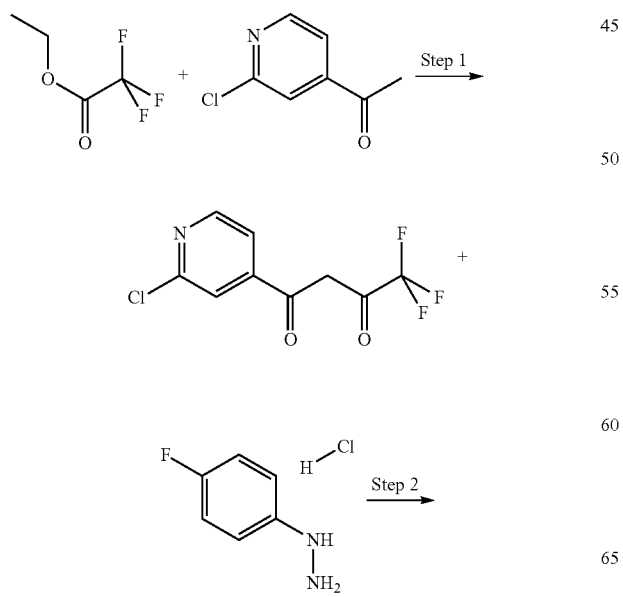

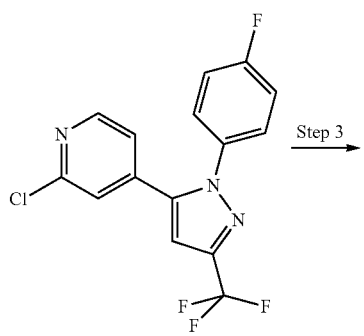

-continued

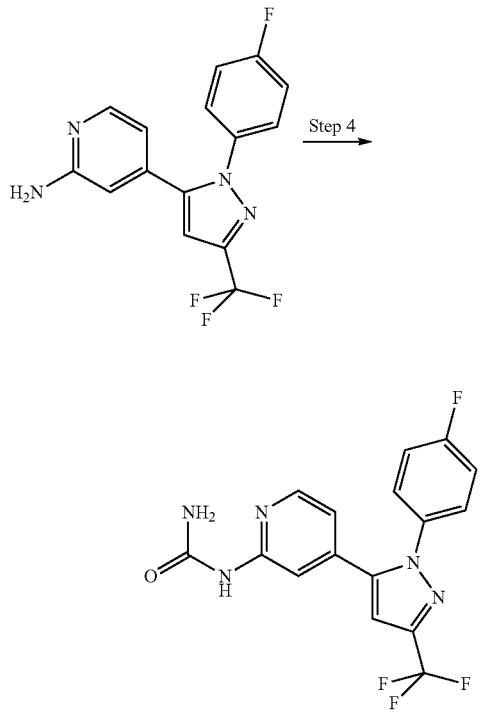

Step 1: Synthesis of 1-(2-chloro-pyridin-4-yl)-4,4,4-trifluoro-butane-1,3-dione Trifluoro-acetic acid ethyl ester (0.30 mL, 2.49 mmol) is added carefully into sodium hydride (60% in mineral oil, 100 mg, 2.49 mmol) suspended in dry THF (2.0 mL) at room temperature. Then 1-(2-chloro-pyridin-4-yl)-ethanone (200 mg, 1.25 mmol) is added into the reaction mixture followed by the addition of ethanol (0.12 mL). The reaction mixture is stirred for 16 hrs and saturated NH$_4$Cl solution (3.0 mL) is added along with 25 mL of water. The mixture is then extracted with EtOAc (3×25 mL). The organic layers are combined and concentrated to give the crude product which is used without purification.

Step 2: Synthesis of 2-chloro-4-[2-(4-fluoro-phenyl)-5-trifluoromethyl-2H-pyrazol-3-yl]-pyridine (4-Fluoro-phenyl)-hydrazine hydrochloride (95 mg, 0.57 mmol) is dissolved in isopropanol (3.0 mL) and triethylamine (0.08 mL, 0.57 mmol) is added. After the mixture is stirred for 5 min, trifluoroacetic acid (0.09 mL, 1.19 mmol) is added and the mixture is again stirred for 5 min Then 1-(2-Chloro-pyridin-4-yl)-4,4,4-trifluoro-butane-1,3-dione (130 mg, 0.52 mmol) is added and the reaction mixture is heated at 85° C. for 40 hrs and stirred at room temperature for another 48 hrs. Water (20 mL) is added and 1.0 M NaOH solution is used to adjust the pH to about 6. The reaction mixture is then extracted with EtOAc (3×20 ml) and the organic layers are combined and concentrated to give the crude product, which is used without purification.

Step 3: Synthesis of 4-[2-(4-fluoro-phenyl)-5-trifluoromethyl-2H-pyrazol-3-yl]-pyridin-2-ylamine 2-Chloro-4-[2-(4-fluoro-phenyl)-5-trifluoromethyl-2H-pyrazol-3-yl]-pyridine (120 mg, 0.35 mmol), Pd$_2$(dba)$_3$ (32 mg, 0.04 mmol) and biphenyl-2-yl-dicyclohexyl-phosphane (32 mg, 0.09 mmol) are mixed in a reaction vial and dry THF (2.0 mL) is added. Then Argon is bubbled through the solution for 5 min and 1.0 M LiHMDS (0.88 mL, 0.88 mmol) in THF is added. The reaction vial is sealed and heated at 65° C. for 16 hrs. More Pd$_2$(dba)$_3$ (32 mg, 0.04 mmol), biphenyl-2-yl-dicyclohexyl-phosphane (32 mg, 0.09 mmol) and 1.0 M LiHMDS (0.88 mL, 0.88 mmol) in THF are added and the reaction mixture is heated at 65° C. for another 5 hrs. Then saturated NH$_4$Cl solution (20 mL) is added along with water (20 mL). The mixture is extracted with EtOAc (3×30 mL) and the organic layers are combined and concentrated to give the crude product. Purification by flash column chromatography using MeOH in DCM (gradient from 0% to 10%) affords 107 mg of product.

Step 4: Synthesis of {4-[2-(4-fluoro-phenyl)-5-trifluoromethyl-2H-pyrazol-3-yl]-pyridin-2-yl}-urea 4-[2-(4-Fluoro-phenyl)-5-trifluoromethyl-2H-pyrazol-3-yl]-pyridin-2-ylamine (132 mg, 0.41 mmol) and benzoyl isocyanate (120 mg, 0.82 mmol) are mixed in DCM (4.0 mL) and the reaction mixture is heated at 50° C. for 16 hrs. After it is cooled down, the solvent is removed and the residue is dissolved in ethanol (2.5 mL). Potassium carbonate (70 mg, 0.49 mmol) is added and the reaction mixture is heated at 85° C. for 2 hrs before it is cooled down to room temperature. The solvent is removed and the residue is partitioned between water (30 mL) and EtOAc (50 mL). The organic layer is separated and concentrated to give the crude product. Purification by flash column chromatography using MeOH in DCM (gradient from 0% to 10%) affords 21 mg of the titled product.

Examples 2-3 in Table 3 are synthesized according to the procedure for Example 1, substituting either commercially available reagents or the appropriate intermediates described above.

TABLE 3

| Example No. | Structure | ES MS M$^+$ + H$^+$ | Retention time (min.) | LCMS Method |
|---|---|---|---|---|
| 1 | 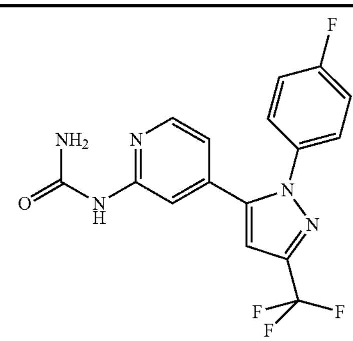 | 366.2 | 0.90 | A |
| 2 | 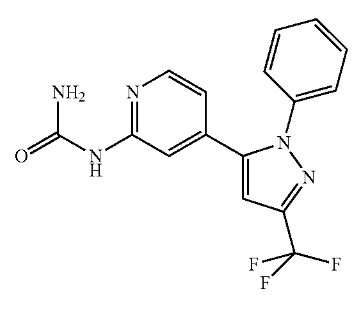 [SMILES: NC(=O)Nc1cc(-c2cc(C(F)(F)F)nn2-c2ccccc2)ccn1] | 348.0 | 0.87 | A |

TABLE 3-continued

| Example No. | Structure | ES MS M⁺ + H⁺ | Retention time (min.) | LCMS Method |
|---|---|---|---|---|
| 3 | 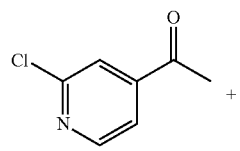 | 340.4 | 0.97 | A |

Example 4

Synthesis of {4-[2-(4-Fluoro-phenyl)-2H-pyrazol-3-yl]-pyridin-2-yl}-urea

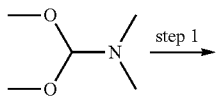

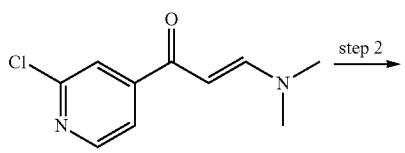

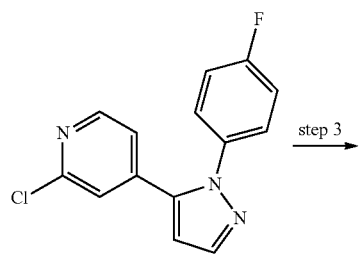

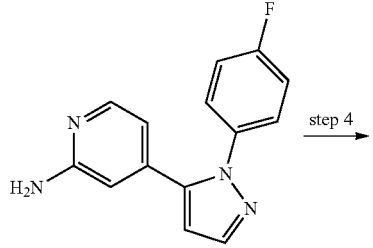

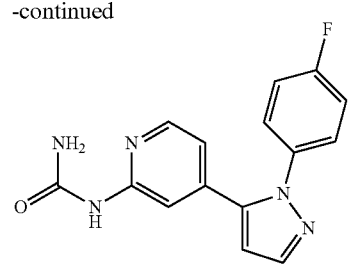

Step 1: Synthesis of (E)-1-(2-Chloro-pyridin-4-yl)-3-dimethylamino-propenone A mixture of 2-chloro-4-acetylpyridine (400 mg, 2.6 mmol) in 5 ml DMF-DMA is refluxed at 110° C. for 1 hour and reaction turns brown. After cooling down to 20° C., the mixture is treated with 30 mL hexane and precipitate forms. The solid is filtered and washed with hexane. Drying under high-vac gives a brown solid (E)-1-(2-Chloro-pyridin-4-yl)-3-dimethylamino-propenone (535 mg).

Step 2: Synthesis of 2-Chloro-4-[2-(4-fluoro-phenyl)-2H-pyrazol-3-yl]-pyridine To a mixture of (E)-1-(2-Chloro-pyridin-4-yl)-3-dimethylamino-propenone (200 mg, 0.95 mmol) and 4-fluorophenyl-hydrazine hydrochloride (170 mg, 1.0 mmol) in 10 mL ethanol is added 0.5 mL of water. The reaction mixture is heated at 110° C. for 30 min Solvent is removed in vacuum and the residue is purified through a Silica column eluting with 0-50% EtOAc/Heptane to give the desired product (254 mg).

Step 3: Synthesis of 4-[2-(4-Fluoro-phenyl)-2H-pyrazol-3-yl]-pyridin-2-ylamine A 10 mL vial is charged with 2-Chloro-4-[2-(4-fluoro-phenyl)-2H-pyrazol-3-yl]-pyridine (160 mg, 0.59 mmol), Tris(dibenzylideneacetone)dipalladium (54 mg, 0.058 mmol) and 2-(dicyclohexylphosphino)biphenyl (53.3 mg, 0.15 mmol) in dry THF (3 mL) and Argon is bubbled through the mixture for 5 min. Additional THF (1 mL) and LiHMDS (1M in toluene, 1.14 mL, 1.5 mmol) are added and the reaction mixture is heated at 65° C. for 14 hours. Then 5 mL of 3.0 M HCl solution is added and the mixture is stirred for 10 min. Additional water (10 mL) is added and the mixture is extracted with EtOAc (2×10 mL). The aqueous layer is separated and its pH is adjusted to 10 by adding saturated Na₂CO₃ aquaous solution. The mixture is then extracted with EtOAc three times and the organic layers are combined, washed with brine and dried over anhdrous Na₂SO₄. Removal of solvent gives the desired product (83 mg).

Step 4: Synthesis of {4-[2-(4-Fluoro-phenyl)-2H-pyrazol-3-yl]-pyridin-2-yl}-urea To the solution of 4-[2-(4-Fluoro-phenyl)-2H-pyrazol-3-yl]-pyridin-2-ylamine (83 mg, 0.33 mmol) in DCM (3.0 mL) is added benzoyl isocynate (96 mg, 0.65 mmol). The resulting mixture is heated at 50° C. for 1 hour. The solvent is then carefully removed in vacuum and to the residue are added K₂CO₃ (54 mg, 0.39 mmol) and ethanol (2 mL). The reaction mixture is then heated at 85° C. for 30 min. Solvent is again removed in vacuum and the residue is purified through a Silica column eluting with 0-100% EtOAc/Heptane to give the titled compound (72 mg).

Examples 5-20 in Table 4 are synthesized according to the procedure for Example 4, substituting either commercially available reagents or the appropriate intermediates described above.

TABLE 4

| Example No. | Structure | ES MS M⁺ + H⁺ | Retention time (min.) | LCMS Method |
|---|---|---|---|---|
| 4 | 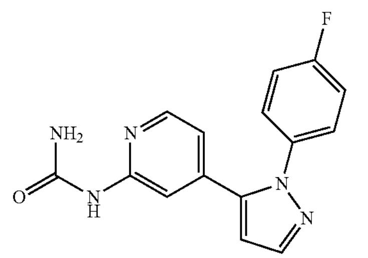 [SMILES: NC(=O)Nc1cc(-c2ccnn2-c2ccc(F)cc2)ccn1] | 298.2 | 0.64 | A |
| 5 | 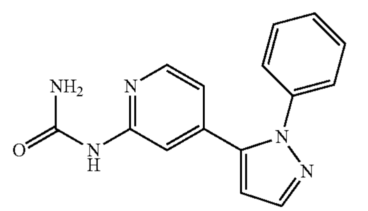 [SMILES: NC(=O)Nc1cc(-c2ccnn2-c2ccccc2)ccn1] | 280.2 | 0.61 | A |
| 6 | 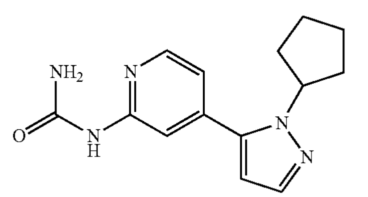 [SMILES: NC(=O)Nc1cc(-c2ccnn2C2CCCC2)ccn1] | 272.7 | 0.68 | A |
| 7 | 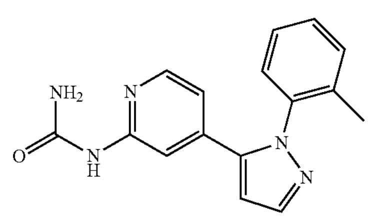 [SMILES: Cc1ccccc1-n1nccc1-c1ccnc(NC(N)=O)c1] | 294.2 | 0.69 | A |
| 8 | 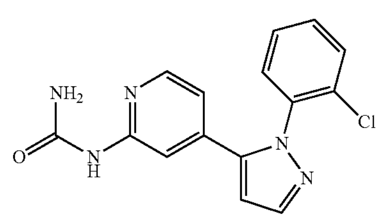 [SMILES: NC(=O)Nc1cc(-c2ccnn2-c2ccccc2Cl)ccn1] | 314.1 | 0.68 | A |

TABLE 4-continued

| Example No. | Structure | ES MS M⁺ + H⁺ | Retention time (min.) | LCMS Method |
|---|---|---|---|---|
| 9 | 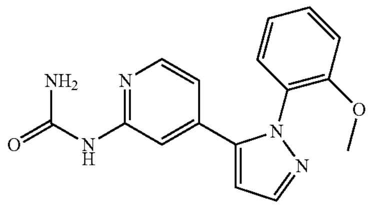 | 310.0 | 0.62 | A |
| 10 | 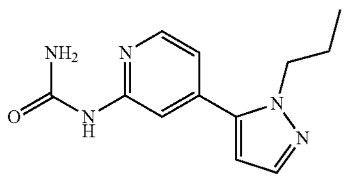 [SMILES: CCCn1nccc1-c1ccnc(NC(N)=O)c1] | 245.9 | 0.51 | A |
| 11 | 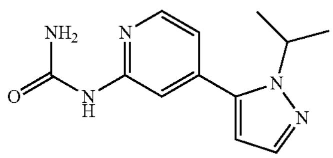 [SMILES: CC(C)n1nccc1-c1ccnc(NC(N)=O)c1] | 245.8 | 0.50 | A |
| 12 | 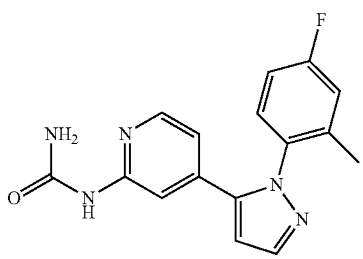 [SMILES: Cc1cc(F)ccc1-n1nccc1-c1ccnc(NC(N)=O)c1] | 312.4 | 0.65 | A |
| 13 | 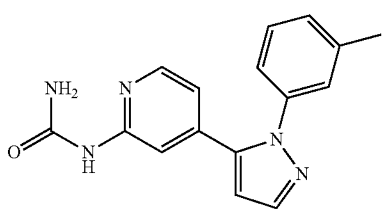 [SMILES: Cc1cccc(-n2nccc2-c2ccnc(NC(N)=O)c2)c1] | 293.6 | 0.71 | A |
| 14 | 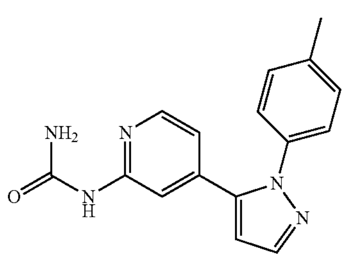 [SMILES: Cc1ccc(-n2nccc2-c2ccnc(NC(N)=O)c2)cc1] | 293.7 | 0.62 | A |
| 15 | 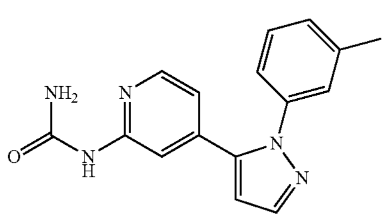 [SMILES: Cc1cccc(-n2nccc2-c2ccnc(NC(N)=O)c2)c1] | 314.0 | 0.75 | A |

TABLE 4-continued
| Example No. | Structure | ES MS M+ + H+ | Retention time (min.) | LCMS Method |
|---|---|---|---|---|
| 16 | 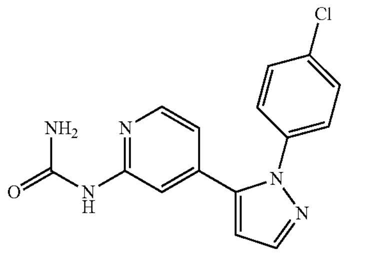 [SMILES: NC(=O)Nc1cc(-c2ccnn2-c2ccc(Cl)cc2)ccn1] | 314.9 | 0.74 | A |
| 17 | 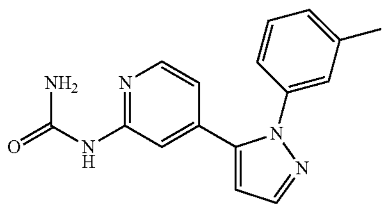 [SMILES: Cc1cccc(-n2nccc2-c2ccnc(NC(N)=O)c2)c1] | 310.1 | 0.63 | A |
| 18 | 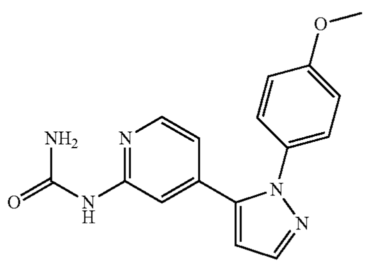 [SMILES: COc1ccc(-n2nccc2-c2ccnc(NC(N)=O)c2)cc1] | 310.0 | 1.34 | B |
| 19 | 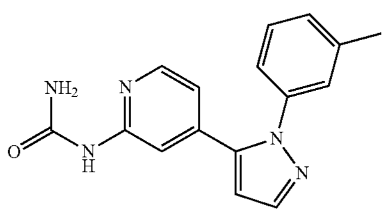 [SMILES: Cc1cccc(-n2nccc2-c2ccnc(NC(N)=O)c2)c1] | 297.6 | 0.65 | A |
| 20 | 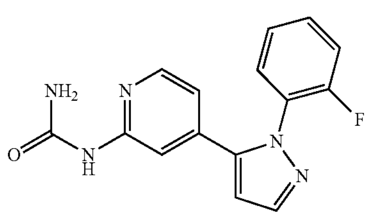 [SMILES: NC(=O)Nc1cc(-c2ccnn2-c2ccccc2F)ccn1] | 298.3 | 0.61 | A |
Example 21
Synthesis of [4-(2-Thiazol-2-yl-2,1-pyrazol-3-yl)-pyridin-2-yl]-urea
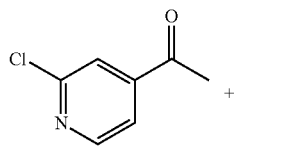
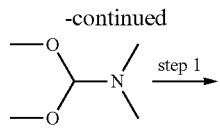

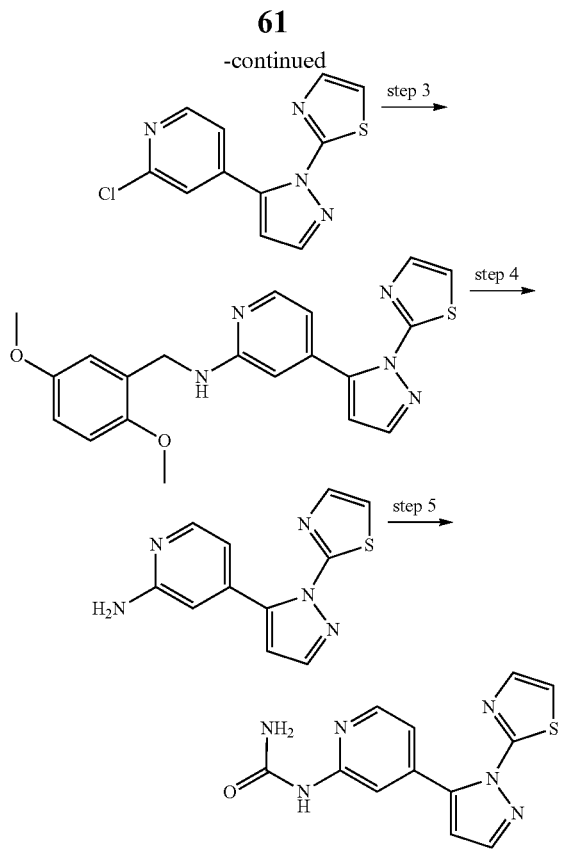

Step 3: Synthesis of (2,5-Dimethoxy-benzyl)-[4-(2-thiazol-2-yl-21'-pyrazol-3-yl)-pyridin-2-yl]-amine 2-Chloro-4-(2-thiazol-2-yl-2H-pyrazol-3-yl)-pyridine (90 mg, 0.34 mmol) and 2,5-dimothoxybenzylamine (1 ml) are mixed in a 5 mL microwave tube. The mixture is heated at 180° C. in microwave reactor for 3 hours. The resulting reaction mixture is poured into water and extracted with EtOAc (3×5 mL). The organic layers are combined, washed with brine, dried over anhdrous sodium sulfate and concentrated to give the crude product. The crude is purified through a Silica column eluting with 0-70% EtOAc/Heptane to give the titled compound (120 mg).

Step 4: Synthesis of 4-(2-Thiazol-2-yl-21'-pyrazol-3-yl)-pyridin-2-ylamine (2,5-Dimethoxy-benzyl)-[4-(2-thiazol-2-yl-2H-pyrazol-3-yl)-pyridin-2-yl]-amine (120 mg, 0.31 mmol) is mixed with trifluoroacetic acid (1.0 mL) in a 2 mL microwave tube and heated at 150° C. for 10 min. The extra acid is removed in vacuum. Saturated sodium carbonate solution (5.0 mL) is added into the residue and the mixture is extracted with EtOAc (3×5 ml). The organic layers are combined, washed with brine, dried over anhydrous sodium sulfate and concentrated to give the crude product (74 mg) which is in the next step without further purification.

Step 1: Synthesis of (E)-1-(2-Chloro-pyridin-4-yl)-3-dimethylamino-propenone

The titled compound is synthesized according to the procedure for step 1 of Example 4.

Step 2: Synthesis of 2-Chloro-4-(2-thiazol-2-yl-21'-pyrazol-3-yl)-pyridine

The titled compound is synthesized according to the procedure for step 2 of Example 4.

Step 5: Synthesis of [4-(2-Thiazol-2-yl-21'-pyrazol-3-yl)-pyridin-2-yl]-urea

The titled compound (5 mg) is synthesized according to the procedure for step 4 of Example 4.

Examples 22-23 in Table 5 are synthesized according to the procedure for Example 21, substituting either commercially available reagents or the appropriate intermediates described above.

TABLE 5

| Example No. | Structure | ES MS M+ + H+ | Retention time (min.) | LCMS Method |
|---|---|---|---|---|
| 21 | 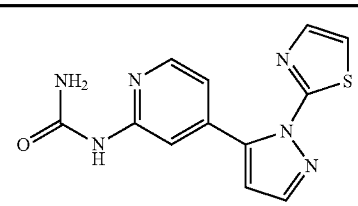 | 287.1 | 0.49 | A |
| 22 | 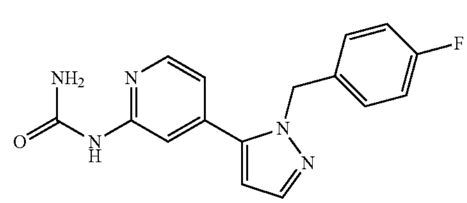 [SMILES: NC(=O)Nc1cc(-c2ccnn2Cc2ccc(F)cc2)ccn1] | 312.2 | 0.68 | A |

TABLE 5-continued

| Example No. | Structure | ES MS M+ + H+ | Retention time (min.) | LCMS Method |
|---|---|---|---|---|
| 23 | 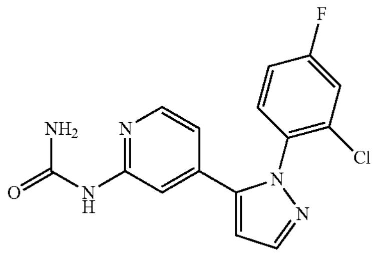 [SMILES: NC(=O)Nc1cc(-c2ccnn2-c2ccc(F)cc2Cl)ccn1] | 332.1 | 0.66 | A |

Example 24

Synthesis of [4-(2-o-Tolyl-ethyl)-pyridin-2-yl]-urea

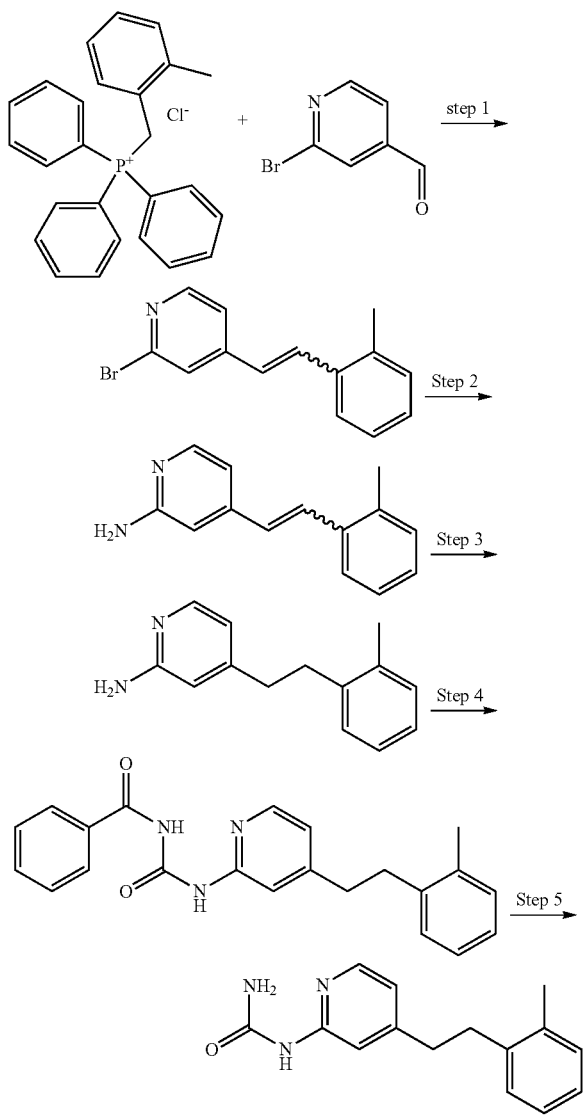

Step 1: Synthesis of mixture of E and Z 2-Bromo-4-(2-o-tolyl-vinyl)-pyridine

To the suspension of (2-methylbenzyl)triphenylphosphonium chloride (1.2 g, 3.0 mmol) in THF (30 mL) at −78° C. is added n-BuLi 1.6 M in hexane (1.8 mL, 3.0 mmol) dropwise. The resulting reaction mixture is stirred at −78° C. for 30 min when 2-bromo-pyridine-4-carbaldehyde (555 mg, 3.0 mmol) is added in small portions. The mixture is warmed up to room temperature gradually and stirred for 20 hours. Then the reaction is quenched with saturated aqueous NH$_4$Cl solution (30 mL) and extracted with EtOAc (3×20 mL). The combined organic layers are washed with brine, dried over anhydrous sodium sulfate and concentrated. The crude is purified by silica flash column chromatography eluting with EtOAc in Heptane (gradient from 0% to 20%) to give a mixture of E and Z 2-Bromo-4-(2-o-tolyl-vinyl)-pyridine (510 mg).

Step 2: Synthesis of mixture of E and Z 4-(2-o-Tolyl-vinyl)-pyridin-2-ylamine

A 2 mL microwave reaction tube is charged with the mixture of E and Z 2-bromo-4-(2-o-tolyl-vinyl)-pyridine (510 mg, 1.9 mmol), Copper (I) oxide (53 mg, 0.37 mmol), Ammonium Hydroxide (28%, 0.5 mL) and 1-4-dioxane (0.5 mL). The reaction mixture is heated at 150° C. for 30 min in a microwave reactor. Then water (5 mL) is added and the mixture is extracted with EtOAc (3×20 mL). The combined organic layers are washed with brine, dried over anhydrous sodium sulfate and concentrated. The crude is purified by silica flash column chromatography eluting with EtOAc in Heptane (gradient from 0% to 100%) to give the desired mixture of products (210 mg).

Step 3: Synthesis of 4-(2-o-Tolyl-ethyl)-pyridin-2-ylamine

To the solution of mixture of E and Z 4-(2-o-Tolyl-vinyl)-pyridin-2-ylamine (200 mg, 0.95 mmol) in methanol (10 mL) is added 5% palladium on carbon (20 mg). The mixture is purged and back filled with hydrogen three times using a hydrogen balloon. The reaction is then stirred at room temperature for 3 hours under the hydrogen atmosphere. The palladium on carbon is filtered and the filtrate is concentrated to give the desired product (198 mg).

Step 4: Synthesis of 1-Benzoyl-3-[4-(2-o-tolyl-ethyl)-pyridin-2-yl]-urea 4-(2-o-Tolyl-ethyl)-pyridin-2-ylamine (100 mg, 0.47 mmol) is dissolved in methylene chloride (3 mL). Then benzoyl isocynate (100 mg, 0.71 mmol) is added. The resulting mixture is sealed and heated at 65° C. for 1 hour. The solvent is then removed to give 225 mg of crude which is used in the next step without purification.

Step 5: Synthesis of [4-(2-o-Tolyl-ethyl)-pyridin-2-yl]-urea

To the crude 1-benzoyl-3-[4-(2-o-tolyl-ethyl)-pyridin-2-yl]-urea (225 mg, 0.63 mmol) in ethanol (2 mL) is added potassium carbonate (86 mg, 0.63 mmol). The resulting mixture is heated at 85° C. for 30 min. Solvent is removed and the residue is purified by silica flash column chromatography eluting with EtOAc in Heptane (gradient from 0% to 100%) to give 60 mg of the titled product.

Examples 25-27 in Table 6 are synthesized according to the procedure for Example 24, substituting either commercially available reagents or the appropriate intermediates described above.

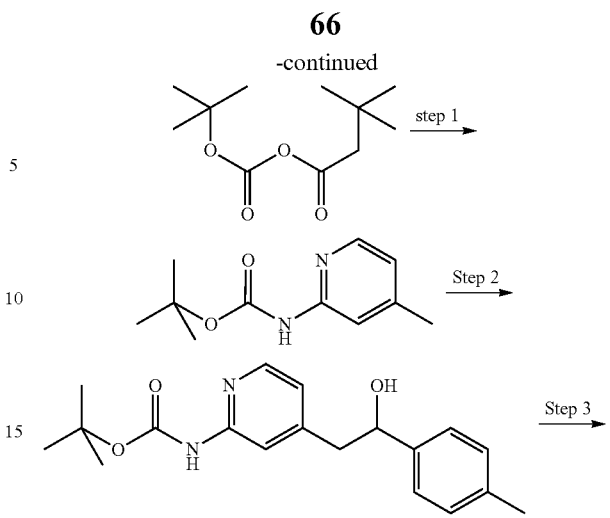

TABLE 6

| Example No. | Structure | ES MS M⁺ + H⁺ | Retention time (min.) | LCMS Method |
|---|---|---|---|---|
| 24 | 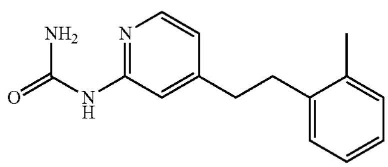 [SMILES: Cc1ccccc1CCc1ccnc(NC(N)=O)c1] | 256.5 | 0.65 | A |
| 25 | 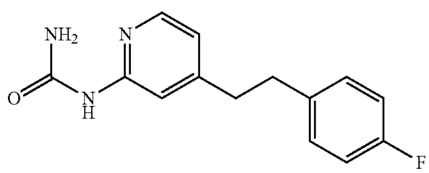 [SMILES: NC(=O)Nc1cc(CCc2ccc(F)cc2)ccn1] | 260.2 | 0.60 | A |
| 26 | 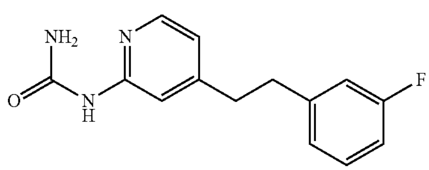 [SMILES: NC(=O)Nc1cc(CCc2cccc(F)c2)ccn1] | 260.2 | 0.60 | A |
| 27 | 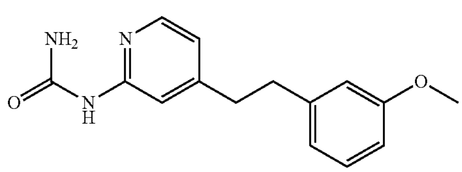 [SMILES: COc1cccc(CCc2ccnc(NC(N)=O)c2)c1] | 272.2 | 0.58 | A |

Example 28 and 29

Syntheses of [4-(2-p-Tolyl-ethyl)-pyridin-2-yl]-urea and [4-(2-Hydroxy-2-p-tolyl-ethyl)-pyridin-2-yl]-urea

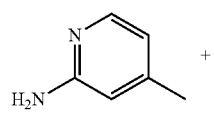

-continued

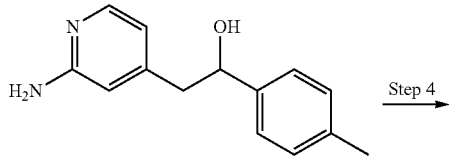

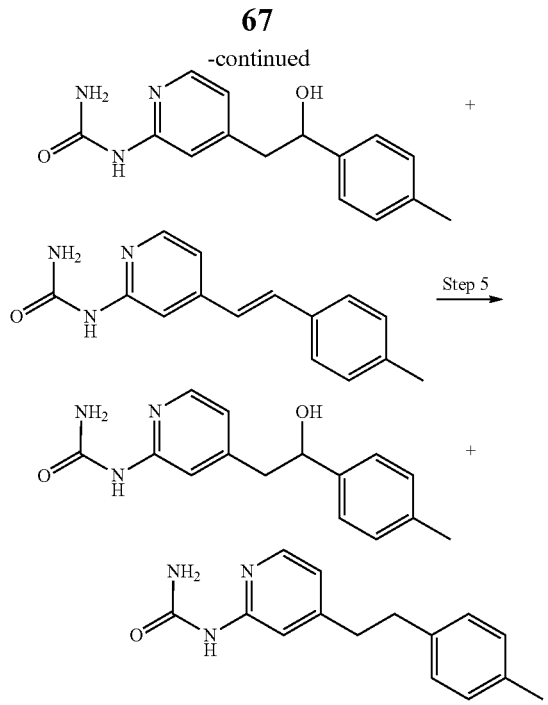

Step 1: Synthesis of (4-Methyl-pyridin-2-yl)-carbamic acid tert-butyl ester

To the solution of di-tert-butyl dicarbonate (16.7 g, 76.3 mmol) in t-BuOH (melted, 30 mL) is added 4-methyl-pyridin-2-ylamine (7.5 g, 69 mmol). The mixture is stirred at room temperature for 16 hours. After concentration, the residue is purified by silica flash column chromatography eluting with 30% EtOAc in Heptane to give 8.2 g of desired product.

Step 2: Synthesis of [4-(2-Hydroxy-2-p-tolyl-ethyl)-pyridin-2-yl]-carbamic acid tert-butyl ester The solution of (4-methyl-pyridin-2-yl)-carbamic acid tert-butyl ester (200 mg, 0.96 mmol) in dry THF (10 mL) is cooled to −78° C. The 1.6 M n-BuLi in hexane solution (3.0 mL, 4.8 mmol) is added dropwise at −78° C. Then the cooling bath is removed and the mixture is stirred at room temperature for 15 min. The reaction mixture is cooled down to −78° C. again and 4-methylbenzylaldehyde (231 mg, 1.9 mmol) is added. The mixture is stirred for another 30 min at −78° C. and saturated NH₄Cl aquaous solution (25 mL) is added. The reaction mixture is then warmed up to room temperature and EtOAc (30 mL) is added along with water (30 mL). The resulting mixture is stirred for 10 min and the aqueous layer is separated and extracted with EtOAc (3×35 ml). The combined organic layers are washed with brine, dried over anhydrous sodium sulfate and concentrated. The crude is purified by silica flash column chromatography eluting with EtOAc in Heptane (gradient from 0% to 60%) to give 80 mg of the desired product.

Step 3: Synthesis of 2-(2-Amino-pyridin-4-yl)-1-p-tolyl-ethanol

To the solution of [4-(2-hydroxy-2-p-tolyl-ethyl)-pyridin-2-yl]-carbamic acid tert-butyl ester (80 mg, 0.24 mmol) in DCM (2 mL) is added trifluoroacetic acid (0.5 mL). The mixture is stirred for 30 min at room temperature. Then saturated NaHCO₃ aquaous solution (10 mL) is added slowly and the resulting mixture is extracted with DCM (2×10 mL). All the organic layers are combined and concentrated. The crude is purified by silica flash column chromatography eluting with EtOAc in Heptane (gradient from 0% to 100%) to give 40 mg of the desired product.

Step 4: Syntheses of [4-((E)-2-p-Tolyl-vinyl)-pyridin-2-yl]-urea and [4-(2-Hydroxy-2-p-tolyl-ethyl)-pyridin-2-yl]-urea 2-(2-Amino-pyridin-4-yl)-1-p-tolyl-ethanol (40 mg, 0.18 mmol) is dissolved in methylene chloride (3 mL). Then benzoyl isocynate (7.6 mg, 0.18 mmol) is added. The reaction mixture is sealed and heated at 50° C. for 1 hour. The solvent is then carefully removed and to the residue are added ethanol (2 mL) and potassium carbonate (25 mg, 0.18 mmol). The resulting mixture is heated at 85° C. for 30 min. Then solvent is removed to give 36 mg of crude desired product which is used in the next step without purification.

Step 5: Syntheses of [4-(2-p-Tolyl-ethyl)-pyridin-2-yl]-urea and [4-(2-Hydroxy-2-p-tolyl-ethyl)-pyridin-2-yl]-urea To the solution of the mixture of [4-((E)-2-p-Tolyl-vinyl)-pyridin-2-yl]-urea and [4-(2-hydroxy-2-p-tolyl-ethyl)-pyridin-2-yl]-urea (36 mg) in ethanol (3 mL) is added 5% palladium on carbon (5 mg). The mixture is purged and back filled with hydrogen three times using a hydrogen balloon. Then the reaction is stirred for 3 hours under the hydrogen atmosphere. The palladium on carbon is filtered and the filtrate is purified by Gilson preparative HPLC to give 12 mg of [4-(2-p-tolyl-ethyl)-pyridin-2-yl]-urea and 3 mg of [4-(2-hydroxy-2-p-tolyl-ethyl)-pyridin-2-yl]-urea.

Examples 30-33 in Table 7 are synthesized according to the procedures for Example 28 and 29, substituting either commercially available reagents or the appropriate intermediates described above.

TABLE 7

| Example No. | Structure | ES MS M⁺ + H⁺ | Retention time (min.) | LCMS Method |
|---|---|---|---|---|
| 28 | 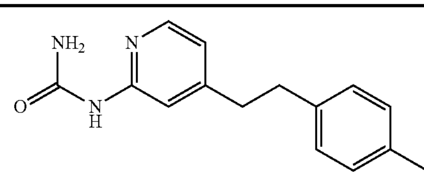 | 256.2 | 0.75 | A |

TABLE 7-continued

| Example No. | Structure | ES MS M⁺ + H⁺ | Retention time (min.) | LCMS Method |
|---|---|---|---|---|
| 29 | 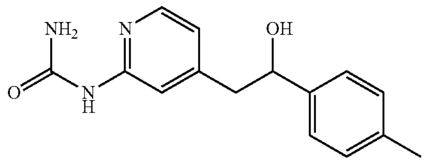 [SMILES: Cc1ccc(C(O)Cc2ccnc(NC(N)=O)c2)cc1] | 272.2 | 0.55 | A |
| 30 | 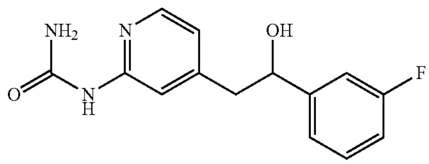 [SMILES: NC(=O)Nc1cc(CC(O)c2cccc(F)c2)ccn1] | 276.2 | 0.47 | A |
| 31 | 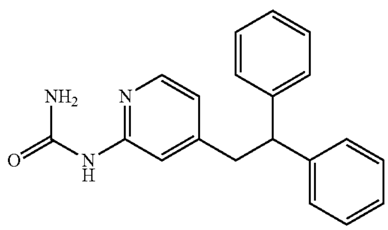 [SMILES: NC(=O)Nc1cc(CC(c2ccccc2)c2ccccc2)ccn1] | 318.2 | 0.82 | A |
| 32 | 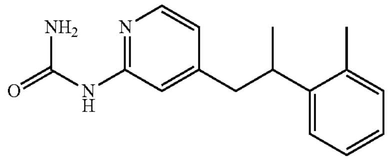 [SMILES: Cc1ccccc1C(C)Cc1ccnc(NC(N)=O)c1] | 270.2 | 0.74 | A |
| 33 | 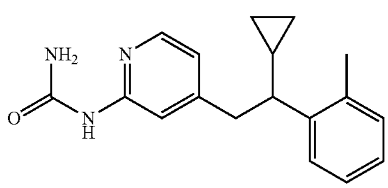 [SMILES: Cc1ccccc1C(Cc1ccnc(NC(N)=O)c1)C1CC1] | 296.2 | 0.81 | A |

Example 34

Synthesis of [4-(2-Hydroxy-2-phenyl-propyl)-pyridin-2-yl]-urea

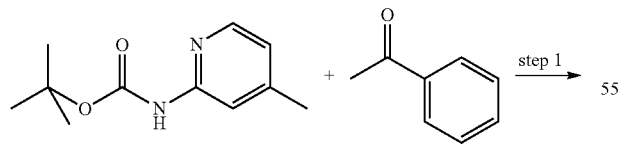

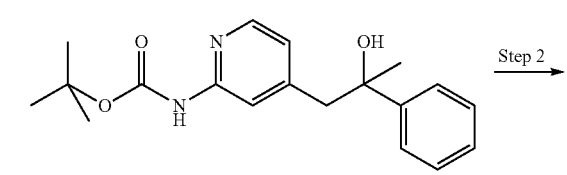

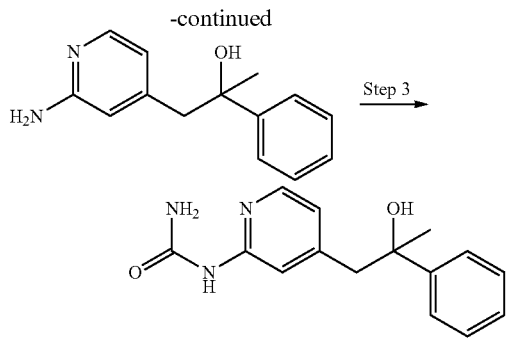

The synthesis of (4-methyl-pyridin-2-yl)-carbamic acid tert-butyl ester is described in Example 28.

Step 1: Synthesis of [4-(2-Hydroxy-2-phenyl-propyl)-pyridin-2-yl]-carbamic acid tert-butyl ester The solution of (4-methyl-pyridin-2-yl)-carbamic acid tert-butyl ester (100 mg, 0.48 mmol) in dry THF (5 mL) is cooled down to −78° C. The 1.6 M n-BuLi in hexane solution (1.5 mL, 2.4 mmol) is added dropwise at −78° C. Then the cooling bath is removed and the mixture is stirred at room temperature for 15 min. The reaction mixture is cooled down to −78° C. again and 1-phenyl-ethanone (0.28 mL, 2.4 mmol) is added. The mixture is stirred for another 30 min at −78° C. and saturated NH₄Cl aquaous solution (25 mL) is added. The reaction mixture is then warmed up to room temperature and EtOAc (50 mL) is added along with water (30 mL). The resulting mixture is stirred for 10 min and the aqueous layer is separated and extracted with EtOAc (2×35 ml). The organic layers are combined and concentrated to give the crude product. Purification by silica flash column chromatography using MeOH in DCM (gradient from 0% to 10%) afforded 140 mg of desired product.

Step 2: Synthesis of 1-(2-Amino-pyridin-4-yl)-2-phenyl-propan-2-ol

To the solution of [4-(2-hydroxy-2-phenyl-propyl)-pyridin-2-yl]-carbamic acid tert-butyl ester (140 mg, 0.43 mmol) in DCM (4 mL) is added trifluoroacetic acid (0.3 mL). The mixture is stirred for 16 hrs at room temperature. Then EtOAc (35 mL) is added followed by the addition of saturated NaHCO₃ aquaous solution (15 mL) and water (15 mL). The mixture is stirred for 15 min and the aqueous layer is separated. The aqueous layer is then extracted with EtOAc (2×25 mL). All the organic layers are combined and concentrated to give 120 mg of crude product which is used in the next step without purification.

Step 3: Synthesis of [4-(2-Hydroxy-2-phenyl-propyl)-pyridin-2-yl]-urea

The crude 1-(2-Amino-pyridin-4-yl)-2-phenyl-propan-2-ol (120 mg) is dissolved in methylene chloride (4 mL). Then benzoyl isocynate (155 mg, 1.1 mmol) is added. The reaction mixture is sealed and heated at 50° C. for 16 hour. The solvent is then carefully removed and to the residue are added ethanol (5 mL) and potassium carbonate (73 mg, 0.53 mmol). The resulting mixture is heated at 85° C. for 2 hrs. Then solvent is removed to give the crude product which is purified by silica flash column chromatography using MeOH in DCM (gradient from 0% to 10%) to give 67 mg of the titled product.

Example 35

Synthesis of [4-(2-Phenyl-propyl)-pyridin-2-yl]-urea

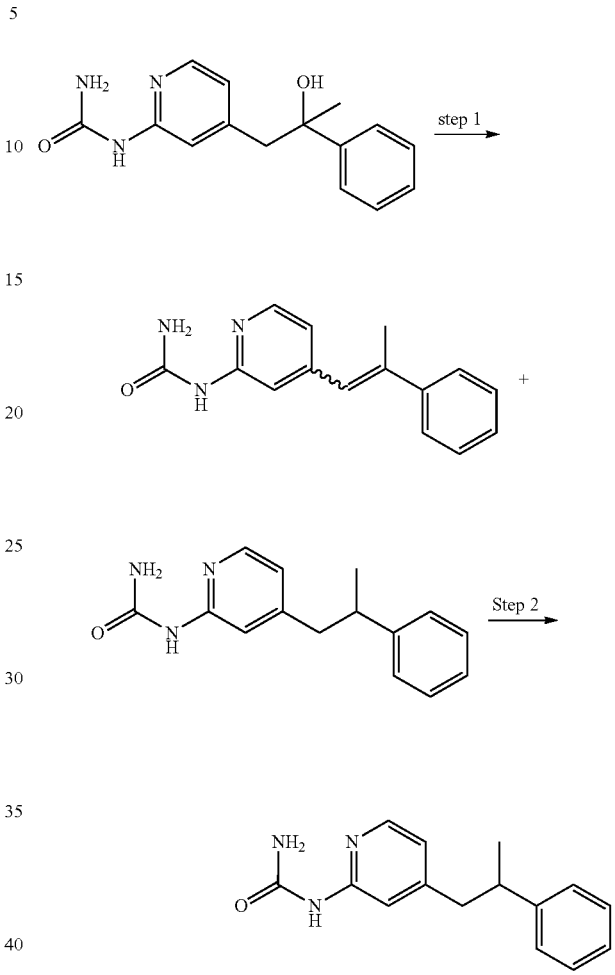

Step 1: Syntheses of [4-(2-Phenyl-propenyl)-pyridin-2-yl]-urea and [4-(2-Phenyl-propyl)-pyridin-2-yl]-urea

[4-(2-Hydroxy-2-phenyl-propyl)-pyridin-2-yl]-urea (40 mg, 0.15 mmol, Example 34) is dissolved in DCM (2.0 mL) and it is cooled down to 0° C. Then triethylsilane (0.04 mL, 0.22 mmol) is added followed by the addition of trifluoroborane diethyl etherate (0.04 mL, 0.30 mmol). The mixture is stirred for 16 hrs and saturated NaHCO₃ aquaous solution (5 mL) is added along with 5 mL of water. The mixture is

TABLE 8

| Example No. | Structure | ES MS M⁺ + H⁺ | Retention time (min.) | LCMS Method |
|---|---|---|---|---|
| 34 | | 272.6 | 0.46 | A | extracted with EtOAc (3×20 mL) and the organic layers are combined and concentrated to give 32 mg of mixture of 4-((E)-2-phenyl-propenyl)-pyridin-2-yl]-urea and [4-(2-phenyl-propyl)-pyridin-2-yl]-urea which is used in the next step without purification.

Step 2: Synthesis of [4-(2-Phenyl-propyl)-pyridin-2-yl]-urea

The mixture of 4-(2-phenyl-propenyl)-pyridin-2-yl]-urea and [4-(2-phenyl-propyl)-pyridin-2-yl]-urea (32 mg) is dissolved in DCM (0.5 mL) and methanol (0.5 mL). Then 5% palladium on carbon (13 mg, 0.006 mmol) is added. The reaction is stirred for 16 hours under the hydrogen atmosphere. The palladium on carbon is filtered and the filtrate is concentrated to give the crude product. Purification by Gilson preparative HPLC affords 15 mg of the titled product.

TABLE 9

| Example No. | Structure | ES MS M⁺ + H⁺ | Retention time (min.) | LCMS Method |
|---|---|---|---|---|
| 35 | 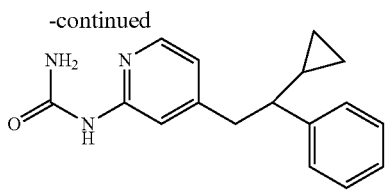 | 255.9 | 0.66 | A |

Example 36

Synthesis of [4-(2-Cyclopropyl-2-phenyl-ethyl)-pyridin-2-yl]-urea

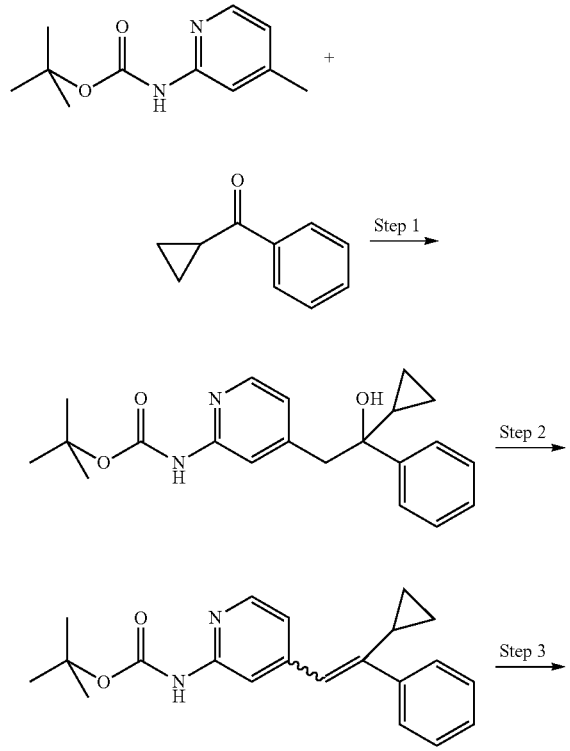

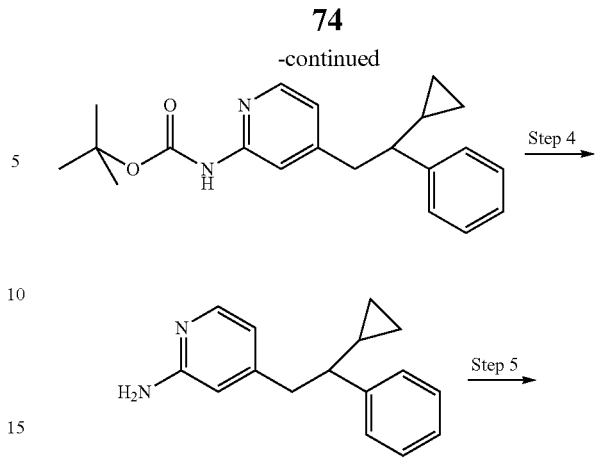

The synthesis of (4-methyl-pyridin-2-yl)-carbamic acid tert-butyl ester is described in Example 28.

Step 1: Synthesis of [4-(2-Cyclopropyl-2-hydroxy-2-phenyl-ethyl)-pyridin-2-yl]-carbamic acid tert-butyl ester (4-Methyl-pyridin-2-yl)-carbamic acid tert-butyl ester (200 mg, 0.96 mmol) is dissolved in dry THF (10 mL) and it is cooled down to −78° C. After 1.6 M n-BuLi (3.0 mL, 4.8 mmol) is added at −78° C., the cooling bath is removed and the mixture is stirred at room temperature for 15 min. Then the reaction mixture is cooled down to −78° C. again and cyclopropyl-phenyl-methanone (0.68 mL, 4.8 mmol) is added. After the mixture is stirred for 30 min at −78° C., saturated NH₄Cl aqueous solution (35 mL) is added and the reaction is warmed up to room temperature. EtOAc (70 mL) is added along with water (70 mL). The mixture is stirred for another 10 min and the aqueous layer is separated, extracted with EtOAc (2×35 ml). The organic layers are combined and concentrated to give the crude product. Purification by silica flash column chromatography using MeOH in DCM (gradient from 0% to 10%) affords 280 mg of the desired product.

Step 2: Synthesis of [4-(2-Cyclopropyl-2-phenyl-vinyl)-pyridin-2-yl]-carbamic acid tert-butyl ester

[4-(2-Cyclopropyl-2-hydroxy-2-phenyl-ethyl)-pyridin-2-yl]-carbamic acid tert-butyl ester (280 mg, 0.79 mmol) and 4-dimethylaminopyridine (97 mg, 0.79 mmol) are dissovled in pyridine (3.0 mL) and thionyl chloride (0.12 mL, 1.6 mmol) is added at 0° C. After the mixture is stirred for 3 hrs at room temperature, saturated NaHCO$_3$ aqueous solution (4 mL) is added along with water (20 ml). The mixture is extracted with EtOAc (3×25 mL) and the organic layers are combined and concentrated to give the crude product. Purification by silica flash column chromatography using MeOH in DCM (gradient from 0% to 6%) affords 94 mg of the desired product.

Step 3: Synthesis of [4-(2-Cyclopropyl-2-phenyl-ethyl)-pyridin-2-yl]-carbamic acid tert-butyl ester

[4-(2-Cyclopropyl-2-phenyl-vinyl)-pyridin-2-yl]-carbamic acid tert-butyl ester (94 mg, 0.28 mmol) is dissolved in methanol (1.5 mL) and DCM (1.5 mL). Then 5% palladium on carbon (59 mg, 0.028 mmol) is added. The reaction is stirred for 16 hours under the hydrogen atmosphere. The palladium on carbon is filtered and the filtrate is concentrated to give 97 mg of the crude product which is used in the next step without purification.

Step 4: Synthesis of 4-(2-Cyclopropyl-2-phenyl-ethyl)-pyridin-2-ylamine

The crude [4-(2-cyclopropyl-2-phenyl-ethyl)-pyridin-2-yl]-carbamic acid tert-butyl ester (97 mg) is dissolved in DCM (1.5 mL) and trifluoroacetic acid (0.5 mL) is added. After the mixture is stirred for 16 hrs, EtOAc (25 mL) is added followed by the addition of saturated NaHCO$_3$ aqueous solution (10 mL) and water (15 mL). The mixture is stirred for 15 min and the aqueous layer is separated and extracted with EtOAc (2×25 ml). All the organic layers are combined and concentrated to give 70 mg of the crude product which is used in the next step without purification.

Step 5: Synthesis of [4-(2-Cyclopropyl-2-phenyl-ethyl)-pyridin-2-yl]-urea

The crude 4-(2-cyclopropyl-2-phenyl-ethyl)-pyridin-2-ylamine (70 mg) is dissolved in methylene chloride (2 mL). Then benzoyl isocynate (86 mg, 0.59 mmol) is added. The reaction mixture is sealed and heated at 50° C. for 16 hour.

The solvent is then carefully removed and to the residue are added ethanol (2 mL) and potassium carbonate (61 mg, 0.44 mmol). The resulting mixture is heated at 85° C. for 45 min. Then solvent is removed and the residue is partitioned between water (35 mL) and EtOAc (55 mL). The aqueous layer is separated and extracted with EtOAc (2×40 mL). The organic layers are combined and concentrated to give the crude product. Purification by silica flash column chromatography using MeOH in DCM (gradient from 0% to 10%) followed by Gilson preparative HPLC affords 8 mg of the titled product.

Example 37 in Table 10 is synthesized according to the procedure for Example 36 substituting either commercially available reagents or the appropriate intermediates described above.

TABLE 10

| Example No. | Structure | ES MS M$^+$ + H$^+$ | Retention time (min.) | LCMS Method |
|---|---|---|---|---|
| 36 | 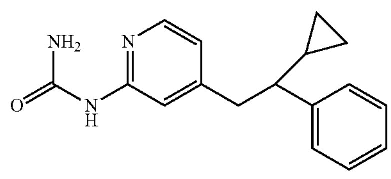 [SMILES: NC(=O)Nc1cc(CC(c2ccccc2)C2CC2)ccn1] | 281.8 | 0.71 | A |
| 37 | 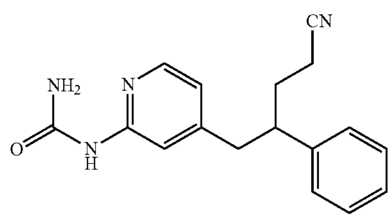 [SMILES: N#CCCC(Cc1ccnc(NC(N)=O)c1)c1ccccc1] | 295.4 | 0.56 | A |

Example 38

Synthesis of [4-(2-Phenyl-2-o-tolyl-ethyl)-pyridin-2-yl]-urea

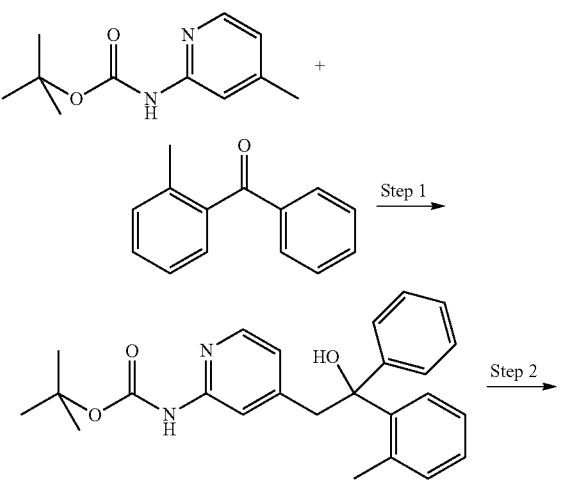

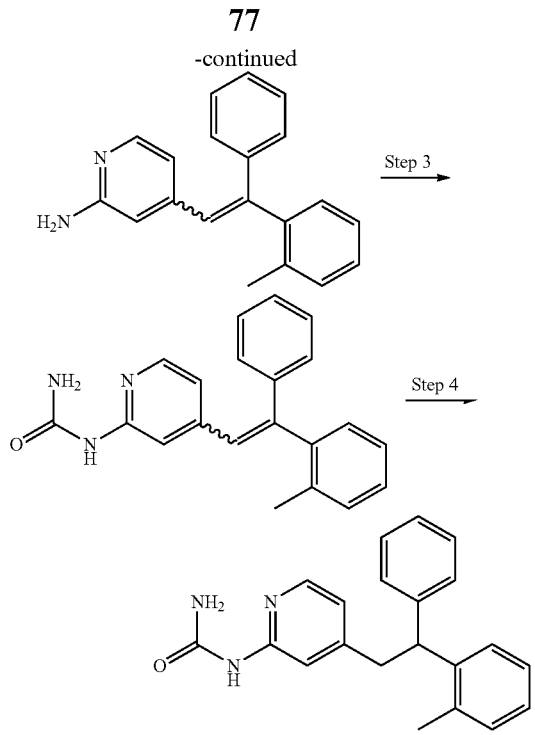

The synthesis of (4-methyl-pyridin-2-yl)-carbamic acid tert-butyl ester is described in Example 28.

Step 1: Synthesis of [4-(2-Hydroxy-2-phenyl-2-o-tolyl-ethyl)-pyridin-2-yl]-carbamic acid tert-butyl ester (4-Methyl-pyridin-2-yl)-carbamic acid tert-butyl ester (300 mg, 1.4 mmol) is dissolved in dry THF (15 mL) and it is cooled down to −78° C. After 1.6 M n-BuLi (4.5 mL, 7.2 mmol) is added at −78° C., the cooling bath is removed and the mixture is stirred at room temperature for 15 min. Then the reaction mixture is cooled down to −78° C. again and phenyl-o-tolyl-methanone (1.3 mL, 7.2 mmol) is added. After the mixture is stirred for 30 min at −78° C., saturated NH$_4$Cl aqueous solution (15 mL) is added and the reaction is warmed up to room temperature. EtOAc (60 mL) is added along with water (50 mL). The mixture is stirred for another 10 min and the aqueous layer is separated, extracted with EtOAc (2×35 ml). The organic layers are combined and concentrated to give the crude product. Purification by silica flash column chromatography using MeOH in DCM (gradient from 0% to 10%) affords 361 mg of the desired product.

Step 2: Synthesis of 4-(2-Phenyl-2-o-tolyl-vinyl)-pyridin-2-ylamine

[4-(2-Hydroxy-2-phenyl-2-o-tolyl-ethyl)-pyridin-2-yl]-carbamic acid tert-butyl ester (361 mg, 0.89 mmol) is dissolved in DCM (4 mL) and trifluoroacetic acid (2.0 mL) is added. After the mixture is stirred for 16 hrs, EtOAc (55 mL) is added followed by the addition of saturated NaHCO$_3$ aqueous solution (15 mL) and water (35 mL). The mixture is stirred for another 15 min and the aqueous layer is separated. The aqueous layer is then extracted with EtOAc (2×35 mL) and all the organic layers are combined and concentrated to give 251 mg of the crude product which is used in the next step without purification.

Step 3: Synthesis of [4-(2-Phenyl-2-o-tolyl-vinyl)-pyridin-2-yl]-urea

The crude 4-(2-phenyl-2-o-tolyl-vinyl)-pyridin-2-ylamine (251 mg) is dissolved in methylene chloride (5 mL). Then benzoyl isocynate (258 mg, 1.75 mmol) is added. The reaction mixture is sealed and heated at 50° C. for 16 hour. The solvent is then carefully removed and to the residue are added ethanol (5 mL) and potassium carbonate (182 mg, 1.32 mmol). The resulting mixture is heated at 80° C. for 45 min. Then solvent is removed and the residue is partitioned between water (45 mL) and EtOAc (55 mL). The aqueous layer is separated and extracted with EtOAc (2×30 mL). The organic layers are combined and concentrated to give the crude product. Purification by silica flash column chromatography using MeOH in DCM (gradient from 0% to 10%) affords 185 mg of the desired product.

Step 4: Synthesis of [4-(2-Phenyl-2-o-tolyl-ethyl)-pyridin-2-yl]-urea

[4-(2-Phenyl-2-o-tolyl-vinyl)-pyridin-2-yl]-urea (140 mg, 0.43 mmol) is dissolved in methanol (2 mL) and DCM (2 mL). Then 5% palladium on carbon (90 mg, 0.043 mmol) is added. The reaction is stirred for 16 hours under the hydrogen atmosphere. The palladium on carbon is filtered and the filtrate is concentrated to give the crude product. Purification by Gilson preparative HPLC affords 20 mg of the titled product.

TABLE 11

| Example No. | Structure | ES MS M$^+$ + H$^+$ | Retention time (min.) | LCMS Method |
|---|---|---|---|---|
| 38 | 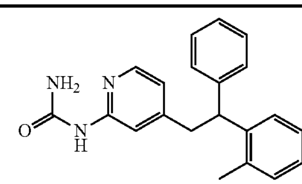 | 332.2 | 0.85 | A |

Example 39

Synthesis of {4-[2-(3-Trifluoromethyl-phenyl)-ethyl]-pyridin-2-yl}-urea

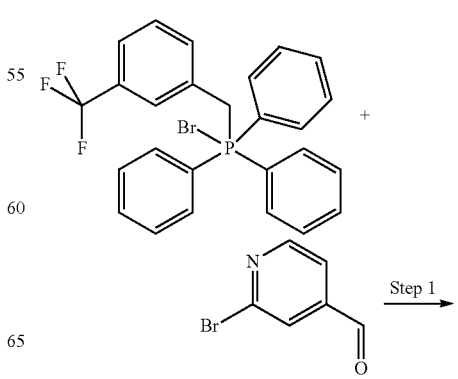

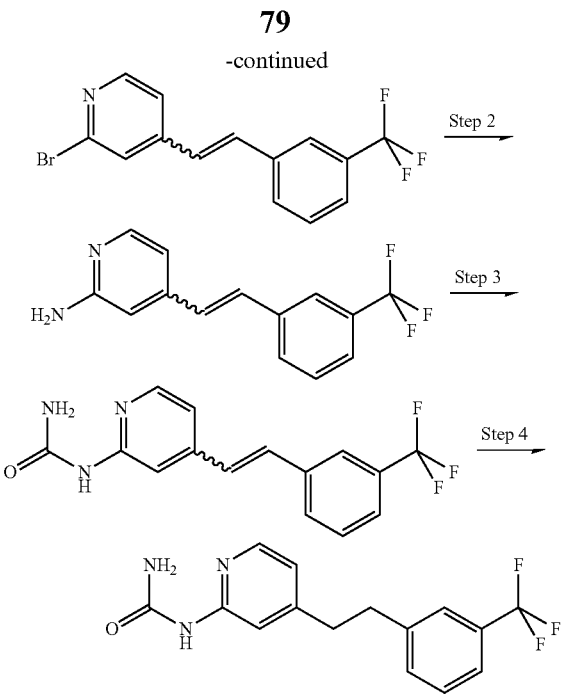

Step 1: Synthesis of 2-Bromo-4-[2-(3-trifluoromethyl-phenyl)-vinyl]-pyridine Triphenyl-(3-trifluoromethyl-benzyl)-phosphonium bromide (808 mg, 1.61 mmol) is dissolved in THF (15 mL) and it is cooled down to −78° C. Then 1.6 M n-BuLi (2.0 mL, 3.2 mmol) is added and the reaction mixture is stirred for 15 min at −78° C. before it is warmed up to room temperature for 30 min. The mixture is cooled down to −78° C. again and 2-bromo-pyridine-4-carbaldehyde (300 mg, 1.61 mmol) is added. The mixture is stirred for 20 min at −78° C. before it is warmed up to room temperature for another 30 min. Saturated NH$_4$Cl aqueous solution (20 mL) is added along with water (45 mL). The mixture is extracted with EtOAc (3×40 mL) and the organic layers are combined and concentrated to give the crude product. Purification by silica flash column chromatography using MeOH in DCM (gradient from 0% to 6%) affords 289 mg of the desired product.

Step 2: Synthesis of 4-[2-(3-Trifluoromethyl-phenyl)-vinyl]-pyridin-2-ylamine 2-Bromo-4-[2-(3-trifluoromethyl-phenyl)-vinyl]-pyridine (289 mg, 0.88 mmol), tris(dibenzylideneacetone)dipalladium(0) (160 mg, 0.18 mmol) and 2-(dicyclohexylphosphino)biphenyl (160 mg, 0.46 mmol) are mixed in dry THF (6 mL). Then Argon is bubbled through the solution for 5 min and 1.0 M LiHMDS (3.1 mL, 3.1 mmol) is added. Then the reaction mixture is heated at 65° C. for 16 hrs before the saturated NH$_4$Cl aqueous solution (20 mL) is added along with water (30 mL). The mixture is extracted with EtOAc (3×35 mL) and the organic layers are combined and concentrated to give the crude product. Purification by silica flash column chromatography using MeOH in DCM (gradient from 0% to 10%) affords 193 mg of the desired product.

Step 3: Synthesis of {4-[2-(3-Trifluoromethyl-phenyl)-vinyl]-pyridin-2-yl}-urea 4-[2-(3-Trifluoromethyl-phenyl)-vinyl]-pyridin-2-ylamine (193 mg, 0.73 mmol) is dissolved in DCM (7 mL) and benzoyl isocynate (215 mg, 1.46 mmol) is added. The reaction is sealed and heated at 50° C. for 16 hrs. Then the solvent is removed and to the residue are added ethanol (7 mL) and potassium carbonate (151 mg, 1.10 mmol). The mixture is heated at 80° C. for 45 min. The solvent is removed and the residue is partitioned between water (45 mL) and EtOAc (55 mL). The aqueous layer is separated and extracted with EtOAc (2×30 mL). The organic layers are combined and concentrated to give the crude product. Purification by silica flash column chromatography using MeOH in DCM (gradient from 0% to 10%) affords 210 mg of the desired product.

Step 4: Synthesis of {4-[2-(3-Trifluoromethyl-phenyl)-ethyl]-pyridin-2-yl}-urea {4-[2-(3-Trifluoromethyl-phenyl)-vinyl]-pyridin-2-yl}-urea (210 mg, 0.68 mmol) is dissolved in methanol (3 mL) and DCM (3 mL). Then 5% palladium on carbon (145 mg, 0.068 mmol) is added. The reaction is stirred for 16 hours under the hydrogen atmosphere. The palladium on carbon is filtered and the filtrate is concentrated to give the crude product. Purification by silica flash column chromatography using MeOH in DCM (gradient from 0% to 10%) affords 71 mg of the titled product.

Example 40 in Table 12 are synthesized according to the procedure for Example 39, substituting either commercially available reagents or the appropriate intermediates described above.

TABLE 12

| Example No. | Structure | ES MS M$^+$ + H$^+$ | Retention time (min.) | LCMS Method |
|---|---|---|---|---|
| 39 | ![structure] | 310.0 | 0.75 | A |
| 40 | ![structure] | 256.4 | 0.68 | A |

Example 41

Synthesis of [4-(1-Hydroxy-1-methyl-2-o-tolyl-ethyl)-pyridin-2-yl]-urea

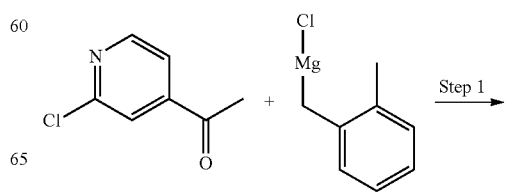

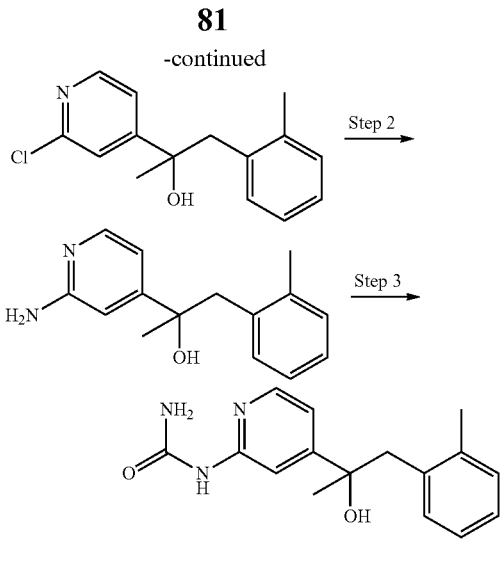

Step 1: Synthesis of 2-(2-Chloro-pyridin-4-yl)-1-o-tolyl-propan-2-ol 1-(2-Chloro-pyridin-4-yl)-ethanone (200 mg, 1.29 mmol) is dissolved in dry THF (10 mL) and it is cooled down to −78° C. Then 0.25 M 2-methylbenzylmagnesium chloride THF solution (5.7 mL, 1.4 mmol) is added and the mixture is stirred for 1.5 hrs at −78° C. After saturated NH₄Cl aqueous solution (10 mL) is added at −78° C., the reaction mixture is warmed up to room temperature. Then water (25 mL) and EtOAc (40 ml) are added and the mixture is stirred for another 10 min. The aqueous layer is separated and extracted with EtOAc (2×20 mL). The organic layers are combined and concentrated to give the crude product. Purification by flash column chromatography using MeOH in DCM (gradient from 0% to 10%) affords 141 mg of desired product.

Step 2: Synthesis of 2-(2-Amino-pyridin-4-yl)-1-o-tolyl-propan-2-ol 2-(2-Chloro-pyridin-4-yl)-1-o-tolyl-propan-2-ol (141 mg, 0.54 mmol), tris(dibenzylideneacetone)dipalladium(0) (99 mg, 0.11 mmol) and 2-(dicyclohexylphosphino)biphenyl (99 mg, 0.28 mmol) are mixed in dry THF (5 mL). Then Argon is bubbled through the solution for 5 min and 1.0 M LiHMDS (2.2 mL, 2.2 mmol) is added. Then the reaction mixture is heated at 65° C. for 16 hrs before the saturated NH₄Cl aqueous solution (10 mL) is added along with water (20 mL). The mixture is extracted with EtOAc (3×25 mL) and the organic layers are combined and concentrated to give the crude product. Purification by silica flash column chromatography using MeOH in DCM (gradient from 0% to 10%) affords 37 mg of the desired product.

Step 3: Synthesis of [4-(1-Hydroxy-1-methyl-2-o-tolyl-ethyl)-pyridin-2-yl]-urea 2-(2-Amino-pyridin-4-yl)-1-o-tolyl-propan-2-ol (37 mg, 0.15 mmol) is dissolved in DCM (1 mL) and benzoyl isocynate (27 mg, 0.18 mmol) is added. The reaction is sealed and heated at 50° C. for 16 hrs. Then the solvent is removed and to the residue are added ethanol (1 mL) and potassium carbonate (32 mg, 0.23 mmol). The mixture is heated at 80° C. for 55 min. The solvent is removed and the residue is partitioned between water (25 mL) and EtOAc (35 mL). The aqueous layer is separated and extracted with EtOAc (2×30 mL). The organic layers are combined and concentrated to give the crude product. Purification by silica flash column chromatography using MeOH in DCM (gradient from 0% to 10%) followed by Gilson preparative HPLC affords 8.2 mg of the titled product.

TABLE 13

| Example No. | Structure | ES MS M⁺ + H⁺ | Retention time (min.) | LCMS Method |
|---|---|---|---|---|
| 41 | (structure) | 286.2 | 0.57 | A |

Example 42

Synthesis of {4-[2-(2-Methoxy-phenyl)-ethyl]-pyridin-2-yl}-urea

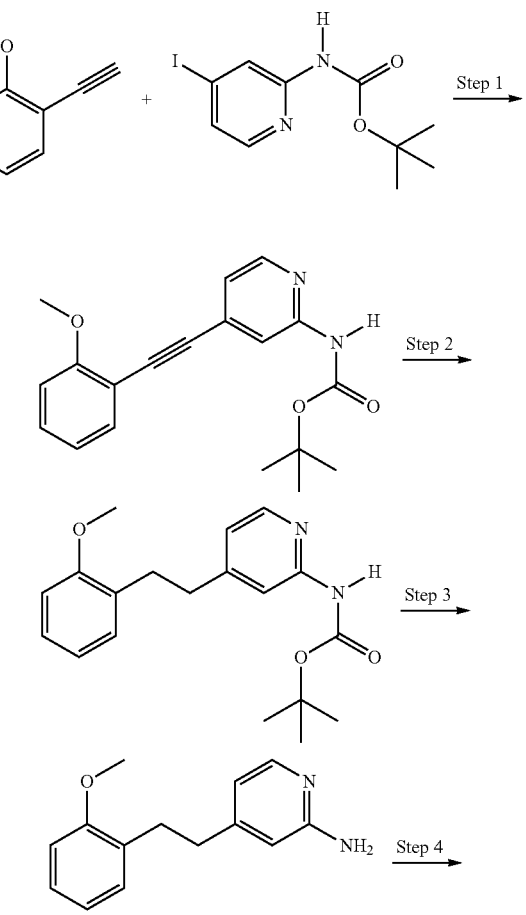

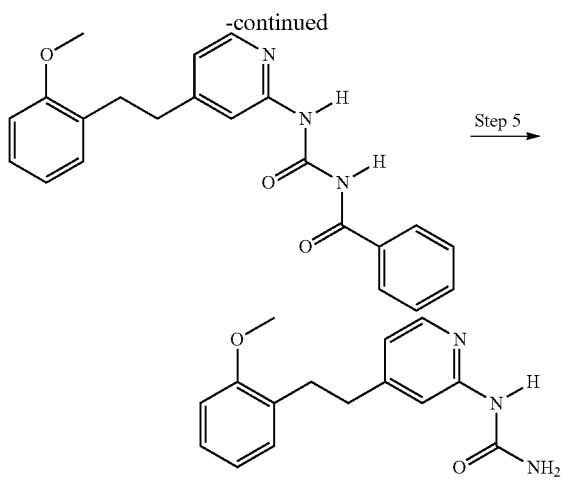

Step 1: Synthesis of [4-(2-methoxy-phenylethynyl)-pyridin-2-yl]-carbamic acid tert-butyl ester A mixture of (4-iodo-pyridin-2-yl)-carbamic acid tert-butyl ester (250.0 mg, 0.781 mmol), 1-ethynyl-2-methoxy-benzene (93.8 mg, 0.710 mmol), CuI (13 mg, 0.071 mmol), Pd(PPh$_3$)$_2$Cl$_2$ (25 mg, 0.036 mmol), and Et$_3$N (9 mL) in dry DMF (3 mL) is stirred at room temperature for 19 hours. The reaction is diluted with ethyl acetate (20 mL) and quenched with saturated aqueous NH$_4$Cl (10 mL). The organic layer is washed with an additional portion of saturated aqueous NH$_4$Cl (10 mL), dried over MgSO$_4$, filtered and concentrated. The residue is purified on SiO$_2$ (0-30% ethyl acetate in heptanes, gradient) to give the product.

Step 2: Synthesis of {4-[2-(2-methoxy-phenyl)-ethyl]-pyridin-2-yl}-carbamic acid tert-butyl ester Methanol (10 mL) and Pd/C (100 mg) are added to a solution of [4-(2-methoxy-phenylethynyl)-pyridin-2-yl]-carbamic acid tert-butyl ester (146 mg, 0.450 mmol) in ethyl acetate (10 mL). The mixture is evacuated and purged with H$_2$ (three times), and stirred at the room temperature under an atmosphere of H$_2$ for 2 hours. The mixture is evacuated and purged with Argon, and filtered through a pad of diatomaceous earth. The filtrate is concentrated to give the crude product, which is used in the next step without purification.

Step 3: Synthesis of 4-[2-(2-methoxy-phenyl)-ethyl]-pyridin-2-ylamine

A solution of {4-[2-(2-methoxy-phenyl)-ethyl]-pyridin-2-yl}-carbamic acid tert-butyl ester (143 mg, 0.435 mmol) in dry CH$_2$Cl$_2$ (3 mL) is treated with trifluoroacetic acid (1.0 mL, 13 mmol), and stirred at room temperature. After 18 hours, the reaction mixture is concentrated and the residue is dissolved in CH$_2$Cl$_2$ (10 mL), extracted with saturated aqueous NaHCO$_3$ (10 mL) and brine (10 mL), dried over MgSO$_4$, filtered and concentrated to give the crude product which is used in the next reaction without purification.

Step 4: Synthesis of 1-benzoyl-3-{4-[2-(2-methoxy-phenyl)-ethyl]-pyridin-2-yl}-urea Benzoyl isocynate (132 mg, 0.896 mmol) is added to a solution of 4-[2-(2-methoxy-phenyl)-ethyl]-pyridin-2-ylamine (93.0 mg, 0.407 mmol) in CH$_2$Cl$_2$ (4 mL), and the mixture is stirred at 60° C. After 20 hours, the mixture is concentrated to give the crude product, which is used in the next step without purification.

Step 5: Synthesis of {4-[2-(2-methoxy-phenyl)-ethyl]-pyridin-2-yl}-urea

Potassium carbonate (93.2 mg, 0.674 mmol) is added to a solution of the crude 1-benzoyl-3-{4-[2-(2-methoxy-phenyl)-ethyl]-pyridin-2-yl}-urea (211 mg) in absolute ethanol (3 mL), and the mixture is heated at 85° C. After 2 hours, the mixture is cooled to room temperature, neutralized with 1 M aqueous HCl to pH 7-8, and stirred over night. The mixture is filtered, and the solids are washed with EtOH (2×0.5 mL) and air dried. The solids are partitioned between ethyl acetate (10 mL) and saturated aqueous NaHCO$_3$ (3 mL). The organic layer is dried over MgSO$_4$, filtered and concentrated to give the titled product.

Examples 43-47 in Table 14 are synthesized according to the procedure for Example 42, substituting either commercially available reagents or the appropriate intermediates described above.

TABLE 14

| Example No. | Structure | ES MS M$^+$ + H$^+$ | Retention time (min.) | LC-MS Method |
|---|---|---|---|---|
| 42 | 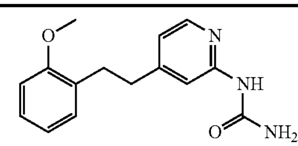 | 272.0 | 1.30 | B |
| 43 | 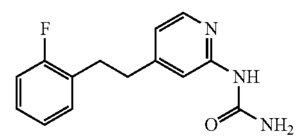 [SMILES: NC(=O)Nc1cc(CCc2ccccc2F)ccn1] | 260.0 | 1.25 | B |
| 44 | 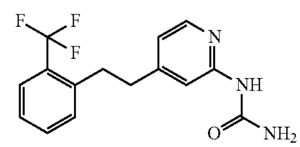 [SMILES: NC(=O)Nc1cc(CCc2ccccc2C(F)(F)F)ccn1] | 310.0 | 1.40 | B |
| 45 | 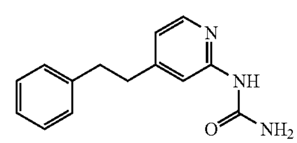 [SMILES: NC(=O)Nc1cc(CCc2ccccc2)ccn1] | 241.6 | 0.53 | A |
| 46 | 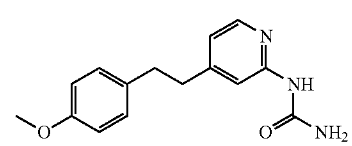 [SMILES: COc1ccc(CCc2ccnc(NC(N)=O)c2)cc1] | 271.5 | 0.60 | A |
| 47 | 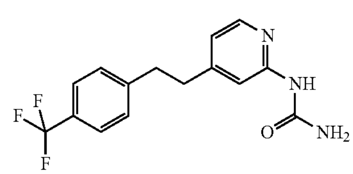 [SMILES: NC(=O)Nc1cc(CCc2ccc(C(F)(F)F)cc2)ccn1] | 309.5 | 0.77 | A |

Example 48

Synthesis of {4-[2-(4-Fluoro-2-methyl-phenyl)-ethyl]-pyridin-2-yl}-urea

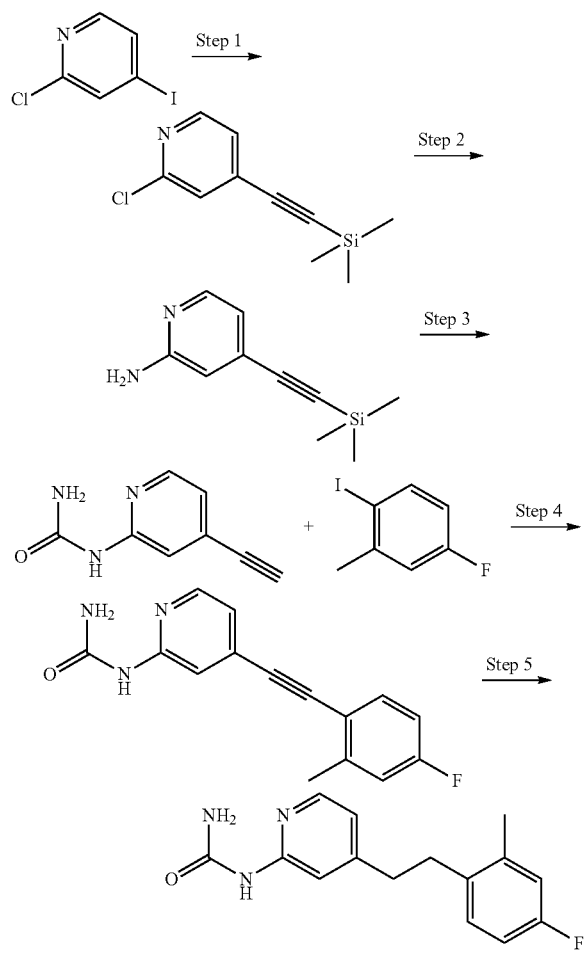

Step 1: Synthesis of 2-Chloro-4-trimethylsilanylethynyl-pyridine

2-Chloro-4-iodo-pyridine (10 g, 42 mmol), palladium bis(triphenylphosphine)dichloride (2.93 g, 4.18 mmol) and triphenylphosphine (1.09 g, 4.17 mmol) are dissolved in de-gased dry THF (10 mL) and triethylamine (42 mL, 301 mmol). The resulting mixture is stirred for 1 hr at room temperature. Then Copper (I) iodide (2.3 g, 12 mmol) and ethynyl-trimethyl-silane (7.1 mL, 50 mmol) are added. The reaction mixture is stirred for 12 hrs at room temperature. The solvents are removed and the residue is diluted with water (100 mL). The mixture is extracted with EtOAc (3×250 mL) and the organic layers are combined, washed with brine, dried over anhydrous $Na_2SO_4$ and concentrated to give the crude product. Purification by silica flash column chromatography using 0.5% EtOAc in hexanes affords 4.6 g of the desired product.

Step 2: Synthesis of 4-Trimethylsilanylethynyl-pyridin-2-ylamine

2-Chloro-4-trimethylsilanylethynyl-pyridine (9.3 g, 44 mmol), tris(dibenzylideneacetone)dipalladium(0) (8.1 g, 8.9 mmol) and 2-(dicyclohexylphosphino)biphenyl (8.1 g, 23 mmol) are added into the de-gased dry THF (60 mL). Then 1.0 M LiHMDS (155 mL, 155 mmol) is added. The reaction mixture is heated at 60° C. for 16 hrs before it is cooled down to room temperature and saturated $NH_4Cl$ aqueous solution (100 mL) is added along with water (100 mL). The mixture is extracted with EtOAc (2×200 mL) and the organic layers are combined and concentrated to give the crude product. Purification by silica flash column chromatography using 33% EtOAc in hexanes affords 7.9 g of the desired product.

Step 3: Synthesis of (4-Ethynyl-pyridin-2-yl)-urea

4-Trimethylsilanylethynyl-pyridin-2-ylamine (7.8 g, 42 mmol) and benzoyl isocynate (12.2 g, 82.9 mmol) are added into DCM (350 mL). The reaction mixture is heated at 50° C. for 16 hrs. Then the solvent is removed and the residue is dissolved in ethanol (350 mL). Potassium carbonate (8.58 g, 62.2 mmol) is added and the mixture is heated at 80° C. for 1 hr. The solvent is removed and the residue is partitioned between water (100 mL) and EtOAc (100 mL). The aqueous layer is separated and extracted with EtOAc (2×100 mL). The organic layers are combined and concentrated to give the crude product. Purification by silica flash column chromatography using 33% EtOAc in hexanes affords 350 mg of the desired product.

Step 4: Synthesis of [4-(4-Fluoro-2-methyl-phenylethynyl)-pyridin-2-yl]-urea (4-Ethynyl-pyridin-2-yl)-urea (75 mg, 0.47 mmol), 4-fluoro-1-iodo-2-methyl-benzene (224 mg, 0.931 mmol), triethylamine (5.0 mL), palladium bis(triphenylphosphine) dichloride (16 mg, 0.023 mmol) and Copper (I) iodide (8.8 mg, 0.047 mmol) are mixed in DMF (1.8 mL). The reaction mixture is stirred for 16 hrs at room temperature before saturated $NH_4Cl$ solution (5 mL) is added along with water (25 mL). The mixture is extracted with EtOAc (3×20 mL) and the organic layers are combined and concentrated to give the crude product. Purification by silica flash column chromatography using MeOH in DCM (gradient from 0% to 5%) affords 25 mg of the desired product.

Step 5: Synthesis of {4-[2-(4-Fluoro-2-methyl-phenyl)-ethyl]-pyridin-2-yl}-urea

[4-(4-Fluoro-2-methyl-phenylethynyl)-pyridin-2-yl]-urea (25 mg, 0.093 mmol) is dissolved in methanol (1.0 mL) and DCM (1.0 mL). Then 5% palladium on carbon (20 mg, 0.0090 mmol) is added. The reaction is stirred for 16 hrs under the hydrogen atmosphere. The palladium on carbon is filtered and the filtrate is concentrated to give the crude product. Methanol (1 mL) is added into the crude and a white solid is formed. The solid is filtered, rinsed with more methanol and dried to give 18 mg of the titled product.

Example 49 in Table 15 is synthesized according to the procedure for Example 48, substituting either commercially available reagents or the appropriate intermediates described above.

TABLE 15

| Example No. | Structure | ES MS M⁺ + H⁺ | Retention time (min.) | LC-MS Method |
|---|---|---|---|---|
| 48 | 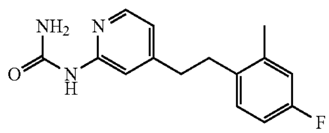 [SMILES: Cc1cc(F)ccc1CCc1ccnc(NC(N)=O)c1] | 273.8 | 0.70 | A |
| 49 | 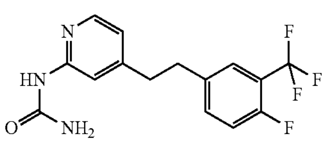 [SMILES: NC(=O)Nc1cc(CCc2ccc(F)c(C(F)(F)F)c2)ccn1] | 328.2 | 0.71 | A |

Example 50

Synthesis of {4-[5-(4-Fluoro-phenyl)-3-methyl-3H-imidazol-4-yl]-pyridin-2-yl}-urea

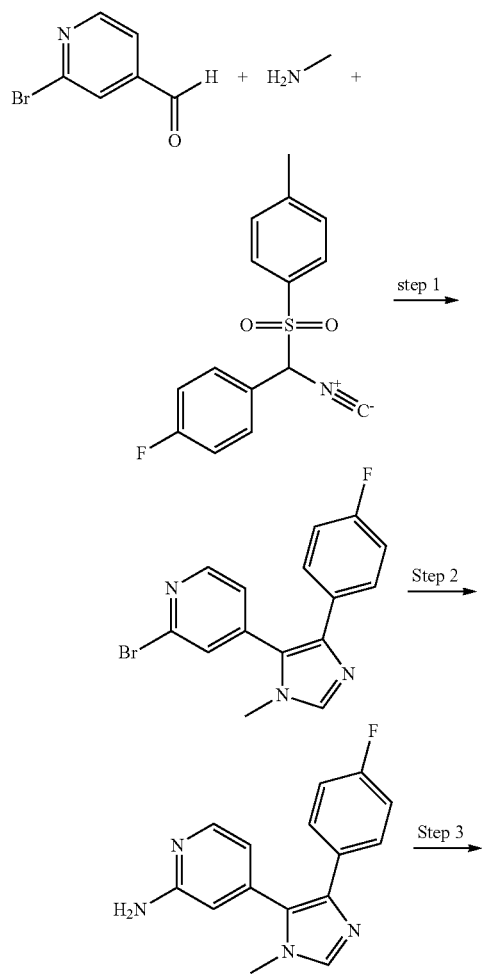

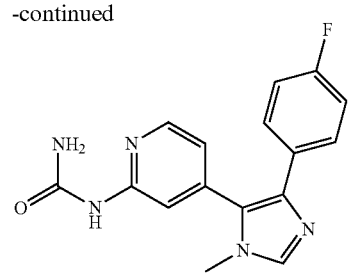

Step 1: Synthesis of 2-Bromo-4-[5-(4-fluoro-phenyl)-3-methyl-3H-imidazol-4-yl]-pyridine 2-Bromo-pyridine-4-carbaldehyde (479 mg, 2.58 mmol) and 2.0 M methylamine THF solution (1.73 mL, 3.46 mmol) are mixed in THF (6.0 mL) and the reaction mixture is stirred for 4 hrs at room temperature. Then piperazine (224 mg, 2.58 mmol) and [1-(4-fluorophenyl)-1-tosyl]methylisocyanide (500 mg, 1.73 mmol) are added. The reaction mixture is stirred for another 16 hrs before water (35 mL) is added. The resulting mixture is extracted with EtOAc (3×35 mL) and the organic layers are combined, washed with saturated NaHCO₃ aqueous solution (20 ml) and water (25 mL), dried and concentrated to give the crude product. Purification by silica flash column chromatography using EtOAc in heptane (gradient from 20% to 90%) affords 460 mg of desired product.

Step 2: Synthesis of 4-[5-(4-Fluoro-phenyl)-3-methyl-3H-imidazol-4-yl]-pyridin-2-ylamine 2-Bromo-4-[5-(4-fluoro-phenyl)-3-methyl-3H-imidazol-4-yl]-pyridine (460 mg, 1.39 mmol), tris(dibenzylideneacetone)dipalladium(0) (254 mg, 0.28 mmol) and 2-(dicyclohexylphosphino)biphenyl (252 mg, 0.72 mmol) are mixed in dry THF (10 mL). Then Argon is bubbled through the solution for 5 min and 1.0 M LiHMDS (4.8 mL, 4.8 mmol) is added. Then the reaction mixture is heated at 65° C. for 16 hrs before the saturated NH₄Cl aqueous solution (20 mL) is added along with water (25 mL). The mixture is extracted with EtOAc (3×50 mL) and the organic layers are combined and concentrated to give the crude product. Purification by silica flash column chromatography using MeOH in DCM (gradient from 0% to 10%) followed by Gilson preparative HPLC affords 15 mg of desired product.

Step 3: Synthesis of {4-[5-(4-Fluoro-phenyl)-3-methyl-3H-imidazol-4-yl]-pyridin-2-yl}-urea 4-[5-(4-Fluoro-phenyl)-3-methyl-3H-imidazol-4-yl]-pyridin-2-ylamine (13 mg, 0.048 mmol) and benzoyl isocynate (8.6 mg, 0.058 mmol) are mixed in DCM (0.5 mL). The reaction is sealed and heated at 50° C. for 16 hrs. Then the solvent is removed and to the residue are added ethanol (0.5 mL) and potassium carbonate (10 mg, 0.073 mmol). The mixture is then heated at 80° C. for 45 min. The solvent is removed and the residue is partitioned between water (35 mL) and EtOAc (55 mL). The aqueous layer is separated and extracted with EtOAc (2×30 mL). The organic layers are combined and concentrated to give the crude product. The crude is recrystallized in DCM to give 15 mg of the titled product.

Example 51 in Table 16 is synthesized according to the procedure for Example 50, substituting either commercially available reagents or the appropriate intermediates described above.

TABLE 16

| Example No. | Structure | ES MS M+ + H+ | Retention time (min.) | LCMS Method |
|---|---|---|---|---|
| 50 | 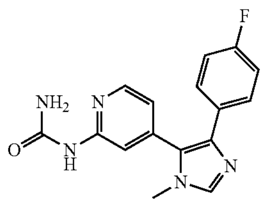 [SMILES: Cn1cnc(-c2ccc(F)cc2)c1-c1ccnc(NC(N)=O)c1] | 312.4 | 0.41 | A |
| 51 | 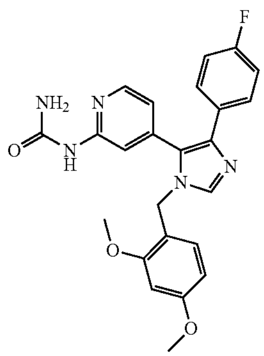 [SMILES: COc1ccc(Cn2cnc(-c3ccc(F)cc3)c2-c2ccnc(NC(N)=O)c2)c(OC)c1] | 448.2 | 0.62 | A |

Example 52

Synthesis of {4-[5-(4-Fluoro-phenyl)-3H-imidazol-4-yl]-pyridin-2-yl}-urea

Step 1: Synthesis of {4-[5-(4-Fluoro-phenyl)-3H-imidazol-4-yl]-pyridin-2-yl}-urea To the solution of {4-[3-(2,4-Dimethoxy-benzyl)-5-(4-fluoro-phenyl)-3H-imidazol-4-yl]-pyridin-2-yl}-urea (Example 51, 15 mg, 0.034 mmol) in DCM (1.0 mL) is added trifluoroacetic acid (0.1 mL). The reaction mixture is stirred for 6.5 days at room temperature before saturated NaHCO₃ aqueous solution (2 mL) is added along with water (10 ml). The mixture is extracted with EtOAc (3×20 mL) and the organic layers are combined, dried and concentrated to give the crude product. Purification by silica flash column chromatography using 10% MeOH in DCM affords 9.7 mg of the titled product.

TABLE 17

| Example No. | Structure | ES MS M+ + H+ | Retention time (min.) | LCMS Method |
|---|---|---|---|---|
| 52 | 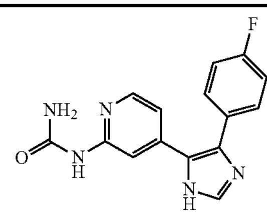 | 298.1 | 0.39 | A |

Example 53

Synthesis of {4-[5-(4-Fluoro-phenyl)-1-methyl-1H-imidazol-4-yl]-pyridin-2-yl}-urea

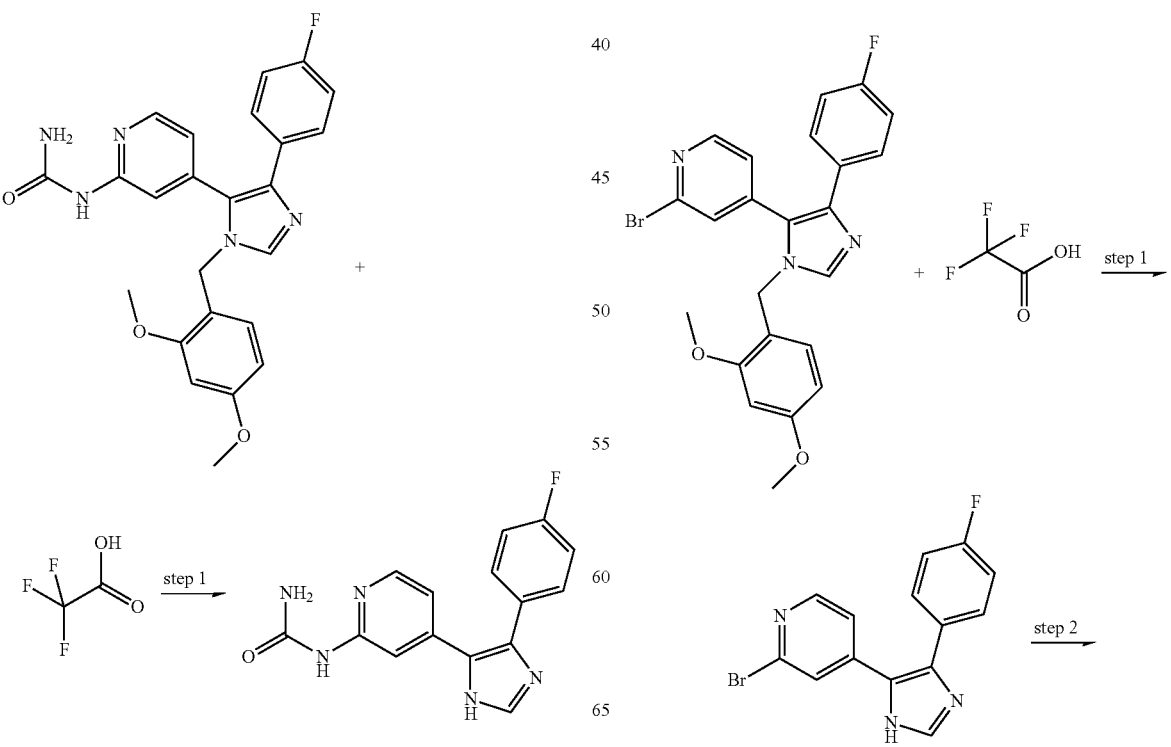

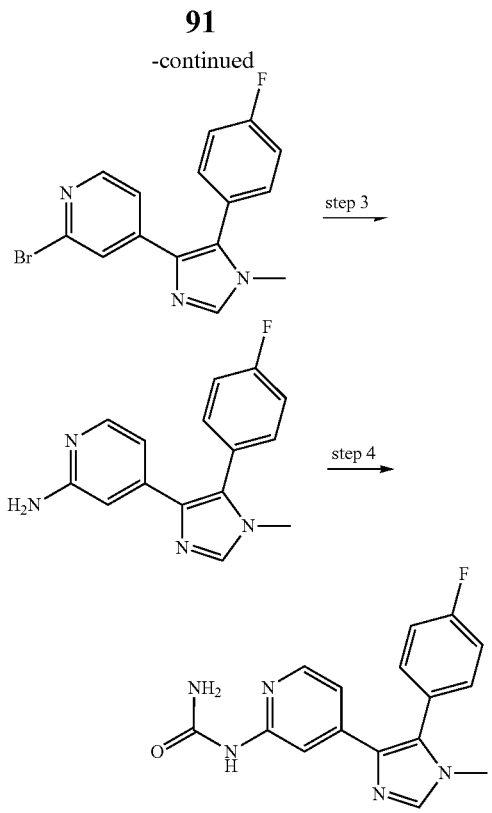

2-Bromo-4-[3-(2,4-dimethoxy-benzyl)-5-(4-fluoro-phenyl)-3H-imidazol-4-yl]-pyridine is synthesized according to the procedure described in Example 50.

Step 1: Synthesis of 2-Bromo-4-[5-(4-fluoro-phenyl)-3H-imidazol-4-yl]-pyridine

2-Bromo-4-[3-(2,4-dimethoxy-benzyl)-5-(4-fluoro-phenyl)-3H-imidazol-4-yl]-pyridine (720 mg, 1.54 mmol) is dissolved in DCM (12 mL) and trifluoroacetic acid (3.0 mL) is added at room temperature. The mixture is stirred for 60 hrs before saturated NaHCO₃ aqueous solution is used to adjust the pH to about 7.5. Then the mixture is extracted with EtOAc (3×30 mL). The organic layers are combined and concentrated to give the crude product. The crude is purified by silica flash column chromatography using MeOH in DCM (gradient from 0% to 10%) to give 316 mg of desired product.

Step 2: Synthesis of 2-Bromo-4-[5-(4-fluoro-phenyl)-1-methyl-1H-imidazol-4-yl]-pyridine 2-Bromo-4-[5-(4-fluoro-phenyl)-3H-imidazol-4-yl]-pyridine (250 mg, 0.79 mmol) is dissolved in DMF (5.0 mL) and 60% NaH (38 mg, 0.94 mmol) is added. The mixture is stirred for 30 min and methyl iodide (0.098 mL, 1.6 mmol) is added. The reaction is continued for another 1.5 hrs before Saturated NH₄Cl aqueous solution (10 mL) is added. The resulting mixture is extracted with EtOAc (3×25 mL). The organic layers are combined and concentrated to give the crude product which is used in the next step without purification.

Step 3: Synthesis of 4-[5-(4-Fluoro-phenyl)-1-methyl-1H-imidazol-4-yl]-pyridin-2-ylamine The crude 2-Bromo-4-[5-(4-fluoro-phenyl)-1-methyl-1H-imidazol-4-yl]-pyridine (196 mg), 28% aqueous ammonium hydroxide solution (2.0 mL) and copper (I) oxide (84 mg, 0.59 mmol) are mixed in 1,4-dioxane (3.0 mL) in a microwave reaction tube. The mixture is heated at 150° C. for 25 min in a microwave reactor before water (30 mL) is added. The resulting mixture is extracted with EtOAc (3×25 ml). The organic layers are combined and concentrated to give the crude product. Purification by silica flash column chromatography using MeOH in DCM (gradient from 0% to 10%) affords 72 mg of desired product.

Step 4: Synthesis of {4-[5-(4-Fluoro-phenyl)-1-methyl-1H-imidazol-4-yl]-pyridin-2-yl}-urea 4-[5-(4-Fluoro-phenyl)-1-methyl-1H-imidazol-4-yl]-pyridin-2-ylamine (72 mg, 0.27 mmol) and benzoyl isocynate (59 mg, 0.40 mmol) are mixed in DCM (2.0 mL). The reaction is sealed and heated at 50° C. for 16 hrs. Then the solvent is removed and to the residue are added ethanol (2.0 mL) and potassium carbonate (56 mg, 0.40 mmol). The mixture is then heated at 80° C. for 35 min. The solvent is removed and the residue is partitioned between water (35 mL) and EtOAc (45 mL). The aqueous layer is separated and extracted with EtOAc (2×30 mL). The organic layers are combined and concentrated to give the crude product. The crude is washed with methanol (3×5 mL) and dried to give 55 mg of the titled product.

TABLE 18

| Example No. | Structure | ES MS M⁺ + H⁺ | Retention time (min.) | LCMS Method |
|---|---|---|---|---|
| 53 | 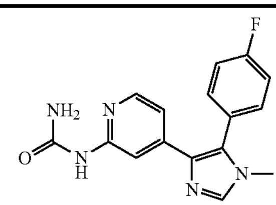 | 311.9 | 0.57 | A |

Example 54

Synthesis of {4-[4-(4-Fluoro-phenyl)-oxazol-5-yl]-pyridin-2-yl}-urea

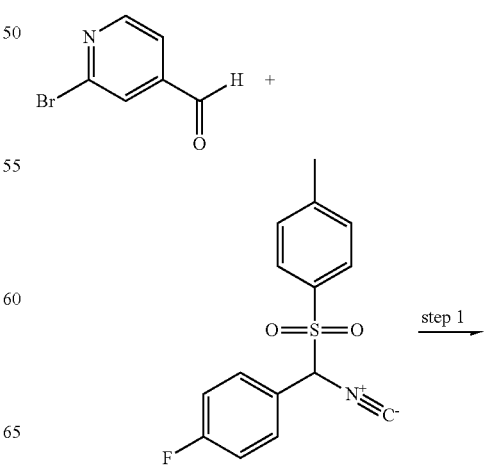

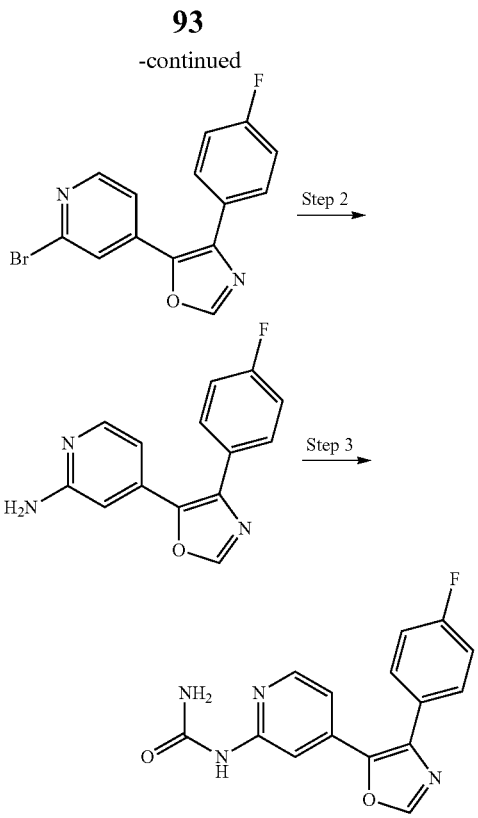

Step 1: Synthesis of 2-Bromo-4-[4-(4-fluoro-phenyl)-oxazol-5-yl]-pyridine

2-Bromo-pyridine-4-carbaldehyde (958 mg, 5.15 mmol), 28% aqueous ammonium hydroxide solution (2.01 mL, 15.5 mmol), piperazine (448 mg, 5.15 mmol) and [1-(4-fluorophenyl)-1-tosyl]methylisocyanide (1.0 g, 3.5 mmol) are mixed in THF (15 mL). The reaction mixture is stirred for 16 hrs at room temperature. Then water (35 mL) is added and the mixture is extracted with EtOAc (3×25 mL). The organic layers are combined, washed with saturated NaHCO₃ aqueous solution (20 mL) and water (25 mL), dried and concentrated to give the crude product. Purification by silica flash column chromatography using EtOAc in heptane (gradient from 10% to 80%) affords 748 mg of desired product.

Step 2: Synthesis of 4-[4-(4-Fluoro-phenyl)-oxazol-5-yl]-pyridin-2-ylamine

2-Bromo-4-[4-(4-fluoro-phenyl)-oxazol-5-yl]-pyridine (700 mg, 2.19 mmol), 28% aqueous ammonium hydroxide solution (14 mL) and Copper (I) oxide (314 mg, 2.19 mmol) are mixed in 1,4-dioxane (14 mL) in a microwave reaction tube. The tube is sealed and heated at 150° C. for 25 min in a microwave reactor. Then water (80 mL) is added and the mixture is extracted with EtOAc (3×50 ml). The organic layers are combined and concentrated to give the crude product. Purification by silica flash column chromatography using MeOH in DCM (gradient from 0% to 10%) affords 320 mg of desired product.

Step 3: Synthesis of {4-[4-(4-Fluoro-phenyl)-oxazol-5-yl]-pyridin-2-yl}-urea 4-[4-(4-Fluoro-phenyl)-oxazol-5-yl]-pyridin-2-ylamine (57 mg, 0.22 mmol) and benzoyl isocynate (39 mg, 0.27 mmol) are mixed in DCM (2.0 mL). The reaction is sealed and heated at 50° C. for 16 hrs. Then the solvent is removed and to the residue are added ethanol (2.0 mL) and potassium carbonate (46 mg, 0.34 mmol). The mixture is then heated at 80° C. for 55 min. The solvent is removed and the residue is partitioned between water (25 mL) and EtOAc (35 mL). The aqueous layer is separated and extracted with EtOAc (2×30 mL). The organic layers are combined and concentrated to give the crude product. EtOAc (2 mL) is added into the crude and a solid is formed. The solid is filtered, rinsed with more EtOAc and dried to give 40 mg of the titled product.

TABLE 19

| Example No. | Structure | ES MS M⁺ + H⁺ | Retention time (min.) | LCMS Method |
|---|---|---|---|---|
| 54 | 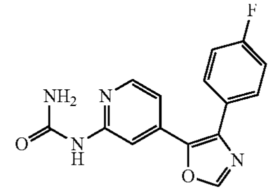 [SMILES: NC(=O)Nc1cc(-c2ocnc2-c2ccc(F)cc2)ccn1] | 299.3 | 0.64 | A |

Example 55

Synthesis of {4-[2-(4-Fluoro-phenyl)-pyrrolidin-1-yl]-pyridin-2-yl}-urea

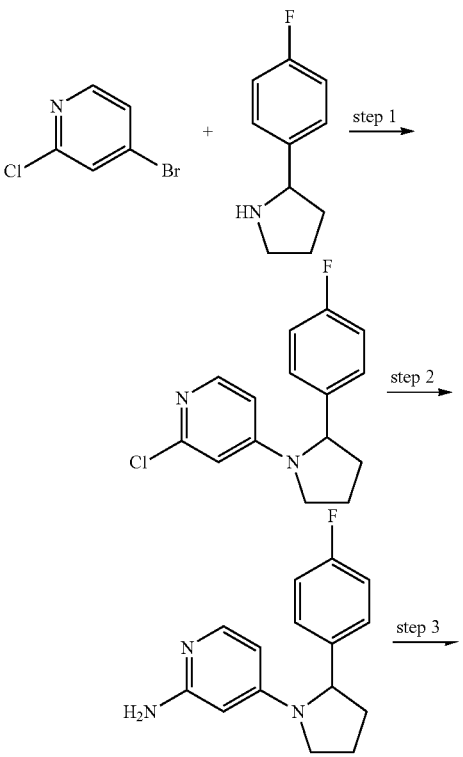

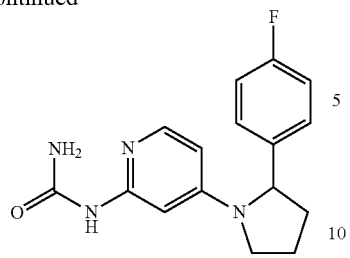

Step 1: Synthesis of 2-Chloro-4-[2-(4-fluoro-phenyl)-pyrrolidin-1-yl]-pyridine

4-Bromo-2-chloro-pyridine (0.17 mL, 1.5 mmol), 2-(4-fluoro-phenyl)-pyrrolidine (250 mg, 1.5 mmol) and triethylamine (0.22 mL, 1.6 mmol) are mixed in DMSO (5.0 mL). The reaction mixture is heated at 120° C. for 30 min and 200° C. for 40 min in a microwave reactor. Then water (35 mL) is added and the mixture is extracted with EtOAc (3×30 mL). The organic layers are combined, washed with water (3×20 mL) and concentrated to give the crude product. Purification by silica flash column chromatography using EtOAc in heptane (gradient from 10% to 90%) followed by Gilson preparative HPLC affords 240 mg of desired product.

Step 2: Synthesis of 4-[2-(4-Fluoro-phenyl)-pyrrolidin-1-yl]-pyridin-2-ylamine

2-Chloro-4-[2-(4-fluoro-phenyl)-pyrrolidin-1-yl]-pyridine (97 mg, 0.35 mmol), tris(dibenzylideneacetone)dipalladium(0) (32 mg, 0.035 mmol) and 2-(dicyclohexylphosphino)biphenyl (25 mg, 0.070 mmol) are mixed in dry THF (2.0 mL). Then Argon is bubbled through the solution for 5 min and 1.0 M LiHMDS (0.53 mL, 0.53 mmol) is added. Then the reaction mixture is heated at 65° C. for 6 hrs before more 1.0 M LiHMDS (0.53 mL, 0.53 mmol) is added. The resulting mixture is heated at 65° C. for another 16 hrs. Then saturated $NH_4Cl$ aqueous solution (20 mL) is added along with water (25 mL). The mixture is extracted with EtOAc (3×50 mL) and the organic layers are combined and concentrated to give the crude product. Purification by silica flash column chromatography using MeOH in DCM (gradient from 0% to 10%) followed by Gilson preparative HPLC affords 61 mg of desired product.

Step 3: Synthesis of {4-[2-(4-Fluoro-phenyl)-pyrrolidin-1-yl]-pyridin-2-yl}-urea 4-[2-(4-Fluoro-phenyl)-pyrrolidin-1-yl]-pyridin-2-ylamine (61 mg, 0.24 mmol) and benzoyl isocynate (52 mg, 0.36 mmol) are mixed in DCM (2.0 mL). The reaction is sealed and heated at 50° C. for 16 hrs. Then the solvent is removed and to the residue are added ethanol (2.0 mL) and potassium carbonate (49 mg, 0.36 mmol). The mixture is then heated at 80° C. for 45 min. The solvent is removed and the residue is partitioned between water (35 mL) and EtOAc (55 mL). The aqueous layer is separated and extracted with EtOAc (2×30 mL). The organic layers are combined and concentrated to give the crude product. Purification by silica flash column chromatography using MeOH in DCM (gradient from 0% to 10%) followed by re-crystallization from DCM/heptane affords 40 mg of the titled product.

TABLE 20

| Example No. | Structure | ES MS $M^+ + H^+$ | Retention time (min.) | LCMS Method |
|---|---|---|---|---|
| 55 | 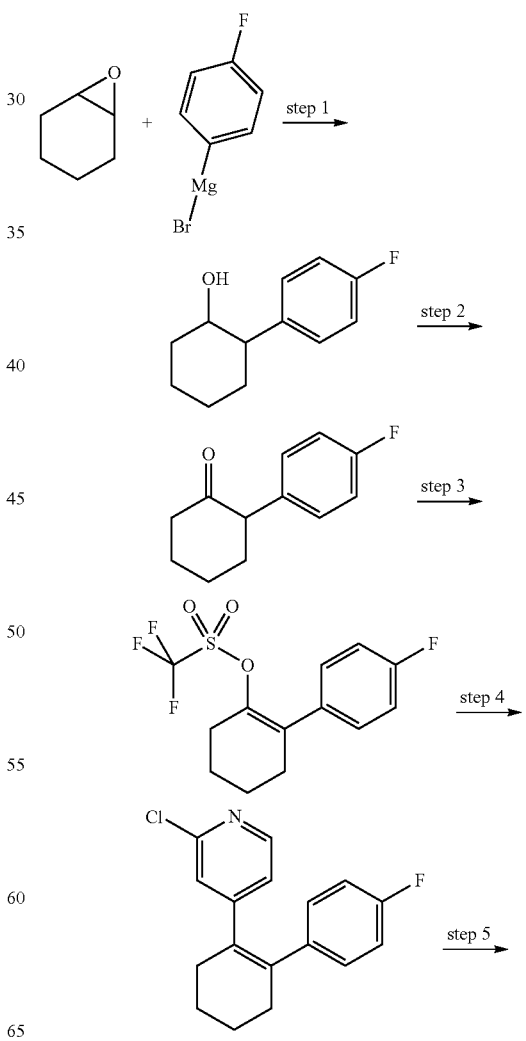 | 301.5 | 0.54 | A |

Example 56

{4-[2-(4-Fluoro-phenyl)-cyclohex-1-enyl]-pyridin-2-yl}-urea

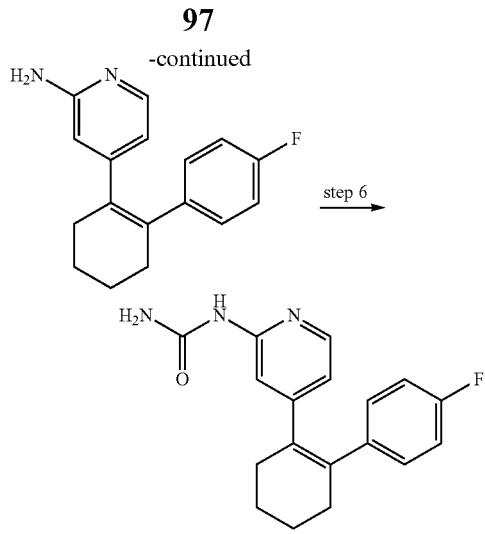

step 6

Step 1: Synthesis of 2-(4-Fluoro-phenyl)-cyclohexanol

To a cooled solution of 4-Fluorophenylmagnesium bromide (1.0 M in THF, 4.94 mL, 4.94 mmol) in dry THF (10 mL) at −78° C. is added Copper (I) Bromide Dimethylsulfide complex (51 mg, 0.25 mmol) and the resulting mixture is stirred at −78° C. for 10 min, followed by the slow addition of a solution of 7-Oxa-bicyclo[4.1.0]heptane (500 µL, 4.94 mmol) in THF (2 mL). The reaction is warmed to 0° C. and is stirred for 2 hour. Then the reaction is quenched with saturated $NH_4Cl$ solution (20 mL). The resulting mixture is extracted with EtOAc (10 mL×3). The organic layers are combined, washed with brine (10 mL×1), dried over anhydrous sodium sulfate and concentrated under reduced pressure. The crude is purified by silica flash column chromatography using EtOAc in Heptane (gradient from 0% to 35%) to give 700 mg of desired product.

Step 2: Synthesis of 2-(4-Fluoro-phenyl)-cyclohexanone

To a solution of oxalyl chloride (0.45 mL, 5.2 mmol) in dry dichloromethane (15 mL) at −78° C. is added a solution of DMSO (0.73 mL, 10.3 mmol) in dichloromethane (10 mL) dropwise, and the resulting mixture is allowed to stir at −78° C. for 30 minutes. Then a solution of 2-(4-Fluoro-phenyl)-cyclohexanol (500 mg, 2.57 mmol) in dichloromethane (5 mL) is added and stirred for 15 minutes. Then triethylamine (2.87 mL, 15.4 mmol) is added and the reaction is allowed to slowly warm up to 20° C. and stirred for 16 hours. The mixture is poured into ice-water (30 mL) and organic layer is washed with water (10 mL×5), then brine (10 mL×1) and dried over anhdrous sodium sulfate. After concentration, the crude is purified by silica flash column chromatography using EtOAc in Heptane (gradient from 0% to 30%) to give 342 mg of the desired product.

Step 3: Synthesis of Trifluoro-methanesulfonic acid 2-(4-fluoro-phenyl)-cyclohex-1-enyl ester 2-(4-Fluoro-phenyl)-cyclohexanone (200 mg, 1.04 mmol) is added to the mixture of 60% NaH (166 mg, 4.16 mmol) in DMF (5 mL) at 0° C. The mixture is warmed to 20° C. and stirred for 30 min. Then 1,1,1-trifluoro-N-phenyl-N-(trifluoromethylsulfonyl)methanesulfonamide (743 mg, 4.16 mmol) is added and the reaction mixture is stirred for 6 hours before it is treated with water (20 mL) and ethyl acetate (30 mL). The organic extract is washed with water (20 mL×1) and brine solution (20 mL×1), and dried over anhydrous sodium sulfate. After concentration, the crude is purified by silica flash column chromatography using EtOAc in Heptane (gradient from 0% to 25%) to give 220 mg of the desired product.

Step 4: Synthesis of 2-Chloro-4-[2-(4-fluoro-phenyl)-cyclohex-1-enyl]-pyridine Trifluoro-methanesulfonic acid 2-(4-fluoro-phenyl)-cyclohex-1-enyl ester (200 mg, 0.62 mmol), 2-Chloro-4-(4,4,5,5-tetramethyl-[1,3,2]dioxaborolan-2-yl)-pyridine (162 mg, 0.68 mmol), Bis(triphenylphosphine)Palladium (II) dichloride (43 mg, 0.062 mmol), Sodium Carbonate solution (2.0 M, 1.54 mL, 3.1 mmol) and DMF (3 mL) are mixed in a 5 mL microwave tube with a stir bar and the mixture is heated to 100° C. in microwave reactor for 30 min. The mixture is poured to water (10 mL) and extracted with EtOAc (10 mL×3). The organic extracts are washed with water (20 mL×1), brine (20 mL×1) and dried over anhydrous sodium sulfate. After concentration, the crude is purified by silica flash column chromatography using EtOAc in Heptane (gradient from 0% to 20%) to give 104 mg of the desired product.

Step 5: Synthesis of 4-[2-(4-Fluoro-phenyl)-cyclohex-1-enyl]-pyridin-2-ylamine A sealed 8 mL vial is charged with 2-Chloro-4-[2-(4-fluoro-phenyl)-cyclohex-1-enyl]-pyridine (25 mg, 0.087 mmol), Tris(dibenzyldieneacetone)Dipalladium (15.9 mg, 0.017 mmol) and 2-(dicyclohexylphosphino)biphenyl (15.8 mg, 0.045 mmol) in dry THF (3 mL). Argon is bubbled through the mixture for 5 min. Additional THF (1 mL) and LiHMDS (1.0 M in toluene, 0.26 mL, 0.26 mmol) are added. And the resulting mixture is allowed to stir at 65° C. for 1 hour. To the mixture is added saturated ammonium chloride solution and extracted with EtOAc (10 mL×3). The organic extract are washed with water (10 mL×1) and brine (10 mL×1), and dried over anhydrous sodium sulfate. After concentration, the crude is purified by silica flash column chromatography using MeOH in DCM (gradient from 0% to 10%) to give 11 mg of the desired product.

Step 6: Synthesis of {4-[2-(4-Fluoro-phenyl)-cyclohex-1-enyl]-pyridin-2-yl}-urea A sealed 8 mL vial is charged with a solution of 4-[2-(4-Fluoro-phenyl)-cyclohex-1-enyl]-pyridin-2-ylamine (11 mg, 0.041 mmol) in methylene chloride (2 mL). Then benzoyl isocynate (9.0 mg, 0.06 mmol) is added. The resulting mixture is allowed to stir at 50° C. for 1 hour. The solvent is then carefully removed before potassium carbonate (6.8 mg, 0.049 mmol) and ethanol (1 mL) are added. The resulting reaction is allowed to stir at 85° C. for 30 min. Solvent is removed and the crude is purified by silica flash column chromatography using MeOH in DCM (gradient from 0% to 5%) to give 11 mg of the titled product.

TABLE 21

| Example No. | Structure | ES MS M⁺ + H⁺ | Retention time (min.) | LCMS Method |
|---|---|---|---|---|
| 56 | H₂N-C(=O)-NH-pyridinyl-cyclohexenyl-C₆H₄F | 312.2 | 0.87 | A |

Example 57

{4-[cis-2-(4-Fluoro-phenyl)-cyclohex-1-enyl]-pyridin-2-yl}-urea

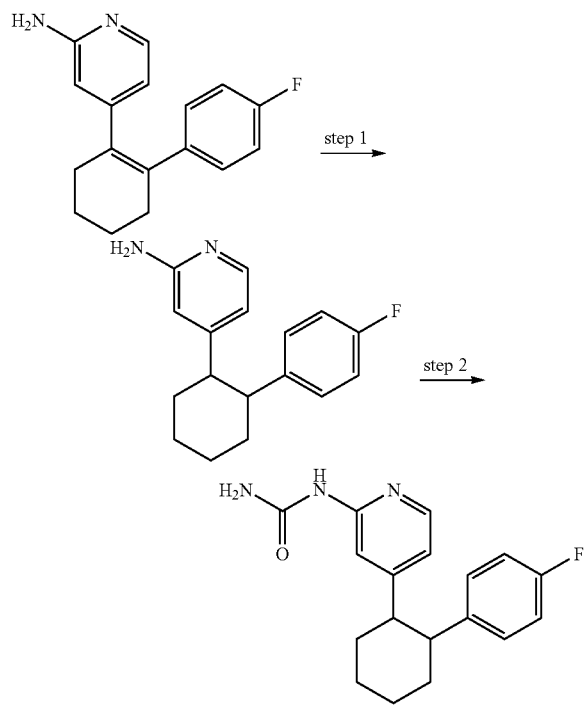

Step 1: Synthesis of 4-[cis-2-(4-Fluoro-phenyl)-cyclohexyl]-pyridin-2-ylamine

A solution of 4-[2-(4-Fluoro-phenyl)-cyclohex-1-enyl]-pyridin-2-ylamine (220 mg, 0.82 mmol, synthesis described in example 56) in methanol (10 mL) is passed through H-Cube® Continuous-flow Hydrogenation Reactor at 60° C. and under 60 psi hydrogen pressure. The 10% Pd/C cartridge is used and the reaction is run for 48 hours. The solvent is removed to give 120 mg of the desired product.

Step 2: Synthesis of {4-[cis-2-(4-Fluoro-phenyl)-cyclohex-1-enyl]-pyridin-2-yl}-urea A sealed 8 mL vial is charged with a solution of 4-[cis-2-(4-Fluoro-phenyl)-cyclohexyl]-pyridin-2-ylamine (90 mg, 0.33 mmol) in methylene chloride (2 mL). Then benzoyl isocynate (74 mg, 0.50 mmol) is added. The resulting mixture is allowed to stir at 50° C. for 1 hour. The solvent is then carefully removed before potassium carbonate (55 mg, 0.40 mmol) and ethanol (2 mL) are added. The resulting reaction is allowed to stir at 85° C. for 30 min Solvent is removed and the crude is purified by Gilson preparative HPLC to give 30 mg of the titled product.

TABLE 22

| Example No. | Structure | ES MS M⁺ + H⁺ | Retention time (min.) | LCMS Method |
|---|---|---|---|---|
| 57 | H₂N-C(=O)-NH-pyridinyl-cyclohexyl-C₆H₄F | 314.4 | 0.78 | A |

Assessment of Biological Properties

The biological properties of the compounds of the invention can be assessed using the in vitro assays described below.

Method 1: MR Competitive Molecular Binding Assay

The MR competitive binding assay is based on the binding and displacement of a TAMRA-labeled Dexamethasone probe with fluorescence polarization (FP) detection. The assay is performed in 384-well, low volume NBS black plates (Corning #3676) in assay buffer consisting of 10 mM TES, pH 7.4, 50 mM KCl, 20 mM Sodium molybdate, 1.5 mM EDTA, 0.04% CHAPS, 10% Glycerol and 1 mM DTT. Full Length human mineralocorticoid receptor (hMR) present in a baculovirus infected insect cell lysate is diluted 2 fold in assay buffer and 10 μL of this dilution is added to the assay plate. Blank wells receive 10 μL of the diluted MR lysate containing 3 μM Dexamethasone. 2 μL diluted test compound is transferred to the assay plate for a final starting top concentration of 10 μM in 1% DMSO. Blank and positive control wells receive no test compound. The reaction is started by adding 3 μL of 25 nM probe in assay buffer for a final assay concentration of 5 nM. After 60 minutes of incubation at RT, the plate is read on Analyst using 550 nm excitation filter, 580 nm emission filter and RH-561 dichroic minor. The mP signals are converted to percent of control (POC) values using the formula:

$$POC=100*(Signal-BCTRL)+(PCTRL-BCTRL)$$

where Signal is the test well signal, BCTRL is the average of background (negative control) well signals on the plate and PCTRL is the average of positive control well signals on the plate. For the concentration-responsive compounds, POC as a function of test compound concentration is fitted to a 4-parameter logistic equation of the form:

$$Y=A+(B-A)/[1+(x/C)D]$$

where A, B, C, and D are fitted parameters (parameter B is fixed at zero POC), and x and y are the independent and dependent variables, respectively. The $IC_{50}$ is determined as the inflection point parameter, C.

Compounds according to the invention were assayed in accordance with above described method yielding $IC_{50}$ values shown in Table 23 below.

TABLE 23

IC50 value of MR binding assay

| Compound of Example | MR Binding IC50 nM |
|---|---|
| 1 | 47 |
| 2 | 130 |
| 3 | 4200 |
| 4 | 62 |
| 5 | 670 |
| 6 | 1100 |
| 7 | 280 |
| 8 | 790 |
| 9 | 6100 |
| 10 | 7900 |
| 11 | 1800 |
| 12 | 38 |
| 13 | 160 |
| 14 | 14 |
| 15 | 190 |
| 16 | 9.4 |
| 17 | >10000 |
| 18 | 25 |
| 19 | 310 |
| 20 | 300 |
| 21 | 7800 |
| 22 | 2400 |
| 23 | 190 |
| 24 | 7.1 |
| 25 | 30 |
| 26 | 86 |
| 27 | 1600 |
| 28 | 480 |
| 29 | 7100 |
| 30 | >10000 |
| 31 | 13 |
| 32 | 11 |
| 33 | 22 |
| 34 | 6800 |
| 35 | 33 |
| 36 | 100 |
| 37 | 1800 |
| 38 | 54 |
| 39 | 73 |
| 40 | 78 |
| 41 | 1700 |
| 42 | 25 |
| 43 | 76 |
| 44 | 13 |
| 45 | 37 |
| 46 | 160 |
| 47 | 100 |
| 48 | 4.7 |
| 49 | 330 |
| 50 | 130 |
| 51 | 330 |
| 52 | 850 |
| 53 | 3400 |
| 54 | 110 |
| 55 | 2700 |
| 56 | 140 |
| 57 | 270 |

Method 2: Cell-Based MR Antagonism Functional Assay:

MR-UAS-bla HEK 293T cells contain the ligand-binding domain (LBD) of the human Mineralcorticoid Receptor fused to the DNA binding domain of GAL4 stably integrated in the GeneBLAzer® UAS-bla HEK 293 cell line. GeneBLAzer® UAS-bla HEK 293T cells stably express a beta-lactamase reporter gene under the transcriptional control of an upstream activator sequence (UAS). When an agonist binds to the LBD of the GAL4 (DBD)-MR (LBD) fusion protein, the protein binds to the UAS, resulting in expression of beta-lactamase. Compounds are assessed for their ability to inhibit the receptor binding to aldosterone by measuring the activity of beta-lactamase on the LiveBLAzer™-FRET B/G substrate.

MR-UAS-bla HEK293T cells are grown in DMEM (high glucose) with GlutaMAX, 10% dialyzed FBS (Invitrogen #26400-036), 25 mM HEPES (Invitrogen 15630-080), 10% pen/strep (Invitrogen #15140-122), 1% MEM NEAA (Invitrogen #11140-50), 80 µg/ml Hygromycin (Invitrogen #10687-010) and 80 µg/ml Zeocin (Invitrogen #R250-05). The beta-lactamase substrate kit reagent solutions A, B, C and D are purchased from Invitrogen (K1030). Cells are grown in a T175 flask and removed with Trypsin. Cells are washed twice in assay buffer (1×DMEM Phenol red-free (Invitrogen #21063-029), 2% Charcoal-stripped FBS (Invitrogen #12676-029), 10% Pen/strep (100×) (Invitrogen #15140-122) and then counted. Cells are then diluted in assay media to a final concentration of $6 \times 10^5$ cells/ml and 20 µL of this preparation is added to each well of a BD 384-well Poly D-Lysine treated plate (Product #356936). 2.75 µl of compound in 100% DMSO is diluted by 30 µl of assay buffer. 3 µl of diluted compound is then added to 30 µl of assay buffer for a further dilution. 10 µl of the second dilution is added to cells to make a 10 µM final compound concentration at 0.2% DMSO. After a 30 minute incubation, 10 µl aldosterone is added to make a final concentration of 1.3 nM. Plates are incubated at 37° C. with 5% $CO_2$ in an incubator for approximately 18 hours. The plates are then removed from the incubator. Kit detection reagents are prepared as follows: For each ml add 6 µl A, into 50 µl B, vortex then add 919 µl C, then vortex, finally add 25 µl D. 10 µl of detection reagent mixture thus prepared is added to each well. Each plate is incubated in the dark at room temperature for 2 hours. The plates are then read on a fluorescence plate reader with bottom reading capabilities using the following filters: excitation filter 409/20 nm, emission filters 460/40 nm and 530/30 nm. The Blue/Green Emission Ratio is calculated for each well using background subtraction.

The Blue/Green Emission ratios are converted to percent of control (POC) values using the formula:

$$POC = 100 * (Blank\ CTRL - Signal)/(BCTRL - PCTRL),$$

where Signal is the test well Blue/Green Emission, BCTRL is the average of background (negative control), which consists of cells, assay buffer and compound buffer and PCTRL is the average of positive control, which consists of cells, aldosterone, and compound buffer. For concentration-responsive compounds, POC as a function of test compound concentration are fitted to a 4-parameter logistic equation of the form:

$$Y = (A + ((B-A)/(1 + 10^{((C-X)*D)})))$$

where A, B, C, and D are fitted parameters X and Y are the independent and dependent variables, respectively. The $IC_{50}$ (50% inhibitory concentration) is determined as the inflection point parameter, C.

The following compounds of the were demonstrated to be MR antagonists through testing in accordance with Cell-based MR antagonism functional assay described above, yielding the $IC_{50}$ values shown in Table 24.

TABLE 24

IC50 value of MR antagonism functional assay

| Compound of Example | MR Functional $IC_{50}$ nM |
|---|---|
| 1 | 160 |
| 2 | 490 |
| 3 | 4600 |
| 4 | 440 |

TABLE 24-continued

IC50 value of MR antagonism functional assay

| Compound of Example | MR Functional IC$_{50}$ nM |
|---|---|
| 5 | 1500 |
| 6 | >10000 |
| 7 | 1200 |
| 10 | >10000 |
| 11 | 7600 |
| 12 | 500 |
| 13 | 1300 |
| 14 | 160 |
| 15 | 1400 |
| 16 | 110 |
| 17 | >10000 |
| 18 | 330 |
| 19 | 3200 |
| 20 | >10000 |
| 21 | >10000 |
| 23 | 2200 |
| 24 | 19 |
| 25 | 150 |
| 26 | 800 |
| 27 | 3400 |
| 28 | 2800 |
| 29 | >10000 |
| 30 | >10000 |
| 31 | 44 |
| 32 | 43 |
| 33 | 37 |
| 34 | >10000 |
| 35 | 140 |
| 36 | 450 |
| 37 | >10000 |
| 38 | 150 |
| 39 | 240 |
| 40 | 500 |
| 41 | 4500 |
| 42 | 97 |
| 43 | 410 |
| 45 | 1000 |
| 46 | >10000 |
| 47 | >10000 |
| 48 | 31 |
| 49 | >10000 |
| 50 | 670 |
| 51 | 1200 |
| 52 | >10000 |
| 53 | >10000 |
| 54 | 920 |
| 55 | >10000 |
| 56 | 690 |
| 57 | 2100 |

Therapeutic Use

The compounds of the invention are antagonists of the mineralocorticoid (aldosterone) receptor. By virtue of this fact the compounds of the formula I can be used for treating various diseases and conditions for which mineralocorticoid (aldosterone) antagonists are already understood by those of skill in the medical art to have therapeutic utility, including but not limited to the treatment of primary hyperaldosteronism and edematous conditions including congestive heart failure, cirrhosis of the liver accompanied by edema and/or ascites, the nephrotic syndrome, essential hypertension and hypokalemia.

Besides being useful for human treatment, these compounds are also useful for veterinary treatment of companion animals, exotic animals and farm animals, and the like.

For treatment of the above-described diseases and conditions, a therapeutically effective dose will generally be in the range from about 0.1 mg to about 15 mg/kg of body weight per dosage of a compound of the invention; preferably, from about 0.1 mg to about 1.5 mg/kg of body weight per dosage. For example, for administration to a 70 kg person, the dosage range would be from about 7 mg to about 1000 mg per dosage of a compound of the invention, preferably from about 7 mg to about 100 mg per dosage. Some degree of routine dose optimization may be required to determine an optimal dosing level and pattern. The active ingredient may be administered from 1 to 6 times a day.

Combination Therapy

These compounds may also be employed in combination therapies with the following compounds: diuretics (e.g. thiazides)

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

Examples of Pharmaceutical Formulations

A. TABLETS

| Component | Amount per tablet (mg) |
| --- | --- |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
| --- | --- |
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
| --- | --- |
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
| --- | --- |
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
| --- | --- |
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
| --- | --- |
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
| --- | --- |
| active substance | 0.005 |
| sorbitan trioleate | 0.1 |
| Monofluorotrichloromethane and difluorodichloromethane (2:3) | To 100 |

The suspension is transferred into a conventional aerosol container with a metering valve. Preferably, 50 μL of suspension are delivered per spray. The active substance may also be metered in higher doses if desired (e.g., 0.02% by weight).

| H. POWDER FOR INHALATION | |
|---|---|
| Component | Amount |
| active substance | 1.0 mg |
| lactose monohydrate | to 25 mg |

| I. POWDER FOR INHALATION | |
|---|---|
| Component | Amount |
| active substance | 2.0 mg |
| lactose monohydrate | to 25 mg |

| J. POWDER FOR INHALATION | |
|---|---|
| Component | Amount |
| active substance | 1.0 mg |
| lactose monohydrate | to 5 mg |

| K. POWDER FOR INHALATION | |
|---|---|
| Component | Amount |
| active substance | 2.0 mg |
| lactose monohydrate | to 5 mg |

In Examples H, I, J, and K, the powder for inhalation is produced in the usual way by mixing the individual ingredients together.

The invention claimed is:

1. A compound of the formula I 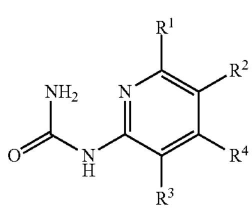 (I)

wherein:

$R^1$, $R^2$ and $R^3$ are each, independently, H, halogen, —CN, —OH, $C_{1-6}$-alkyl (which is optionally substituted with up to 4 halogen atoms), $C_{3-7}$-cycloalkyl, $C_{1-6}$-alkenyl, $C_{1-6}$-alkynyl, $C_{1-6}$-alkoxy, —$NO_2$, —$CO_2R^a$, —C(O)$NR^aR^b$, —$NR^a$C(O)$R^b$, —$NR^aR^b$, —$SO_2R^a$, —$SO_2NR^aR^b$ or —$NR^aSO_2R^b$;

$R^4$ is a group of the formula 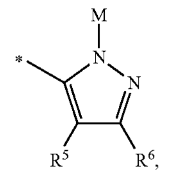 (II)

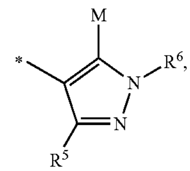

(III)

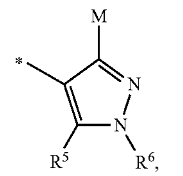

(IV)

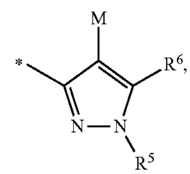

(V)

(VI)

(VII)

or $R^5$, $R^6$, $R^7$, $R^8$, $R^9$ and $R^{10}$ are each, independently, (a) H, (b) halogen, (c) —CN, (d) —OH, (e) $C_{1-6}$-alkyl which is optionally substituted with up to 4 groups which are each, independently, —$OR^a$, —OC(O)$R^a$, —CN, halogen, —$NO_2$, —$CO_2R^a$, —C(O)$NR^aR^b$, —$NR^a$C(O)$R^b$, —$NR^aR^b$, —$SO_2R^a$, —$SO_2OR^a$, —$OSO_2R^a$, —$SO_2NR^aR^b$, —$NR^aSO_2R^b$, $C_{3-7}$-cycloalkyl, an optionally substituted 5 to 6-membered aromatic ring or a saturated or partially saturated 5 to 7-membered carbocyclic ring, (f) $C_{3-7}$-cycloalkyl which is optionally substituted with up to 4 groups which are each, independently, —$OR^a$, —OC(O)$R^a$, —CN, halogen, —$NO_2$, —$CO_2R^a$, —C(O)$NR^aR^b$, —$NR^a$C(O)$R^b$, —$NR^aR^b$, —$SO_2R^a$, —$SO_2OR^a$, —OSO$_2$R$^a$, —SO2NR$^a$R$^b$, —NR$^a$SO$_2$R$^b$, C$_{1-6}$-alkyl or an optionally substituted 5 to 6-membered aromatic ring,
(g) C$_{1-6}$-alkenyl,
(h) C$_{1-6}$-alkynyl,
(i) C$_{1-6}$-alkoxy,
(j) —NO$_2$,
(k) —CO$_2$R$^a$,
(l) —C(O)NR$^a$R$^b$,
(m) —NR$^a$C(O)R$^b$,
(n) —NR$^a$R$^b$,
(o) —SO$_2$R$^a$,
(p) —SO$_2$NR$^a$R$^b$,
(q) —NR$^a$SO$_2$R$^b$,
(r) optionally substituted aryl,
or
(s) an optionally substituted, saturated or partially saturated, 5 to 7 membered carbocyclic ring; or
R$^7$ and R$^8$ (together with the carbon atom between them) and R$^9$ and R$^{10}$, (together with the carbon atom between them) each optionally form a saturated or partially saturated, 3 to 7 membered carbocyclic ring;
M is
(a) C$_{1-6}$-alkyl, optionally substituted with one or more moieties independently selected from the group consisting of halogen, —CN, —OH, —OC(O)R$^a$, C$_{1-6}$-alkyl (which is optionally substituted with up to 4 halogen atoms), C$_{3-6}$-cycloalkyl, C$_{1-6}$-alkenyl, C$_{1-6}$-alkynyl,
C$_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$ and an optionally substituted aryl;
(b) C$_{3-7}$-cycloalkyl, optionally substituted with one or more moieties independently selected from the group consisting of halogen, —CN, —OH, —OC(O)R$^a$, C$_{1-6}$-alkyl (which is optionally substituted with up to 4 halogen atoms), C$_{3-6}$-cycloalkyl, C$_{1-6}$-alkenyl, C$_{1-6}$-alkynyl,
C$_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$ and an optionally substituted aryl; or
(c) a 6 to 10-membered monocyclic or fused bicyclic aromatic ring, optionally substituted with one or more moieties independently selected from the group consisting of halogen, —CN, —OH, —OC(O)R$^a$, C$_{1-6}$-alkyl (which is optionally substituted with up to 4 halogen atoms), C$_{3-6}$-cycloalkyl, C$_{1-6}$-alkenyl, C$_{1-6}$-alkynyl,
C$_{1-6}$-alkoxy, —NO$_2$, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$ and an optionally substituted aryl; and
R$^a$ and R$^b$ are, independently, H or C$_{1-6}$-alkyl which is optionally mono- or di-substituted with —OH, —COOH, C$_{1-6}$-alkoxy, amino or mono- or di-C$_{1-6}$-alkyl amino;
or a tautomer or salt thereof.

2. A compound according to claim 1, wherein:
R$^1$, R$^2$ and R$^3$ are each, independently, H, halogen, —CN, C$_{1-6}$-alkyl (which is optionally substituted with up to 4 halogen atoms), C$_{3-7}$-cycloalkyl and C$_{1-6}$-alkoxy;

R$^4$ is a group of the formula

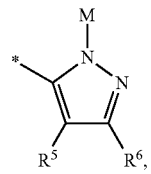
(II)

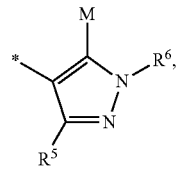
(III)

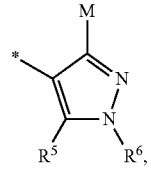
(IV)

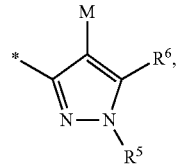
(V)

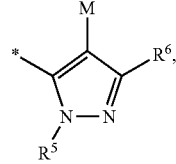
(VI)

or

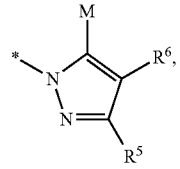
(VII)

R$^5$, R$^6$, R$^7$, R$^8$, R$^9$ and R$^{10}$ are each, independently,
(a) H,
(b) halogen,
(c) —CN,
(d) —OH,
(e) C$_{1-6}$-alkyl which is optionally substituted with up to 4 groups which are each, independently, —OR$^a$, —OC(O)R$^a$, —CN,
halogen, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —NR$^a$SO$_2$R$^b$, C$_{3-7}$-cycloalkyl, a phenyl (which is optionally substituted with up to 2 groups selected from C$_{1-3}$-alkyl, —OR$^a$, —CN or halogen), or a saturated or partially saturated 5 to 7-membered carbocyclic ring,
(f) C$_{3-7}$-cycloalkyl which is optionally substituted with up to 4 groups which are each, independently, —OR$^a$, —OC(O)R$^a$, —CN,
halogen, —CO$_2$R$^a$, —C(O)NR$^a$R$^b$, —NR$^a$C(O)R$^b$, —NR$^a$R$^b$, —SO$_2$R$^a$, —SO$_2$NR$^a$R$^b$, —N $R^aSO_2R^b$, $C_{1-6}$-alkyl, a phenyl (which is optionally substituted with up to 2 groups selected from $C_{1-3}$-alkyl, —$OR^a$, —CN or halogen),
(g) $C_{1-6}$-alkoxy, or
(h) a phenyl which is optionally substituted with up to 2 groups selected from $C_{1-3}$-alkyl, —$OR^a$, —CN or halogen, or $R^7$ and $R^8$ (together with the carbon atom between them) and $R^9$ and $R^{10}$, (together with the carbon atom between them) each optionally form a saturated or partially saturated, 3 to 7 membered carbocyclic ring;

M is
(a) $C_{1-6}$-alkyl, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkenyl, $C_{1-6}$-alkynyl,
$C_{1-6}$-alkoxy, —$NO_2$, —$CO_2R^a$, —C(O)$NR^aR^b$, —$NR^aC(O)R^b$, —$NR^aR^b$, —$SO_2R^a$, —$SO_2NR^aR^b$, —$NR^aSO_2R^b$ and phenyl (which is optionally substituted with up to 3 groups selected from halogen, —CN, —OH, —OC(O)$R^a$, $C_{1-3}$-alkyl, $C_{1-3}$-alkoxy, —$CO_2R^a$, —C(O)$NR^aR^b$, —$NR^aC(O)R^b$, —$NR^aR^b$, —$SO_2R^a$, —$SO_2NR^aR^b$ and —$NR^aSO_2R^b$);
(b) $C_{3-7}$-cycloalkyl, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkenyl, $C_{1-6}$-alkynyl,
$C_{1-6}$-alkoxy, —$NO_2$, —$CO_2R^a$, —C(O)$NR^aR^b$, —$NR^aC(O)R^b$, —$NR^aR^b$, —$SO_2R^a$, —$SO_2NR^aR^b$ and —$NR^aSO_2R^b$;
(c) a 6 to 10-membered monocyclic or fused bicyclic aromatic ring, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkenyl, $C_{1-6}$-alkynyl,
$C_{1-6}$-alkoxy, —$NO_2$, —$CO_2R^a$, —C(O)$NR^aR^b$, —$NR^aC(O)R^b$, —$NR^aR^b$, —$SO_2R^a$, —$SO_2NR^aR^b$ and —$NR^aSO_2R^b$;
and
$R^a$ and $R^b$ are, independently, H or $C_{1-6}$-alkyl which is optionally mono- or di-substituted with —OH, —COOH, $C_{1-6}$-alkoxy, amino or mono- or di-$C_{1-6}$-alkyl amino;
or a tautomer or salt thereof.

3. A compound according to claim 1 wherein:
$R^1$, $R^2$ and $R^3$ are each, independently, H, halogen, —CN or $C_{1-6}$-alkyl (which is optionally substituted with up to 4 halogen atoms);
$R^4$ is a group of the formula

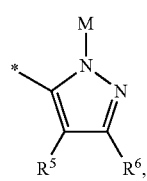
(II)

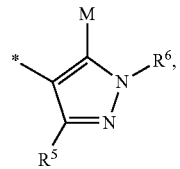
(III)

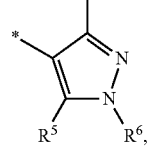
(IV)

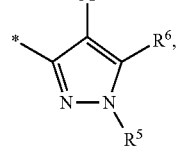
(V)

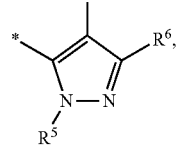
(VI)

(VII)

or $R^5$, $R^6$, $R^7$, $R^8$, $R^9$ and $R^{10}$ are each, independently,
(a) H,
(b) —OH,
(c) halogen, or
(d) $C_{1-6}$-alkyl which is optionally substituted with up to 4 groups which are each, independently, —CN, —$OR^a$, —OC(O)$R^a$ or halogen; or
$R^7$, $R^8$, $R^9$ and $R^{10}$ each are each, independently,
(a) $C_{3-7}$-cycloalkyl which is optionally substituted with up to 4 groups which are each, independently, —CN, —$OR^a$, —OC(O)$R^a$ or halogen;
(b) phenyl which is optionally substituted with up to 2 groups which are $C_{1-3}$-alkyl, —$OR^a$, —CN or halogen;

M is
(a) $C_{1-6}$-alkyl, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkoxy, —$NO_2$, —$CO_2R^a$, —C(O)$NR^aR^b$, —$NR^aC(O)R^b$, —$NR^aR^b$, —$SO_2R^a$, —$SO_2NR^aR^b$, —$NR^aSO_2R^b$ and phenyl (which is optionally substituted with up to 3 groups selected from halogen, —CN, —OH, —OC(O)$R^a$, $C_{1-3}$-alkyl, $C_{1-3}$-alkoxy, —$CO_2R^a$, —C(O)$NR^aR^b$, —$NR^aC(O)R^b$, —$NR^aR^b$, —$SO_2R^a$, —$SO_2NR^aR^b$ and —$NR^aSO_2R^b$);

(b) $C_{3-7}$-cycloalkyl, optionally substituted with one or more moieties independently selected from the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkoxy, —$NO_2$, —$CO_2R^a$, —C(O)$NR^aR^b$, —$NR^aC(O)R^b$, —$NR^aR^b$, —$SO_2R^a$, —$SO_2N R^aR^b$ and —$NR^aSO_2R^b$; or (c) a phenyl, optionally substituted with one or more moieties independently selected the group consisting of halogen, —CN, —OH, —OC(O)$R^a$, $C_{1-6}$-alkyl (which is optionally substituted with up to 4 halogen atoms), $C_{3-6}$-cycloalkyl, $C_{1-6}$-alkoxy, —$NO_2$, —$CO_2R^a$, —C(O)$NR^aR^b$, —$NR^aC(O)R^b$, —$NR^aR^b$, —$SO_2R^a$, —$SO_2N R^aR^b$, and —$NR^aSO_2R^b$;

and $R^a$ and $R^b$ are, independently, H or $C_{1-6}$-alkyl which is optionally mono- or di-substituted with —OH, —COOH, $C_{1-6}$-alkoxy, amino or mono- or di-$C_{1-6}$-alkyl amino or a tautomer or salt thereof.

4. A compound according to claim 1, selected from the group consisting of:

| Compound | Structure |
|---|---|
| 1 | 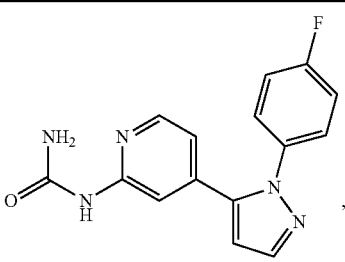 |
| 2 | 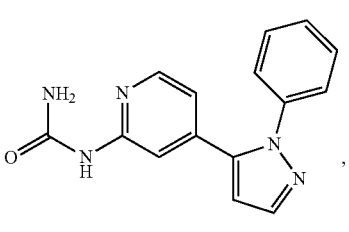 [SMILES: NC(=O)Nc1cc(-c2ccnn2-c2ccccc2)ccn1] |
| 3 | 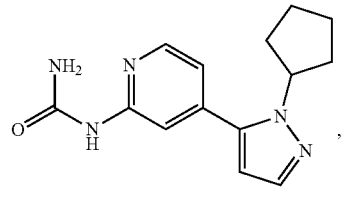 [SMILES: NC(=O)Nc1cc(-c2ccnn2C2CCCC2)ccn1] |
| 4 | 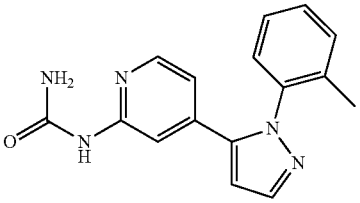 |
| 5 | 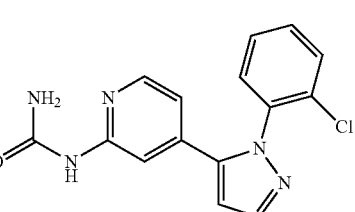 |
| 6 | 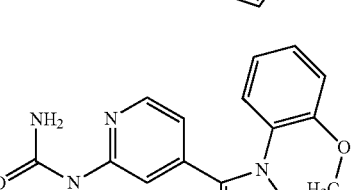 |
| 7 | 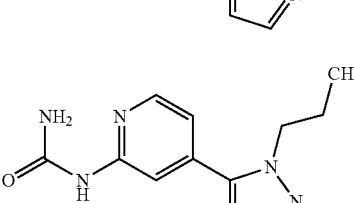 |
| 8 | 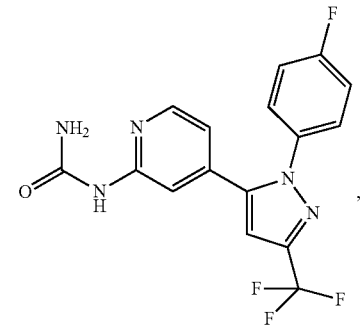 |
| 9 | 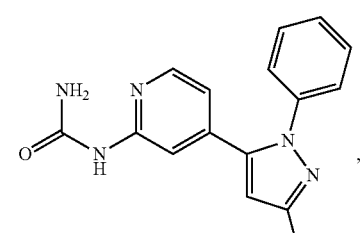 |
| 10 | 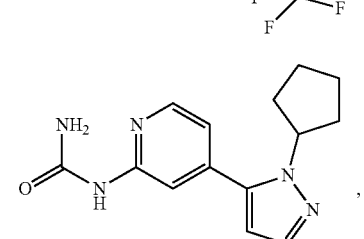 |

-continued

| Compound | Structure |
|---|---|
| 11 | [2-ureido-pyridin-4-yl with 1-(isopropyl)-pyrazol-5-yl] |
| 12 | [2-ureido-pyridin-4-yl with 1-(4-fluoro-2-methylphenyl)-pyrazol-5-yl] |
| 13 | [2-ureido-pyridin-4-yl with 1-(3-methylphenyl)-pyrazol-5-yl] |
| 14 | [2-ureido-pyridin-4-yl with 1-(4-methylphenyl)-pyrazol-5-yl] |
| 15 | [2-ureido-pyridin-4-yl with 1-(3-chlorophenyl)-pyrazol-5-yl] |
| 16 | [2-ureido-pyridin-4-yl with 1-(4-chlorophenyl)-pyrazol-5-yl] |
| 17 | [2-ureido-pyridin-4-yl with 1-(3-methoxyphenyl)-pyrazol-5-yl] |

-continued

| Compound | Structure |
|---|---|
| 18 | [2-ureido-pyridin-4-yl with 1-(4-methoxyphenyl)-pyrazol-5-yl] |
| 19 | [2-ureido-pyridin-4-yl with 1-(3-fluorophenyl)-pyrazol-5-yl] |
| 20 | [2-ureido-pyridin-4-yl with 1-(2-fluorophenyl)-pyrazol-5-yl] |
| 22 | [2-ureido-pyridin-4-yl with 1-(4-fluorobenzyl)-pyrazol-5-yl] and |
| 23 | [2-ureido-pyridin-4-yl with 1-(2-chloro-4-fluorophenyl)-pyrazol-5-yl] | or a tautomer or salt thereof.

5. A pharmaceutically acceptable salt of a compound according to claim 1, 2, 3 or 4.

6. A pharmaceutical composition comprising a compound according to claim 1, 2, 3 or 4, or a pharmaceutically acceptable salt thereof and a pharmaceutically acceptable carrier.

* * * * *